United States Patent [19]
Betts et al.

[11] Patent Number: 5,856,321
[45] Date of Patent: Jan. 5, 1999

[54] ANTIBIOTIC COMPOUNDS

[75] Inventors: Michael John Betts, Wilmslow; Gareth Morse Davies, Macclesfield; Michael Lingard Swain, Stockport, all of England

[73] Assignee: Zeneca Limited, London, United Kingdom

[21] Appl. No.: 833,056

[22] Filed: Apr. 3, 1997

Related U.S. Application Data

[62] Division of Ser. No. 462,037, Jun. 5, 1995, Pat. No. 5,652,233, which is a continuation of Ser. No. 129,056, filed as PCT/GB93/00217 Feb. 2, 1993, Pat. No. 5,478,820.

[30]     Foreign Application Priority Data

Feb. 4, 1992 [GB] United Kingdom ............... 9202298

[51] Int. Cl.⁶ .................. A61K 31/395; C07D 205/00; C07D 487/04; C07D 207/00
[52] U.S. Cl. ..................... 514/210; 540/350; 540/302
[58] Field of Search ................... 540/302, 350; 514/210

[56]            References Cited

U.S. PATENT DOCUMENTS

| | | | |
|---|---|---|---|
| 4,206,219 | 6/1980 | Christensen et al. | 424/274 |
| 4,208,422 | 6/1980 | Christensen et al. | 424/274 |
| 4,218,462 | 8/1980 | Christensen et al. | 424/274 |
| 4,232,036 | 11/1980 | Christensen et al. | 427/274 |
| 4,740,507 | 4/1988 | Sugimara et al. | 514/210 |
| 4,746,736 | 5/1988 | Kim et al. | 540/350 |
| 4,933,333 | 6/1990 | Sunagawa et al. | 514/192 |
| 4,943,569 | 7/1990 | Sunagawa et al. | 514/210 |
| 4,962,103 | 10/1990 | Sunagawa et al. | 514/210 |
| 4,963,544 | 10/1990 | Murata et al. | 514/210 |
| 4,974,544 | 12/1990 | Murata et al. | 118/723 |
| 5,093,328 | 3/1992 | Sunagawa et al. | 514/210 |
| 5,102,997 | 4/1992 | Sugamara et al. | 540/350 |
| 5,194,624 | 3/1993 | Murata et al. | 548/314.7 |
| 5,215,983 | 6/1993 | Murata et al. | 514/210 |
| 5,441,949 | 8/1995 | Jung et al. | 514/210 |
| 5,444,057 | 8/1995 | Jung et al. | 514/210 |
| 5,447,925 | 9/1995 | Betts et al. | 514/210 |
| 5,478,828 | 12/1995 | Betts et al. | 514/210 |
| 5,527,791 | 6/1996 | Betts et al. | 514/210 |
| 5,527,793 | 6/1996 | Junge et al. | 514/210 |
| 5,541,178 | 7/1996 | Betts et al. | 514/210 |
| 5,554,606 | 9/1996 | Betts et al. | 514/210 |
| 5,571,805 | 11/1996 | Jung et al. | 514/210 |
| 5,652,233 | 7/1997 | Betts et al. | 514/210 |

FOREIGN PATENT DOCUMENTS

| | | | |
|---|---|---|---|
| 0017992 | 10/1980 | European Pat. Off. | C07D 487/04 |
| 0126587 | 11/1984 | European Pat. Off. | C07D 487/04 |
| 0160391 | 11/1985 | European Pat. Off. | C07D 487/04 |
| 0182213 | 5/1986 | European Pat. Off. | C07D 487/04 |
| 0243686 | 11/1987 | European Pat. Off. | C07D 487/04 |
| 0443883 | 8/1991 | European Pat. Off. | C07D 477/00 |
| 0472062 | 2/1992 | European Pat. Off. | C07D 499/00 |
| 60-233076 | 11/1985 | Japan . | |
| 9217481 | 10/1992 | WIPO | C07D 477/00 |

OTHER PUBLICATIONS

Betts, CA 118(9) = 80721d (1992).
Betts, CA 118(7) = 59495y (1992).

*Primary Examiner*—José G. Dees
*Assistant Examiner*—Sabiha N. Qazi
*Attorney, Agent, or Firm*—Pillsbury Madison & Sutro LLP

[57]            ABSTRACT

The present invention relates to carbapenems and provides a compound of the formula (I):

$$\text{(I)}$$

or a pharmaceutically acceptable salt or in vivo hydrolysable ester thereof wherein:

$R^1$ is 1-hydroxyethyl, 1-fluoroethyl or hydroxymethyl;

$R^2$ is hydrogen or $C_{1-4}$alkyl;

$R^3$ is hydrogen or $C_{1-4}$alkyl;

$R^4$ and $R^5$ are the same or different and are selected from hydrogen, halo, cyano, $C_{1-4}$alkyl, nitro, hydroxy, carboxy, $C_{1-4}$alkoxy, $C_{1-4}$alkoxycarbonyl, aminosulphonyl, $C_{1-4}$alkylaminosulphonyl, di-$C_{1-4}$-alkylaminosulphonyl, carbamoyl, $C_{1-4}$alkylcarbamoyl, di-$C_{1-4}$alkylcarbamoyl, trifluoromethyl, sulphonic acid, amino, $C_{1-4}$alkylamino, di-$C_{1-4}$alkylamino, $C_{1-4}$alkanoylamino, $C_{1-4}$alkanoyl(N—$C_{1-4}$alkyl) amino, $C_{1-4}$alkanesulphonamido and $C_{1-4}$alkylS(O)$_n$—wherein n is zero, one or two:

with the proviso that there is no hydroxy or carboxy substituent in a position ortho to the link to —$NR^3$—. Processes for their preparation, intermediates in their preparation, their use as therapeutic agents and pharmaceutical compositions containing them.

37 Claims, No Drawings

ANTIBIOTIC COMPOUNDS

This is a division of application Ser. No. 08/462,037 filed Jun. 5, 1995, now U.S. Pat. No. 5,652,233, which is a continuation of application Ser. No. 08/129,056, now U.S. Pat. No. 5,478,820, which is a 371 of PCT/GB93/00217, filed Feb. 2, 1993.

The present invention relates to carbapenems and in particular to such compounds containing a carboxy substituted phenyl group. This invention further relates to processes for their preparation, to intermediates in their preparation, to their use as therapeutic agents and to pharmaceutical compositions containing them.

The compounds of this invention are antibiotics and can be used in the treatment of any disease that is conventionally treated with antibiotics for example in the treatment of bacterial infection in mammals including humans.

Carbapenems were first isolated from fermentation media in 1974 and were found to have broad spectrum antibacterial activity. Since this discovery substantial investigations have been made into new carbapenem derivatives and many hundreds of patents and scientific papers have been published.

The first, and so far the only, carbapenem to be commercially marketed is imipenem (N-formimidoyl thienamycin). This compound has a broad spectrum of antibacterial activity.

The present invention provides compounds with a broad spectrum of antibacterial activity including against both Gram positive and negative, aerobic and anaerobic bacteria. They exhibit good stability to beta-lactamases. In addition representative compounds of this invention exhibit a very favourable duration of action.

The carbapenem derivatives referred to herein are named in accordance with the generally accepted semi-systematic nomenclature:

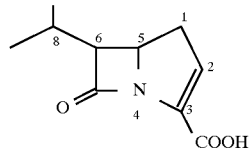

Accordingly the present invention provides a compound of the formula (I):

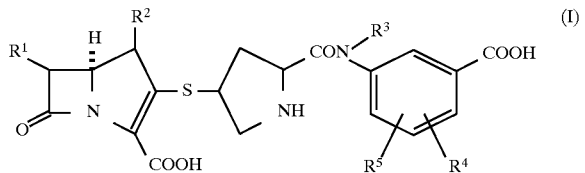

or a pharmaceutically acceptable salt or in vivo hydrolysable ester thereof wherein:

$R^1$ is 1-hydroxyethyl, 1-fluoroethyl or hydroxymethyl;
$R^2$ is hydrogen or $C_{1-4}$alkyl;
$R^3$ is hydrogen or $C_{1-4}$alkyl;
$R^4$ and $R^5$ are the same or different and are selected from hydrogen, halo, cyano, $C_{1-4}$alkyl, nitro, hydroxy, carboxy, $C_{1-4}$alkoxy, $C_{1-4}$alkoxycarbonyl, aminosulphonyl, $C_{1-4}$alkylaminosulphonyl, di-$C_{1-4}$-alkylaminosulphonyl, carbamoyl, $C_{1-4}$alkylcarbamoyl, di-$C_{1-4}$ alkylcarbamoyl, trifluoromethyl, sulphonic acid, amino, $C_{1-4}$alkylamino, di-$C_{1-4}$alkylamino, $C_{1-4}$alkanoylamino, $C_{1-4}$alkanoyl(N—$C_{1-4}$alkyl) amino, $C_{1-4}$alkanesulphonamido and $C_{1-4}$alkylS(O)$_n$- wherein n is zero, one or two:

with the proviso that there is no hydroxy or carboxy substituent in a position ortho to the link to —NR$^3$—.

Alkyl when used herein includes straight chain and branched chain substituents for example methyl, ethyl, n-propyl, isopropyl, n-butyl and isobutyl.

Preferably $R^1$ is 1-hydroxyethyl.

$R^2$ is hydrogen or $C_{1-4}$alkyl for example methyl, ethyl, n-propyl, isopropyl or n-butyl. Preferably $R^2$ is hydrogen or methyl and in particular $R^2$ is methyl.

$R^3$ is hydrogen or $C_{1-4}$alkyl for example methyl, ethyl, n-propyl, isopropyl or n-butyl. Preferably $R^3$ is hydrogen.

$R^4$ and $R^5$ are the same or different and are selected from hydrogen; halo for example fluoro, bromo or chloro; cyano; $C_{1-4}$alkyl for example methyl, ethyl, n-propyl, isopropyl or n-butyl; nitro; hydroxy; carboxy; $C_{1-4}$alkoxy for example methoxy or ethoxy; $C_{1-4}$alkoxycarbonyl for example methoxycarbonyl, ethoxycarbonyl and n-propoxycarbonyl; aminosulphonyl; $C_{1-4}$alkylaminosulphonyl for example methylaminosulphonyl and ethylaminosulphonyl; di-$C_{1-4}$alkylamino-sulphonyl for example di-methylaminosulphonyl, methylethylaminosulphonyl and di-ethylaminosulphonyl; carbamoyl; $C_{1-4}$alkylcarbamoyl for example methylcarbamoyl or ethylcarbamoyl; di-$C_{1-4}$alkylcarbamoyl for example dimethylcarbamoyl or diethylcarbamoyl; trifluoromethyl; sulphonic acid; amino; $C_{1-4}$alkylamino for example methylamino or ethylamino; di-$C_{1-4}$alkylamino for example dimethylamino or diethylamino; $C_{1-4}$alkanoylamino for example acetamido or propionamido; $C_{1-4}$alkanoyl(N—$C_{1-4}$alkyl)amino for example N-methylacetamido; $C_{1-4}$alkanesulphonamido for example methanesulphonamido; and $C_{1-4}$alkylS(O)$_n$- for example methylthio, methylsulphinyl or methylsulphonyl.

In a particular aspect a suitable class of compounds is that in which $R^4$ and $R^5$ are the same or different and are selected from hydrogen, fluoro, chloro, hydroxy, carboxy, cyano, nitro, methyl, ethyl, methoxy, ethoxy, methoxycarbonyl, carbamoyl, methylcarbamoyl, dimethylcarbamoyl, trifluoromethyl, sulphonic acid, methylsulphinyl, methylsulphonyl, methanesulphonamido or acetamido.

$R^4$ and $R^5$ may both be other than hydrogen but, in general, it is particularly preferred that at least one of $R^4$ and $R^5$ is hydrogen.

Particularly preferred compounds are those in which $R^4$ is hydrogen, carboxy, fluoro, chloro, methyl, methoxy, cyano, sulphonic acid or methoxycarbonyl and $R^5$ is hydrogen.

The present invention covers all epimeric, diastereoisomeric and tautomeric forms of the compounds of the formula (I) wherein the absolute stereochemistry at the 5-position is as illustrated in formula (I). When a bond is represented by a wedge, this indicates that in three dimensions the bond would be coming out of the paper and when a bond is hatched, this indicates that in three dimensions the bond would be going back into the paper. The compounds of the formula (I) have a number of other stereocentres, namely: within the group $R^1$ (when $R^1$ is 1-hydroxyethyl or 1-fluoroethyl); at the 6-position; at the 1-position (when $R^2$ is $C_{1-4}$alkyl); and at the 2' and 4' positions in the pyrrolidine ring:

(II)

Preferred compounds are those in which the beta-lactam ring protons are in trans configuration with respect to one another. When $R^1$ is 1-hydroxyethyl or 1-fluoroethyl it is preferred that the 8-substituent has the R-configuration. Thus a preferred class of compounds is that of the formula (III):

(III)

and pharmaceutically acceptable salts and in vivo hydrolysable esters thereof, wherein $R^2$, $R^3$, $R^4$ and $R^5$ are as hereinbefore defined.

When $R^2$ is $C_{1-4}$alkyl for example methyl it is preferred that the compound is in the form of the 1R configuration.

Preferred compounds are those in which the pyrrolidine ring has the following absolute stereochemistry at the 2'- and 4'-positions:

A preferred class of compounds of the present invention is that of the formula (IV):

(IV)

and pharmaceutically acceptable salts and in vivo hydrolysable esters thereof wherein $R^3$, $R^4$, and $R^5$ are as defined hereinbefore in formula (I).

Particularly preferred compounds within the formula (IV) are those wherein $R^3$ is hydrogen and $R^4$ and $R^5$ are the same or different and are selected from hydrogen, fluoro, chloro, hydroxy, carboxy, cyano, nitro, methyl, ethyl, methoxy, ethoxy, methoxycarbonyl, carbamoyl, methylcarbamoyl, dimethylcarbamoyl, methanesulphonyl, trifluoromethyl, sulphonic acid, methylsulphinyl, methanesulphonamido or acetamido.

Especially preferred compounds within the formula (IV) are those wherein $R^3$ and $R^5$ are both hydrogen and $R^4$ is hydrogen, carboxy, fluoro, chloro, methyl, methoxy, cyano, sulphonic acid or methoxycarbonyl.

Suitable pharmaceutically acceptable salts include acid addition salts such as hydrochloride, hydrobromide, citrate, maleate and salts formed with phosphoric and sulphuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. For the avoidance of doubt there may be one, two or three salt-forming cations dependent on the number of carboxylic acid functions and the valency of said cations.

Preferred pharmaceutically acceptable salts are sodium and potassium salts. However, to facilitate isolation of the salt during preparation, salts which are less soluble in the chosen solvent may be preferred whether pharmaceutically acceptable or not.

In vivo hydrolysable esters are those pharmaceutically acceptable esters that hydrolyse in the human body to produce the parent compound. Such esters can be identified by administering, eg. intravenously to a test animal, the compound under test and subsequently examining the test animal's body fluids. Suitable in vivo hydrolysable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy-$C_{1-6}$alkyl esters for example 1-cyclohexyloxycarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention. Suitable in vivo hydrolysable ester forming groups for hydroxy include acetyl, propionyl, pivaloyl, $C_{1-4}$alkoxycarbonyl for example ethoxycarbonyl and phenylacetyl.

Particular compounds of the present invention are:

(1R,5S,6S,8R,2'S,4'S)-2-(2-(3-carboxy-5-hydroxyphenylcarbamoyl)pyrrolidin-4-ylthio)-6-(1-hydroxyethyl)-1-methylcarbapenem-3-carboxylic acid, (1R,5S,6S,8R,2'S,4'S)-2-(2-(3-carboxy-4-chlorophenylcarbamoyl)pyrrolidin-4-ylthio)-6-(1-hydroxyethyl)-1-methylcarbapenem-3-carboxylic acid, (1R,5S,6S,8R,2'S,4'S)-2-(2-(3-carboxy-6-chlorophenylcarbamoyl)pyrrolidin-4-ylthio)-6-(1-hydroxyethyl)-1-methylcarbapenem-3-carboxylic acid, (1R,5S,6S,8R,2'S,4'S)-2-(2-(3-carboxyphenylcarbamoyl)pyrrolidin-4-ylthio)-6-(1-hydroxyethyl)-1-methylcarbapenem-3-carboxylic acid, (1R,5S,6S,8R,2'S,4'S)-2-(2-(3-carboxy-6-methanesulphonylphenylcarbamoyl)pyrrolidin-4-ylthio)-6-(1-hydroxyethyl)-1-methylcarbapenem-3-carboxylic acid, (1R,5S,6S,8R,2'S,4'S)-2-(2-(3-carboxy-4-fluorophenylcarbamoyl)pyrrolidin-4-ylthio)-6-(1-hydroxyethyl)-1-methylcarbapenem-3-carboxylic acid, (1R,5S,6S,8R,2'S,4'S)-2-(2-(3-carboxy-6-fluorophenylcarbamoyl)pyrrolidin-4-ylthio)-6-(1-hydroxyethyl)-1-methylcarbapenem-3-carboxylic acid, (1R,5S,6S,8R,2'S,4'S)-2-(2-(3-carboxy-2,4-difluorophenylcarbamoyl)pyrrolidin-4-ylthio)-6-(1-hydroxyethyl)-1-methylcarbapenem-3-carboxylic acid, (1R,5S,6S,8R,2'S,4'S)-2-(2-(3,4-dicarboxyphenylcarbamoyl)pyrrolidin-4-ylthio)-6-(1-hydroxyethyl)-1-methylcarbapenem-3-carboxylic acid, (1R,5S,6S,8R,2'S,4'S)-2-(2-(3-carboxy-4-hydroxyphenylcarbamoyl)pyrrolidin-4-ylthio)-6-(1-hydroxyethyl)-1-methylcarbapenem-3-carboxylic acid, (1R,5S,6S,8R,2'S,4'S)-2-(2-(3,5-dicarboxyphenylcarbamoyl)pyrrolidin-4-ylthio)-6-(1-hydroxyethyl)-1-methylcarbapenem-3-carboxylic acid, (1R,5S,6S,8R,2'S,4'S)-2-(2-(2-carbamoyl-3-carboxyphenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-4-carbamoylphenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-5-carbamoylphenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-5-acetamidophenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-4-acetamidophenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-5-methylsulphonamidophenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-5-sulphophenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-6-carbamoylphenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-2-dimethylaminocarbonylphenylcarbamoyl)pyrrolidin-4-ylthio)-6-(1-hydroxyethyl)-1-methylcarbapenem-3-carboxylic acid,
(5R,6S,8R,2'S,4'S)-2-(2-(3-carboxyphenylcarbamoyl)pyrrolidin-4-ylthio)-6-(1-hydroxyethyl)carbapenem-3-carboxylic acid,
(1R,5S,6S,8R,2'S,4'S)-2-(2-(3-carboxy-4-methylphenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-5-methylphenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-6-methylphenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-2-methoxyphenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-4-methoxyphenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-5-methoxyphenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-6-methoxyphenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-4,6-dimethoxyphenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-5-methoxycarbonylphenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-5-cyanophenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-5-trifluoromethylphenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-4,6-difluorophenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-6-methylsulphinylphenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-5-methylsulphonylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-5-fluorophenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-6-cyanophenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy N'-methylphenylcarbamoyl)pyrrolidin-4-ylthio)-6-(1-hydroxyethyl)-1-methylcarbapenem-3-carboxylic acid,
and pharmaceutically acceptable salts and in vivo hydrolysable esters thereof.

Preferred compounds of the present invention are:
(1R,5S,6S,8R,2'S,4'S)-2-(2-(3-carboxy-5-methylphenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-5-methoxyphenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-6-methoxyphenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-5-methoxycarbonylphenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-5-cyanophenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-6-chlorophenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxyphenylcarbamoyl)pyrrolidin-4-ylthio)-6-(1-hydroxyethyl)-1-methylcarbapenem-3-carboxylic acid.
(1R,5S,6S,8R,2'S,4'S)-2-(2-(3-carboxy-4-fluorophenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-carboxy-6-fluorophenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3,4-dicarboxyphenylcarbamoyl)pyrrolidin-4-ylthio)-6-(1-hydroxyethyl)-1-methylcarbapenem-3-carboxylic acid.
(1R,5S,6S,8R,2'S,4'S)-2-(2-(3,5-dicarboxyphenylcarbamoyl)pyrrolidin-4-ylthio)-6-(1-hydroxyethyl)-1-methylcarbapenem-3-carboxylic acid.
(1R,5S,6S,8R,2'S,4'S)-2-(2-(3-carboxy-5-sulphophenylcarbamoyl)pyrrolidin-4-ylthio)-6-(1-hydroxyethyl)-1-methylcarbapenem-3-carboxylic acid,
and pharmaceutically acceptable salts thereof.

In order to use a compound of the formula (I) or a pharmaceutically acceptable salt or in vivo hydrolysable ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or in vivo hydrolysable ester thereof and a pharmaceutically acceptable carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, emulsions, dispersible powders, suppositories and sterile injectable aqueous or oily solutions or suspensions.

The compounds of the present invention may be formulated as dry powder filled vials, which may contain the compound of the present invention alone or as a dry blended mixture. For example an acidic compound of the present invention may be dry blended with an alkali metal carbonate or bicarbonate. Freeze dried formulations of compounds of the present invention, alone or as a mixture with standard excipients, are possible. Standard excipients include structure formers, cryoprotectants and pH modifiers, such as, mannitol, sorbitol, lactose, glucose, sodium chloride, dextran, sucrose, maltose, gelatin, bovine serum albumin (BSA), glycine, mannose, ribose, polyvinylpyrrolidine (PVP), cellulose derivatives, glutamine, inositol, potassium glutamate, erythritol, serine and other amino acids and buffer agents e.g. disodium hydrogen phosphate and potassium citrate.

In addition to the compounds of the present invention the pharmaceutical composition of this invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenecid) and inhibitors of metabolising enzymes (for example inhibitors of dehydropeptidases, for example Z-2-acylamino-3-substituted propenoates such as cilastatin) and N-acylated amino acids (for example see EP-A-178911) which reduce adverse effects on the kidney.

A suitable pharmaceutical composition of this invention is one suitable for oral administration in unit dosage form, for example a tablet or capsule which contains between 100 mg and 1 g of the compound of this invention.

A preferred pharmaceutical composition of the invention is one suitable for intravenous, subcutaneous or intramuscular injection, for example a sterile injectable containing between 1 and 50% w/w of the compound of this invention.

Specific examples of compositions, which are constituted as a 1% solution in water, freeze dried and may be made up by adding 0.9% aqueous sodium chloride solution to give the required concentration, preferably 1 mg–10 mg/ml, are as follows:

| Composition 1 | |
|---|---|
| Compound of Example 1 | 50 mg |
| Composition 2 | |
| Compound of Example 1 | 50 mg |
| Glycine | 31 mg |

Further specific examples of compositions are as above, but where the compound of example 1 is replaced by any one of examples 2 to 37.

The pharmaceutical compositions of the invention will normally be administered to man in order to combat infections caused by bacteria, in the same general manner as that employed for imipenem due allowance being made in terms of dose levels for the potency and duration of action of the compound of the present invention relative to the clinical use of imipenem. Thus each patient will receive a daily intravenous, subcutaneous or intramuscular dose of 0.05 to 5 g, and preferably 0.1 to 2.5 g, of the compound of this invention, the composition being administered 1 to 4 times per day, preferably 1 or 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a suitable daily oral dose is 0.05 to 5 g of the compound of this invention, the composition being administered 1 to 4 times per day.

In a further aspect the present invention provides a process for preparing the compounds of the formula (I) or a pharmaceutically acceptable salt or in vivo hydrolysable ester thereof which process comprises deprotecting a compound of the formula (V):

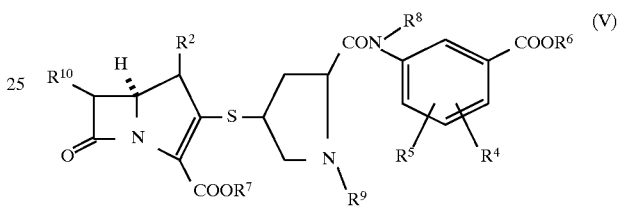

wherein $R^2$, $R^4$ and $R^5$ are as hereinbefore defined ($R^4$ and $R^5$ being optionally protected if appropriate); —$COOR^6$ and —$COOR^7$ are carboxy or protected carboxy; $R^8$ is a group $R^3$ or an amino protecting group; $R^9$ is hydrogen or an amino protecting group; and $R^{10}$ is a group $R^1$, protected 1-hydroxyethyl or protected hydroxymethyl; and wherein at least one protecting group is present; and thereinafter if necessary;

(i) forming a pharmaceutically acceptable salt, (ii) esterifying to form an in vivo hydrolysable ester.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

The compounds of the formula (V) are novel and form another aspect of the invention.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (eg isopropyl, t-butyl);

lower alkoxy lower alkyl groups (eg methoxymethyl, ethoxymethyl, isobutoxymethyl); lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxycarbonyloxyethyl, 1-ethoxycarbonyloxyethyl); aryl lower alkyl groups (eg p-methoxybenzyl, o-nitrobenzyl, p-nitrobenzyl, benzhydryl and phthalidyl); tri(lower alkyl)silyl groups (eg trimethylsilyl and t-butyldimethylsilyl); tri(lower alkyl)silyl lower alkyl groups (eg trimethylsilylethyl); and (2–6C)alkenyl groups (eg allyl and vinylethyl).

Methods particularly appropriate for the removal of carboxyl protecting groups include for example acid-, base-, metal- or enzymically-catalysed hydrolysis.

Examples of hydroxyl protecting groups include lower alkenyl groups (eg allyl); lower alkanoyl groups (eg acetyl); lower alkoxycarbonyl groups (eg t-butoxycarbonyl); lower alkenyloxycarbonyl groups (eg allyloxycarbonyl); aryl lower alkoxycarbonyl groups (eg benzoyloxycarbonyl, p-methoxybenzyloxycarbonyl, o-nitrobenzyloxycarbonyl, p-nitrobenzyloxycarbonyl); tri lower alkylsilyl (eg trimethylsilyl, t-butyldimethylsilyl) and aryl lower alkyl (eg benzyl) groups.

Examples of amino protecting groups include formyl, aralkyl groups (eg benzyl and substituted benzyl, eg p-methoxybenzyl, nitrobenzyl and 2,4-dimethoxybenzyl, and triphenylmethyl); di-p-anisylmethyl and furylmethyl groups; lower alkoxycarbonyl (eg t-butoxycarbonyl); lower alkenyloxycarbonyl (eg allyloxycarbonyl); aryl lower alkoxycarbonyl groups (eg benzyloxycarbonyl, p-methoxybenzyloxycarbonyl, o-nitrobenzyloxycarbonyl, p-nitrobenzyloxycarbonyl; trialkylsilyl (eg trimethylsilyl and t-butyldimethylsilyl); alkylidene (eg methylidene); benzylidene and substituted benzylidene groups.

Methods appropriate for removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolytically.

Preferred protecting groups for carboxy and hydroxy groups in compounds of the formula (I) are the groups allyl and p-nitrobenzyl. A preferred method for removal of the allyl group is by palladium catalysis using tetrakis (triphenylphosphine)palladium and Meldrum's acid, in a dipolar aprotic solvent tetrahydrofuran mixture, such as dimethylsulphoxide/tetrahydrofuran or 1,3-dimethyl-2-oxo-tetrahydro- pyrimidine/tetrahydrofuran, or an alcohol/tetrahydrofuran mixture such as isopropanol/tetrahydrofuran or ethanol/tetrahydrofuran, preferably at ambient temperature. Alternatively, methylaniline may be used in place of Meldrum's acid, in dichloromethane. These conditions allow isolation of the product by precipitation of the sodium salt on the addition of a sodium salt such as sodium 2-ethylhexanoate.

A preferred method for removal of the p-nitrobenzyl group is hydrogenation using a palladium catalyst.

In another aspect of the present invention the compounds of the formulae (I) and (V) may be prepared by a) reacting compounds of the formulae (VI) and (VII):

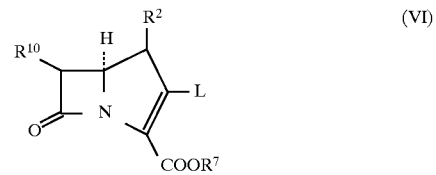

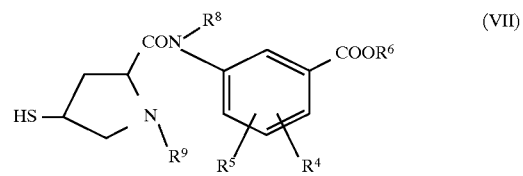

wherein $R^2$, $R^4$–$R^{10}$ are as hereinbefore defined and L is a leaving group, or b) cyclising a compound of the formula (VIII):

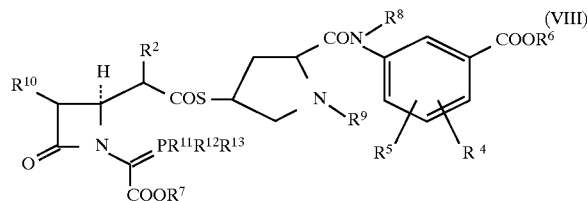

wherein $R^2$, $R^4$–$R^{10}$ as hereinbefore defined and $R^{11}$–$R^{13}$ are independently selected from $C_{1-6}$alkoxy, aryloxy, di-$C_{1-6}$alkylamino and diarylamino or any two of $R^{11}$–$R^{13}$ represent o-phenylenedioxy; or one of $R^{11}$–$R^{13}$ is $C_{1-4}$alkyl, allyl, benzyl or phenyl, and the other two values are independently selected from $C_{1-4}$alkyl, trifluoromethyl or phenyl, wherein any phenyl group is optionally substituted with $C_{1-3}$alkyl or $C_{1-3}$alkoxy:

and wherein any functional group is optionally protected and thereinafter if necessary:
(i) removing any protecting groups;
(ii) forming a pharmaceutically acceptable salt;
(iii) esterifying to form an in vivo hydrolysable ester.

Suitably in the compound of the formula (VI) L is the reactive ester of a hydroxy group such as a sulphonate (for example $C_{1-6}$alkanesulphonyloxy, trifluoromethanesulphonyloxy, benzenesulphonyloxy, toluenesulphonyloxy), a phosphoric ester (for example a diarylphosphoric ester such as diphenylphosphoric ester) or L is a halide (for example chloride). In an alternative L is a sulphoxide for example —SOCH=CH—NHCOCH3 which may be readily displaced. Preferably L is diphenylphosphoric ester (—OP(O)(OPh)$_2$).

Compounds of the formula (VI) and their preparation are well known in the carbapenem literature, for example see EP-A-126587, EP-A-160391, EP-A-243686 and EP-A-343499.

The reaction between the compounds of the formulae (VI) and (VII) is typically performed in the presence of a base such as an organic amine for example di-isopropylethylamine or an inorganic base for example an alkali metal carbonate such as potassium carbonate. The reaction is conveniently performed at a temperature between −25° C. and ambient, suitably at about −20° C. The reaction is generally performed in an organic solvent such as acetonitrile or dimethylformamide. The reaction is generally performed in a manner similar to that described in the literature for similar reactions.

The compounds of the formula (VII) are novel and form another aspect of the present invention.

The compounds of the formula (VII) may be prepared by the deprotection of a compound of the formula (IX):

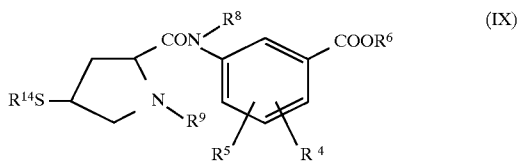

wherein $R^4$–$R^6$, $R^8$ and $R^9$ as hereinbefore defined and $R^{14}$ is a protecting group, for example $C_{1-6}$alkanoyl, $C_{1-6}$alkoxycarbonyl or benzoyl. Preferred values for $R^{14}$ are acetyl and t-butoxycarbonyl. The compounds of the formula (IX) can be converted to the compounds of the formula (VII) by standard methods of deprotection, for example acetyl groups can be removed by basic hydrolysis in aqueous alkanol or alkenol for example allyl alcohol.

The compounds of the formula (IX) are novel and form another aspect of the present invention.

The compounds of the formula (IX) may be prepared by the reaction of an activated derivative of a compound of the formula (X), which may be formed in situ, with a compound of the formula (XI):

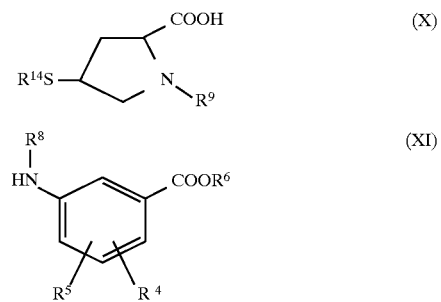

wherein $R^4$–$R^6$, $R^8$, $R^9$ and $R^{14}$ are as hereinbefore defined. Activated derivatives of the compound of the formula (X) include acid halides, anhydrides and 'activated' esters such as 1H-benzo[1,2,3]triazol-1-yl, pentafluorophenyl and 2,4,5-trichlorophenyl esters or the benzimidazol-2-yl ester of the thiocarboxylic acid corresponding to (X). The reaction of the compounds of the formulae (X) and (XI) is performed under standard methods, for example in the presence of Vilsmeier reagent (thus forming the reactive derivative of (X) in situ) at temperatures in the region –30° C. to 25° C., preferably in the region –20° C. to 5° C.

The compounds of the formulae (X) and (XI) are prepared by standard methods known to the skilled chemist such as the methods of the Examples hereinafter, the methods described in EP-A-126587 or by methods analogous or similar thereto.

Suitably, in the compounds of the formula (VIII), $R^{11}$–$R^{13}$ are independently selected from C1–6 alkoxy such as methoxy, ethoxy, isopropoxy, n-propoxy or n-butoxy; aryloxy such as optionally phenoxy; di-$C_{1-6}$alkylamino such as dimethylamino or diethylamino; diarylamino such as diphenylamino or any two of $R^{11}$–$R^{13}$ represent o-phenylenedioxy. Preferably each of $R^{11}$–$R^{13}$ have the same value and are $C_{1-6}$alkoxy for example methoxy, ethoxy, isopropoxy or n-butoxy or are phenoxy.

The compounds of the formula (VIII) are cyclized under conventional conditions known in the art to form compounds of the formula (V). Typical conditions are heating in a substantially inert organic solvent such as toluene, xylene or ethyl acetate at temperatures in the region 60°–150° C. Typically the reaction is performed in an atmosphere of nitrogen and is carried out in the presence of a radical scavenger for example hydroquinone.

The compounds of the formula (VIII) may be formed and cyclized in situ. The compounds of the formula (VIII) may conveniently be prepared by reacting compounds of the formulae (XII) and (XIII):

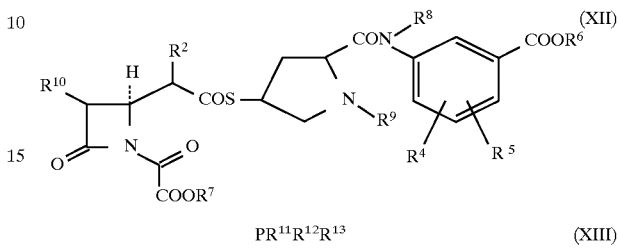

$$PR^{11}R^{12}R^{13} \quad (XIII)$$

wherein $R^2$, and $R^4$–$R^{13}$ are as hereinbefore defined. Suitably the compound of the formula (XIII) is a phosphite or is the functional equivalent of such a compound.

The reaction between the compounds of the formulae (XII) and (XIII) is conveniently performed in an organic solvent such as toluene, xylene, ethyl acetate, chloroform, dichloromethane, acetonitrile or dimethylformamide. Typically the reaction is carried out at an elevated temperature for example 60°–150° C.

The compounds of the formula (XII) may be prepared by a number of methods known in the art. For example the compounds of the formula (XII) may be prepared by the acylation of a compound of the formula (XIV):

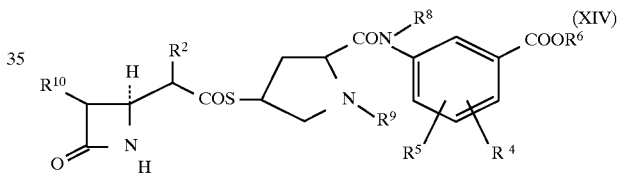

wherein $R^2$, $R^4$–$R^6$, and $R^8$–$R^{10}$ are as hereinbefore defined with a compound of the formula (XV):

wherein $R^7$ is as hereinbefore defined.

The compounds of the formula (XIV) may be prepared by reacting compounds of the formulae (XVI) and (VII):

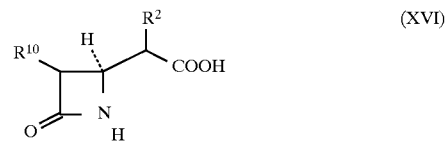

wherein $R^2$ and $R^{10}$ are as hereinbefore defined. The compounds of the formula (XVI) are known in the art and may be reacted with the compounds of the formula (VII) under conventional acylation methods known in the art.

Compounds of the formulae (VII), (XII) and (XIV) are novel and, as such, form another aspect of this invention.

The following biological test methods, data and Examples serve to illustrate the present invention.

Antibacterial Activity

The pharmaceutically acceptable carbapenem compounds of the present invention are useful antibacterial agents having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. In particular the carbapenems of the present invention show good stability to beta-lactamases and have a particularly good elimination half life in mammals. In general compounds show significant improvement over imipenem.

The antibacterial properties of the compounds of the invention may also be demonstrated in vivo in conventional tests.

Carbapenem compounds have generally been found to be relatively non-toxic to warm-blooded animals, and this generalisation holds true for the compounds of the present invention. Compounds representative of the present invention were administered to mice at doses in excess of those required to afford protection against bacterial infections, and no overt toxic symptoms or side effects attributable to the administered compounds were noted.

The following results were obtained for representative compounds on a standard in vitro test system using Diagnostic Sensitivity Test. The antibacterial activity is described in terms of the minimum inhibitory concentration (MIC) determined by the agar-dilution technique with an inoculum size of $10^4$ CFU/spot.

| | MIC ($\mu$g/ml) EXAMPLE | | | | |
|---|---|---|---|---|---|
| ORGANISM | 1 | 2 | 4 | 10 | ceftriaxone |
| *Enterobacter cloacae* 029 | 0.06 | 0.03 | 0.03 | 0.01 | 0.06 |
| *Enterobacter cloacae* 108 | 1.00 | 1.00 | 0.50 | 0.25 | 32 |
| *E. coli* TEM | 0.03 | 0.02 | 0.02 | 0.01 | 0.03 |
| *S. aureus* 147N | 0.25 | 0.50 | 0.25 | 0.13 | 2.0 |

In the examples (a) NMR spectra were taken at 200 MHz or 400 MHz;

(b) Allyloxy means the propen-1-yloxy group —OCH$_2$CH=CH$_2$;

(c) THF means tetrahydrofuran;

(d) DMF means dimethylformamide;

(e) Meldrum's acid is 2,2-dimethyl-1,3-dioxane-4,6-dione.

(f) Evaporation of solvents was carried out under reduced pressure;

(g) EtOAc means ethyl acetate;

(h) EEDQ means N-ethoxycarbonyl-2-ethoxy-1,2-dihydroquinoline;

(i) DMSO means dimethyl sulfoxide;

(j) DCCI means dicyclohexylcarbodiimide; and (k) The peak positions in NMR spectra taken in DMSO-d$_6$ and acetic acid-d$_4$ vary depending on the ratio of DMSO to acetic acid.

EXAMPLE 1

(1R,5S,6S,8R,2'S,4'S)-2-(2-(3-Carboxy-5-hydroxyphenylcarbamoyl)pyrrolidin-4-yl-thio)-6-(1-hydroxyethyl)-1-methylcarbapenem-3-carboxylic acid, disodium salt To a solution of allyl(1R,5S,6S,8R,2'S,4'S)-2-(1-allyloxycarbonyl-2-(3-allyloxy-5-allyloxycarbonylphenylcarbamoyl)pyrrolidin-4-ylthio)-6-(1-hydroxyethyl)-1-methylcarbapenem-3-carboxylate (500 mg, 0.72 mM) and 2,2-dimethyl-1,3-dioxane-4,6-dione (Meldrum's acid, 829 mg, 5.75 mM) in a mixture of DMF (8 ml) and THF (4 ml), under an argon atmosphere, was added tetrakis(triphenylphosphine)palladium (83 mg, 0.072 mM). The solution was stirred, under argon with protection from light, for 2 hours. The solution was diluted with diethyl ether (40 ml), and the resultant precipitate centrifuged, and the supernatant was removed. The product was washed by resuspension in ether followed by centrifugation, and finally dried under high vacuum. The crude product was dissolved in water (10 ml) and the pH adjusted to 6.8 with NaHCO$_3$. After filtration, the solution was subjected to chromatography on Diaion CHP20P resin, and the fractions combined as appropriate to give the title product (66%). Nmr (DMSO-d$_6$+acetic acid-d$_4$): $\delta$ 1.18 (d, 6H); 1.82 (m, part obscured, 1H); 2.79 (m, 1H); 3.03 (dd, 1H); 3.22 (dd, 1H); 3.38 (quintet, 1H); 3.57 (dd, 1H); 3.82 (quintet, 1H); 3.99 (quintet, 1H); 4.19 (dd+m, 2H); 7.13 (t, 1H); 7.44 (t, 1H); 7.65 (t, 1H).

The starting materials were prepared as follows:

Allyl 3-allyloxy-5-aminobenzoate

3-Hydroxy-5-nitrobenzoic acid (3.9 g, 21.3 mM) was dissolved in DMF (55 ml), and anhydrous K$_2$CO$_3$ (11.78 g, 76.5 mM) added with stirring. Allyl bromide (5.4 ml, 62.4 mM) was run in, and the mixture stirred for 18 hours at ambient temperature. The solvent was removed by evaporation, the residue treated with water, the pH was adjusted to 5.5, and product was extracted into ethyl acetate. The combined extracts were washed with aqueous NaH$_2$PO$_4$, water, brine, and dried over MgSO$_4$. The residue after evaporation was subjected to chromatography on silica, eluting with a mixture of petrol/EtOAc (10:1), to give allyl 3-allyloxy-5-nitrobenzoate (5.94 g, 90%). Nmr (CDCl$_3$): $\delta$ 4.66 (dt, 2H); 4.87 (dt, 2H); 5.31–5.52 (m, 4H); 5.94–6.14 (m, 2H); 7.92 (m, 2H); 8.46 (t, 1H).

Ms (CI): 264 (MH)$^+$

The above ester (2 g, 7.6 mM) was dissolved in ethyl acetate (15 ml), and added to a suspension of SnCl$_2$.2H$_2$O (13.7 g, 61 mM), heated under reflux, in ethyl acetate (35 ml) under argon. The mixture was heated to reflux for 4 hours, cooled, and poured into a mix of 880 ammonia (20 ml) and water (20 ml). The organic layer was separated and three further extractions made with ethyl acetate. The combined extracts were washed with dilute ammonia solution, water and brine, dried over MgSO$_4$, and evaporated to give a yellow oil of allyl 3-allyloxy-5-aminobenzoate (1.53 g, 86%). Nmr (CDCl$_3$): $\delta$ 3.60 (br, 2H); 4.53 (dt, 2H); 4.78 (dt, 2H); 5.25–5.44 (m, 4H); 5.96–6.12 (m, 2H); 6.43 (dt, 1H); 7.00 (m, 2H).

Ms (CI): 233 (MH)$^+$

Preparation of Side Chain Pyrrolidin-4-ylthioacetate

The cyclohexylamine salt of 4-acetylthio-1-allyloxycarbonyl-2-carboxy-pyrrolidine (5.6 g, 15 mM) was suspended in ethyl acetate, and shaken successively with 2M HCl (20 ml and 10 ml), water and brine, and the ethyl acetate layer dried over MgSO$_4$. Evaporation gave the free acid. Vilsmeier reagent was prepared by treatment of dimethylformamide (0.51 ml, 6.6 mM) in dichloromethane (20 ml) under argon with oxalyl chloride (0.52 ml, 6 mM) in dichloromethane (5 ml) for 30 minutes. 4-Acetylthio-1-allyloxycarbonyl-2-carboxypyrrolidine (1.64 g, 6 mM) in dichloromethane (7 ml) was added to this in one portion, followed by N-methylmorpholine (0.79 ml, 7.2 mM), in dichloromethane (3 ml) and stirring continued for 30 minutes at −10°. After cooling to −20°, allyl 3-allyloxy-5-aminobenzoate (1.39 g, 5.9 mM) plus N-methylmorpholine (0.79 ml, 7.2 mM) dissolved in dichloromethane (15 ml) were added dropwise. The temperature was allowed to rise to 0°, and the reaction stored for 18 hours. After dilution with dichloromethane (100 ml), the mixture was washed with 2M HCl, H₂O, and saturated NaHCO₃, dried over MgSO₄, and evaporated. Crude material was purified by medium pressure chromatography on silica using a gradient of petrol in dichloromethane (3:1 to 2:1) to give (2S,4S)-1-allyloxycarbonyl-2-(3-allyloxy-5-allyloxycarbonylphenylcarbamoyl)pyrrolidin-4-ylthioacetate as a gum (2.37 g, 81%). Nmr (CDCl₃): δ 2.32 (s, 3H); 2.58 (br, 2H); 3.39 (dd, 1H); 4.03 (quintet, 1H); 4.13 (dd, 1H); 4.55 (t, part obscured, 1H); 4.58 (dt, 2H) 4.68 (dt, 2H); 4.81 (dt, 2H); 5.23–5.49 (m, 6H); 5.84–6.15 (m, 3H); 7.36 (t, 1H); 7.57 (t, 1H); 7.66 (t, 1H); 9.10 (br, 1H).

Ms (+ve FAB): 489 (MH)⁺, 511 (M+Na)⁺

Conversion to Pyrrolidin-4-ylthiols (2S,4S)-4-Acetylthio-1-allyloxycarbonyl-2-(3-allyloxy-5-allyloxycarbonylphenylcarbamoyl)pyrrolidine (1.89 g, 3.9 mM) was dissolved in allyl alcohol (25 ml) and the solution flushed with argon. 1M Sodium hydroxide (4 ml, 4 mM) was added, the mixture stirred at ambient temperature for 2 hours, and then evaporated to dryness. The residue taken up in ethyl acetate (100 ml), washed with 2M HCl, water, NaHCO₃, brine, dried (MgSO₄) and evaporated, to give (2S,4S)-1-allyloxycarbonyl-2-(3-allyloxy-5-allyloxycarbonylphenylcarbamoyl)pyrrolidin-4-ylthiol as a gum (1.57 g, 76%). Crude material was used in the next stage.

Preparation of Protected Carbapenems

A solution of allyl(1R,5R,6S,8R)-6-(1-hydroxyethyl)-1-methyl-2-diphenylphosphoryloxycarbapenem-3-carboxylate (1.5 g, 3 mM) was dissolved in dry acetonitrile (18 ml) under argon, cooled to −20°, and diisopropylethylamine (0.63 ml, 3.6 mM) added, followed by dropwise addition of (2S,4S)-1-allyloxycarbonyl-2-(3-allyloxy-5-allyloxycarbonylphenylcarbamoyl)pyrrolidin-4-yl-thiol (1.57 g, 3.5 mM) in acetonitrile (12 ml). The reaction mixture was then stored at −20° for 3 days. Solvent was evaporated, and the residue purified by medium pressure chromatography on silica with gradient elution (dichloromethane/ethyl acetate 40:60 to 70:30), to give allyl(1R,5S,6S,8R,2'S,4'S)-2-(1-allyloxycarbonyl-2-(3-allyloxy-5-allyloxycarbonylphenylcarbamoyl)pyrrolidin-4-ylthio)-6-(1-hydroxyethyl)-1-methylcarbapenem-3-carboxylate as a gum (1.25 g, 60%). Nmr (CDCl₃): δ 1.23 (d, 3H); 1.35 (d, 3H); 2.65 (br, 2H); 3.26,3.31 (dd overlapping m, 2H); 3.46 (m, 1H); 3.79 (quintet, 1H); 4.01 (dd, 1H); 4.19–4.29 (m, 2H); 4.50–4.78 (m, 9H); 5.19–5.46 (m, 8H); 5.83–6.12 (m, 4H); 7.36 (br s, 1H); 7.64 (m, 2H); 9.00 (br, 1H).

Ms (+ve FAB): 696 (MH)⁺, 718 (M+Na)⁺

Allyl(1R,5R,6S,8R)-6-(1-hydroxyethyl)-1-methyl-2-diphenylphosphoryloxy-carbapenem-3-carboxylate was prepared as follows.

To a solution of allyl(1R,5S,6S,8R)-6-(1-hydroxyethyl)-1-methyl-2-oxocarbapenam-3-carboxylate (2.66 mmol) [prepared in situ from allyl 2-diazo-3-oxo-4-methyl-4-(3-(1-hydroxyethyl)-2-oxoazetidin-4-yl)butanoate and rhodium octanoate: see for example EP-A-208889] and diisopropylethylamine (1.1 equivalents in acetonitrile, at 0° C., under an argon atmosphere, was added dropwise diphenyl chlorophosphate (1.1 equivalents). The solution was stirred at ambient temperature for 30 minutes to form the corresponding 2-diphenylphosphoryloxycarbapenem.

The following further examples were prepared:

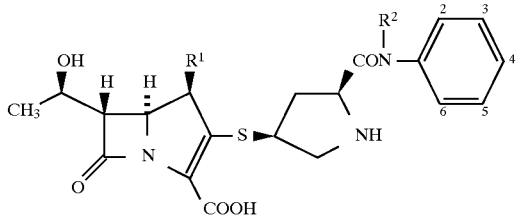

| | | POSITION OF PHENYL SUBSTITUENT | | | | | |
|---|---|---|---|---|---|---|---|
| Example | 2 | 3 | 4 | 5 | 6 | R¹ | R² |
| 2 | H | COOH | Cl | H | H | Me | H |
| 3 | H | COOH | H | H | Cl | Me | H |
| 4 | H | COOH | H | H | H | Me | H |
| 5 | H | COOH | H | H | SO₂CH₃ | Me | H |
| 6 | H | COOH | F | H | H | Me | H |
| 7 | H | COOH | H | H | F | Me | H |
| 8 | F | COOH | F | H | H | Me | H |
| 9 | H | COOH | COOH | H | H | Me | H |
| 10 | H | COOH | OH | H | H | Me | H |
| 11 | H | COOH | H | COOH | H | Me | H |
| 12 | H | COOH | H | H | H | Me | H |
| 13 | H | COOH | H | CONH₂ | H | Me | H |
| 14 | H | COOH | H | H | CONH₂ | Me | H |
| 15 | CONMe₂ | COOH | H | H | H | Me | H |
| 16 | H | COOH | H | NHCOCH₃ | H | Me | H |
| 17 | H | COOH | NHCOCH₃ | H | H | Me | H |
| 18 | H | COOH | H | NHSO₂Me | H | Me | H |
| 19 | H | COOH | H | SO₃H | H | Me | H |
| 20 | H | COOH | H | H | H | H | H |
| 21 | H | COOH | H | CN | H | Me | H |
| 22 | H | COOH | H | OMe | H | Me | H |
| 23 | H | COOH | H | H | SOMe | Me | H |

-continued

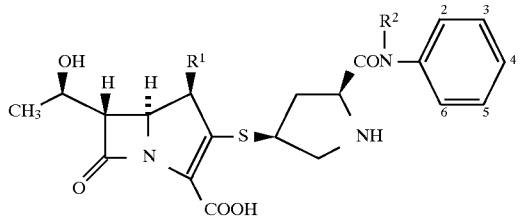

POSITION OF PHENYL SUBSTITUENT

| Example | 2 | 3 | 4 | 5 | 6 | R¹ | R² |
|---|---|---|---|---|---|---|---|
| 24 | H | COOH | H | SO₂Me | H | Me | H |
| 25 | H | COOH | H | CF₃ | H | Me | H |
| 26 | H | COOH | H | H | OMe | Me | H |
| 27 | H | COOH | OMe | H | H | Me | H |
| 28 | OMe | COOH | H | H | H | Me | H |
| 29 | H | COOH | H | H | Me | Me | H |
| 30 | H | COOH | Me | H | H | Me | H |
| 31 | H | COOH | H | Me | H | Me | H |
| 32 | H | COOH | H | —COOMe | H | Me | H |
| 33 | H | COOH | F | H | F | Me | H |
| 34 | H | COOH | OMe | H | OMe | Me | H |
| 35 | H | COOH | H | H | CN | Me | H |
| 36 | H | COOH | H | F | H | Me | H |
| 37 | H | COOH | H | H | H | Me | Me |

EXAMPLE 2

(1R,5S,6S,8R,2'S,4'S)-2-(2-(3-Carboxy-4-chlorophenylcarbamoyl)pyrrolidin-4-ylthio)-6-(1-hydroxyethyl)-1-methylcarbapenem-3-carboxylic acid, disodium salt was prepared in the same general manner as Example 1 except that after the addition of the palladium catalyst the solution was gently warmed to dissolve the catalyst and was stirred under argon with protection from light for 1 hour. A solution of sodium 2-ethylhexanoate in THF was added and the combined solutions poured into THF with vigorous stirring. The resultant precipitate was centrifuged and supernatant removed. The product was washed twice by resuspension in THF followed by centrifugation and finally dried under high vacuum to give the title product. Nmr (DHSO-d₆+acetic acid-d₄): δ 1.17 (d, 6H); 1.85 (m, obscured, 1H); 2.73 (m, obscured, 1H); 2.95 (dd, 1H); 3.21 (dd, 1H); 3.40 (m, 1H); 3.54 (dd, 1H); 3.78 (quintet, 1H); 3.99 (t, 1H); 4.11 (t, 1H); 4.18 (dd, 1H); 7.41 (d, 1H); 7.75 (dd, 1H); 8.06 (d, 1H).

Ms (+ve FAB): 532/534 (MH)⁺, (Na salt)⁺; 554/556 (Na₂ salt)⁺

The starting materials were prepared as follows:

2-Chloro-5-nitrobenzoic acid was allylated essentially as in Example 1, except that the final extraction solvent was toluene, to give allyl 2-chloro-5-nitrobenzoate. Nmr (CDCl₃): δ 4.89 (dt, 2H); 5.33–5.51 (m, 2H); 5.96–6.15 (m, 1H); 7.66 (d, 1H); 8.27 (dd, 1H); 8.72 (d, 1H).

Ms (CI): 241/243 M⁺, 259/261 (M+NH₄)⁺

Stannous chloride dihydrate was refluxed in ethanol, under an argon blanket, to give a solution. The heat was removed, and the above nitro compound in ethanol was run in. Refluxing was then continued for 3 hours, the mixture cooled, and solvents removed. The residue was dissolved in ethyl acetate, and treated with 880 ammonia until basic. The organic phase was decanted from precipitated tin salts, and the slurry re-extracted similarly with more solvent. Combined organic phases were then washed with diluted ammonia, water, and brine, before drying over MgSO₄. Evaporation gave allyl 5-amino-2-chlorobenzoate. Nmr (CDCl₃): δ 3.74 (br, 2H); 4.81 (dt, 2H); 5.27–5.47 (m, 2H); 5.93–6.13 (m, 1H); 6.73 (dd, 1H); 7.15 (d, 1H); 7.24 (d, 1H).

Ms (CI): 212/214 M⁺, 229/231 (M+NH₄)⁺

The above amine was condensed with proline acid as Example 1, purifying by chromatography using a gradient of dichloromethane/diethyl ether (100:0 to 95:5) to give (2S, 4S)-1-allyloxycarbonyl-2-(3-allyloxycarbonyl-4-chlorophenylcarbamoyl)pyrrolidin-4-ylthioacetate. Nmr (CDCl₃): δ 2.33 (s, 3H); 2.57 (br, 2H); 3.39 (dd, 1H); 4.03 (quintet, 1H); 4.13 (dd, 1H); 4.55 (t, 1H); 4.66 (dt, 2H) 4.83 (dt, 2H); 5.24–5.47 (m, 4H); 5.85–6.02 (m, 2H); 7.36 (d, 1H); 7.70 (dd, 1H); 7.92 (d, 1H); 9.32 (br, 1H).

Ms (+ve FAB): 467/469 (MH)⁺, 489/491 (M+Na)⁺

The above thioacetate was deacetylated to thiol, and condensed with carbapenem phosphate as in Example 1, purifying by chromatography using gradient elution from dichloromethane to ethyl acetate to give allyl(1R,5S,6S,8R, 2'S,4'S)-2-(1-allyloxycarbonyl-2-(3-allyloxycarbonyl-4-chlorophenylcarbamoyl)pyrrolidin-4-ylthio)-6-(1-hydroxyethyl)-1-methylcarbapenem-3-carboxylate. Nmr (CDCl₃): δ 1.24 (d, 3H); 1.36 (d, 3H); 2.65 (br, 2H); 3.25 (dd overlapping m, 2H); 3.48 (m, 1H); 3.80 (quintet, 1H); 3.98 (dd, 1H); 4.20–4.31 (dd overlapping quintet, 2H); 4.52 (t, 1H); 4.51–4.76 (m, 4H); 4.83 (dt, 2H); 5.20–5.47 (m, 6H); 5.85–6.11 (m, 3H); 7.39 (d, 1H); 7.77 (dd, 1H); 7.99 (d, 1H); 9.05 (br, 1H).

Ms (+ve FAB): 674/676 (MH)⁺, 696/698 (M+Na)⁺

EXAMPLE 3

(1R,5S,6S,8R,2'S,4'S)-2-(2-(5-Carboxy-2-chlorophenylcarbamoyl)pyrrolidin-4-yl-thio)-6-(1-hydroxyethyl)-1-methylcarbapenem-3-carboxylic acid, disodium salt was prepared using the technique of Example 2. Nmr (DMSO-d₆+acetic acid-d₄): δ 1.16 (d, 3H); 1.19 (d, 3H); 1.82 (m, obscured, 1H); 2.70 (dd overlapping m, 2H); 3.22 (dd, 1H); 3.35–3.60 (overlapping m, 3H); 3.95–4.08 (overlapping m, 2H); 4.16 (dd, 1H); 7.57 (d, 1H); 7.69 (dd, 1H); 8.36 (d, 1H).

Ms (+ve FAB): 532/534 (MH)⁺, (Na salt)⁺; 554/556 (Na$_2$ salt)⁺

The starting materials were prepared as follows:

4-Chloro-3-nitrobenzoic acid was allylated essentially as in Example 1 above to give allyl 4-chloro-3-nitrobenzoate. Nmr (CDCl$_3$): δ 4.86 (d, 2H); 5.31–5.48 (m, 2H); 5.94–6.13 (m, 1H); 7.50 (d, 1H); 8.18 (dd, 1H); 8.52 (d, 1H).

Ms (CI): 241/243 M⁺, 259/261 (M+NH$_4$)⁺

Reduction of the above nitro compound by the method of Example 2 gave allyl 3-amino-4-chlorobenzoate. Nmr (CDCl$_3$): δ 4.08 (br, 2H); 4.79 (dt, 2H); 5.25–5.44 (m, 2H); 5.92–6.11 (m, 1H); 7.30 (d, 1H); 7.38 (dd, 1H); 7.47 (d, 1H).

Ms (CI): 212/214 M⁺, 229/231 (M+NH$_4$)⁺

The above amine was condensed with proline acid as Example 1, purifying by chromatography using a gradient of dichloromethane/diethyl ether (100:0 to 95:5) to give (2S,4S)-1-allyloxycarbonyl-2-(5-allyloxycarbonyl-2-chlorophenylcarbamoyl)pyrrolidin-4-ylthioacetate. Nmr (CDCl$_3$): δ 2.32 (s, 3H); 2.56 (br, 1H); 2.66 (br, 1H); 3.43 (dd, 1H); 4.04 (quintet, 1H); 4.16 (dd, 1H); 4.61 (t, 1H); 4.66 (dt, 2H) 4.82 (dt, 2H); 5.21–5.45 (m, 4H); 5.84–6.11 (m, 2H); 7.45 (d, 1H); 7.77 (dd, 1H); 9.00 (d, 1H); 9.08 (br, 1H).

Ms (+ve FAB): 467/469 (MH)⁺, 489/491 (M+Na)⁺

The above thioacetate was deacetylated to thiol, and condensed with carbapenem phosphate as Example 1, purifying by chromatography using gradient elution from dichloromethane to ethyl acetate to give allyl(1R,5S,6S,8R,2,S,4'S)-2-(1-allyloxycarbonyl-2-(5-allyloxycarbonyl-2-chlorophenylcarbamoyl)pyrrolidin-4-ylthio)-6-(1-hydroxyethyl)-1-methylcarbapenem-3-carboxylate. Nmr (CDCl$_3$): δ 1.23 (d, 3H); 1.36 (d, 3H); 2.65 (br, 2H); 3.24 (dd overlapping m, 2H); 3.88 (quintet, 1H); 4.08 (m, 1H); 4.19–4.30 (dd overlapping quintet, 2H); 4.60 (t, 1H); 4.67 (m, 4H); 4.82 (dt, 2H); 5.18–5.45 (m, 6H); 5.82–6.01 (m, 3H); 7.44 (d, 1H); 7.76 (dd, 1H); 9.04 (d, 1H); 8.98 (br, 1H).

Ms (+ve FAB): 674/676 (MH)⁺, 696/698 (M+Na)⁺

EXAMPLE 4

(1R,5S,6S,8R,2'S,4'S)-2-(2-(3-Carboxyphenylcarbamoyl)pyrrolidin-4-ylthio)-6-(1-hydroxyethyl)-1-methylcarbapenem-3-carboxylic acid, disodium salt was prepared using the technique of Example 2 except that a mixture of DMSO and THF was used. Nmr (DMSO-d$_6$+acetic acid-d$_4$): δ 1.18 (d, 6H); 1.94 (m, obscured, 1H); 2.85 (m, 1H); 3.10 (dd, 1H); 3.23 (dd, 1H); 3.40 (quintet, 1H); 3.66 (dd, 1H); 3.89 (quintet, 1H); 3.99 (t, 1H); 4.21 (dd, 1H); 4.27 (t, 1H); 7.46 (t, 1H); 7.71 (d, 1H); 7.86 (d, 1H); 8.27 (s, 1H).

Ms (+ve FAB): 498 (MH)⁺, (Na salt)⁺; 520 (Na$_2$ salt)⁺

The starting materials were prepared as follows:

3-Nitrobenzoic acid was allylated essentially as in Example 1, except that the final extraction solvent was diethyl ether, to give allyl 3-nitrobenzoate. Nmr (CDCl$_3$): δ 4.88 (d, 2H); 5.33–5.49 (m, 2H); 5.96–6.17 (m, 1H); 7.66 (t, 1H); 8.41 (td, 2H); 8.88 (t, 1H).

Reduction of the above nitro compound by the method of Example 2, except that the solvent was methanol, gave allyl 3-aminobenzoate. Nmr (CDCl$_3$): δ 3.38 (br, 2H); 4.79 (dt, 2H); 5.24–5.44 (m, 2H); 5.93–6.09 (m, 1H); 6.86 (dm, 1H); 7.21 (t, 1H); 7.37 (t, 1H); 7.45 (dt, 1H).

Preparation of Side Chain Pyrrolidin-4-ylthioacetate (2S,4S)-4-Acetylthio-1-allyloxycarbonyl-2-carboxypyrrolidine (2.54 g, 9.3 mM), allyl 3-aminobenzoate (1.5 g, 8.5 mNM), and 2-ethoxy-1-ethoxycarbonyl-1,2-dihydroquinoline (2.72 g, 11 mM) were dissolved in toluene (50 ml) and stirred for 18 hours at ambient temperature. The reaction mixture was diluted with ethyl acetate (150 ml) and washed with 2M HCl (3 by 30 ml), water, saturated NaHCO$_3$, and brine. Drying over MgSO$_4$ and evaporation gave (2S,4S)-4-acetylthio-1-allyloxycarbonyl-2-(3-allyloxycarbonylphenylcarbamoyl)pyrrolidine as a gum (3.7 g, 100%) in a state sufficiently pure for further work. Nmr (CDCl$_3$): δ 2.32 (s, 3H); 2.60 (br, 2H); 3.40 (dd, 1H); 4.03 (quintet, 1H); 4.13 (dd, 1H); 4.57 (t, 1H); 4.66 (dm, 2H); 4.82 (dt, 2H); 5.23–5.46 (m, 4H); 5.86–6.12 (m, 2H); 7.41 (t, 1H); 7.82 (d, 1H); 7.91 (d, 1H); 8.07 (t, 1H); 9.18 (br, 1H).

The above thioacetate was deacetylated to thiol, and condensed with carbapenem phosphate as Example 1, purifying by chromatography using gradient elution from dichloromethane to ethyl acetate/dichloromethane 1:1, to give allyl(1R,5S,6S,8R,2'S,4'S)-2-(1-allyloxycarbonyl-2-(3-allyloxycarbonylphenylcarbamoyl)pyrrolidin-4-ylthio)-6-(1-hydroxyethyl)-1-methylcarbapenem-3-carboxylate. Nmr (CDCl$_3$): δ 1.24 (d, 3H); 1.36 (d, 3H); 2.64 (br, 2H); 3.26,3.28 (dd overlapping m, 2H); 3.48 (m, 1H); 3.81 (quintet, 1H); 4.01 (dd, 1H); 4.22–4.32 (m, 2H); 4.54 (t, 1H); 4.62–4.75 (m, 4H); 4.82 (m, 2H); 5.19–5.45 (m, 8H); 5.82–6.10 (m, 4H); 7.41 (d, 1H); 7.81 (d, 1H); 7.92 (dm, 1H); 8.11 (t, 1H); 8.98 (br, 1H).

Ms (+ve FAB): 640 (MH)⁺, 662 (M+Na)⁺

EXAMPLE 5

(1R,5S,6S,8R,2'S,4'S)-2-(2-(3-Carboxy-6-methanesulphonylphenylcarbamoyl)pyrrolidin-4-ylthio)-6-(1-hydroxyethyl)-1-methylcarbapenem-3-carboxylic acid disodium salt was prepared from the appropriate protected carbapenem as described in Example 1. Nmr (DMSO-d$_6$+ acetic acid-d$_4$): δ 1.20 (d, 6H); 1.99 (quintet, 1H); 2.75 (m, part obscured, 1H); 2.87 (dd, 1H); 3.22 (s, 3H); 3.25 (dd, part obscured, 1H); 3.44 (quintet, 1H); 3.62 (dd, 1H); 3.75 (quintet, 1H); 4.03 (quintet, 1H); 4.16–4.23 (m, 2H); 7.90 (dd, 1H); 8.17 (d, 1H); 9.00 (d, 1H).

Ms (+ve FAB): 554 (MH)⁺, 576 (Na salt)⁺, 598 (Na$_2$ salt)⁺

The starting materials were prepared as follows:

4-Methanesulphonyl-3-nitrobenzoic acid was allylated essentially as in Example 1, except that crude product was purified by chromatography over silica, eluting with a gradient of dichloromethane to dichloromethane/diethyl ether 9:1, to give allyl 4-methanesulphonyl-3-nitrobenzoate. Nmr (CDCl$_3$): δ 3.45 (s, 3H); 4.90 (dt, 2H); 5.30–5.49 (m, 2H); 5.96–6.12 (m, 1H); 8.29 (d, 1H); 8.40–8.46 (m, 2H).

Reduction as in Example 1, except that the solvent was methanol, gave allyl 3-amino-4-methanesulphonylbenzoate. Nmr (CDCl$_3$): δ 3.07 (s, 3H); 4.82 (dt, 2H); 5.05 (br, 2H); 5.29–5.44 (m, 2H); 5.95–6.11 (m, 1H); 7.46 (m, 2H); 7.81 (d, 1H).

Ms (+ve FAB): 256 (MH)⁺, 273 (M+NH$_4$)⁺

The above amine was condensed with proline acid as Example 1, purifying by chromatography using a gradient of dichloromethane/diethyl ether (100:0 to 90:10), to give (2S,4S)-1-allyloxycarbonyl-2-(5-allyloxycarbonyl-2-methanesulphonylphenylcarbamoyl)pyrrolidin-4-ylthioacetate. Nmr (CDCl$_3$): δ 2.31 (s, 3H); 2.41 (m, 1H); 2.80 (m, 1H); 3.11 (s, 3H); 3.51 (dd, 1H); 4.00–4.18 (m, 2H); 4.53 (dd, 1H); 4.65 (2m, 2H) 4.87 (dt, 2H); 5.23–5.47 (m, 4H); 5.83–6.13 (m, 2H); 7.93 (dd, 1H); 8.03 (d, 1H); 9.09 (br s, 1H).

Ms (+ve FAB): 511 (MH)⁺, 533 (M+Na)⁺

The above thioacetate was deacetylated to thiol, and condensed with carbapenem phosphate as Example 1, purifying by chromatography using gradient elution from dichloromethane through to ethyl acetate to give allyl(1R,5S,6S,8R,2'S,4'S)-2-(1-allyloxycarbonyl-2-(5-allyloxycarbonyl-2-methanesulphonylphenylcarbamoyl)pyrrolidin-4-ylthio)-6-(1-hydroxyethyl)-1-methylcarbapenem-3-carboxylate. Nmr (CDCl$_3$): δ 1.21 (d, 3H); 1.35 (d, 3H); 2.43 (m, 1H); 2.75 (br, 1H); 3.08 (s, 3H); 3.23 (dd overlapping m, 2H); 3.55 (dd, 1H); 3.85–4.08 (m, 2H); 4.19–4.28 (m, 2H); 4.53–4.68 (m, 5H); 4.86 (dt, 2H); 5.17–5.47 (m, 6H); 5.79–6.12 (m, 3H); 7.92 (dd, 1H); 8.00 (d, 1H); 9.16 (br s, 1H); 10.14 (br, 1H).

Ms (+ve FAB): 718 (MH)$^+$, 740 (M+Na)$^+$

EXAMPLE 6

(1R,5S,6S,8R,2'S,4'S)-2-(2-(3-Carboxy-4-fluorophenylcarbamoyl)pyrrolidin-4-yl-thio)-6-(1-hydroxyethyl)-1-methylcarbapenem-3-carboxylic acid To a solution of allyl(1R,5S,6S,8R,2'S,4'S)-2-(1'-allyloxycarbonyl-2'-(3-allyloxycarbonyl-4-fluorophenylcarbamoyl)pyrrolidin-4-ylthio)-6-(1-hydroxyethyl)-1-methylcarbapenem-3-carboxylate (199 mg, 0.3 mM) and 2,2-dimethyl-1,3-dioxane-4,6-dione (Meldrum's acid, 259 mg, 1.8 mM) in DMF (1.5 ml), under an argon atmosphere, was added tetrakis(triphenylphosphine)palladium (10 mg, 0.009 mM) in THF (0.1 ml). The solution was stirred under argon for 2 hours and tetrakis(triphenylphosphine)palladium (5 mg, 0.0045 mM) in THF (0.1 ml) was added. After stirring for 30 minutes, THF (3 ml) and ether (9 ml) were added, the resultant solid filtered off, washed with ether (9 ml), and dried under high vacuum to give the title product (72 mg, 49%). Nmr (DMSO-d$_6$+acetic acid-d$_4$): δ 1.30 (d, 6H); 2.00 (m, part obscured, 1H); 2.91 (m, part obscured, 1H); 3.13 (dd, 1H); 3.36 (dd, 1H); 3.55 (dq, 1H); 3.73 (dd, 1H); 3.95 (m, 1H); 4.12 (m, 1H); 4.29 (dd, 1H); 4.34 (dd, 1H); 7.40 (dd, 1H); 7.98 (m, 1H); 8.32 (dd, 1H).

Ms (+ve FAB): 494 (MH)$^+$, 516 (M+Na)$^+$

The starting materials were prepared as follows:
Allyl 5-amino-2-fluorobenzoate

2-Fluoro-5-nitrobenzoic acid (4.16 g, 22.5 mM) was dissolved in DMF (45 ml), and anhydrous K$_2$CO$_3$ (4.65 g, 33.7 mM) added with stirring. Allyl bromide (2.38 ml, 28.1 mM) was run in, the mixture was stirred for 18 hours at ambient temperature before being poured into water (450 ml) and extracted with diethyl ether (3×100 ml). The combined extracts were dried over MgSO$_4$, and evaporated to give a yellow oil (5.4 g). The oil was purified by chromatography on silica, eluting with a mixture of ethyl acetate/hexane (12.5:87.5), to give allyl 2-fluoro-5-nitrobenzoate (4.64 g, 92%). Nmr (CDCl$_3$): δ 4.89 (d, 2H); 5.30–5.50 (m, 2H); 5.90–6.10 (m, 1H); 7.32 (t, 1H); 8.38–8.46 (m, 1H); 8.86 (dd, 1H).

Ms (EI): 226 (MH)$^+$; (CI): 225 M$^+$, 243 (M+NH$_4$)$^+$

The above ester (2.47 g, 10.97 mM) was dissolved in methanol (40 ml), and stannous chloride dehydrate (9.89 g, 43.76 mM) in conc HCl (9 ml) was added to the stirred solution while maintaining the temperature between 5° and 15°. The mixture was then stirred overnight at ambient temperature before being poured into water (200 ml) and neutralized with solid NaHCO$_3$ (17.6 g) to pH6. The mixture was extracted with chloroform (3×200 ml), the combined extracts were dried over MgSO$_4$, and evaporated to give allyl 5-amino-2-fluorobenzoate (2.09 g, 98%) as a yellow oil. Nmr (CDCl$_3$): δ 3.60 (br s, 2H); 4.82 (dt, 2H); 5.25–5.48 (m, 2H); 5.93–6.12 (m, 1H); 6.78 (ddd, 1H); 6.93 (dd, 1H); 7.20 (dd, 1H).

Ms (EI): 195 M$^+$; (CI): 196 (MH)$^+$; 213 (M+NH$_4$)$^+$

The above amine was condensed with the proline acid as in Example 1. The product was purified by chromatography on silica using ethyl acetate/hexane (42.5:57.5) to give (2S,4S)-1-allyloxycarbonyl-2-(3-allyloxycarbonyl-4-fluorophenylcarbamoyl)pyrrolidin-4-ylthioacetate. Nmr (CDCl$_3$): δ 2.32 (s, 3H); 2.50–2.70 (br s, 2H); 3.40 (d, 1H); 3.98–4.20 (m, 2H); 4.56 (t, 1H); 4.67 (dt, 2H); 4.84 (dt, 2H); 5.20–5.50 (m, 4H); 5.83–6.12 (m, 2H); 7.10 (dd, 1H); 7.80–7.89 (m, 1H); 7.93 (dd, 1H); 8.90–9.40 (br s, 1H).

Ms (+ve FAB): 451 (MH)$^+$, 473 (M+Na)$^+$

Conversion to Pyrrolidin-4-ylthiol (2S,4S)-1-allyloxycarbonyl-2-(3-allyloxycarbonyl-4-fluorophenyl carbamoyl)pyrrolidin-4-ylthioacetate (1.33 g, 2.96 mM) was dissolved in allyl alcohol (30 ml) and the solution flushed with argon. 1M Sodium hydroxide (3.1 ml, 3.1 mM) was added, the mixture stirred at ambient temperature for 30 minutes, treated with acetic acid (0.3 ml), stirred for a further 5 minutes. and then evaporated to dryness. The residue was taken up in ethyl acetate (60 ml), washed with saturated aq. NaHCO$_3$ (60 ml), brine, dried (MgSO$_4$) and evaporated, to give (2S,4S)-1-allyloxycarbonyl-2-(3-allyloxycarbonyl-4-fluorophenylcarbamoyl)pyrrolidin-4-ylthiol as a gum (1.07 g, 89%). The crude material was used as such in the next stage.

The thiol was condensed with carbapenem phosphate as in Example 1, and product purified by chromatography on silica, eluting with ethyl acetate/dichloromethane (75:25) to give allyl(1R,5S,6S,8R,2S',4S')-2-(1-allyloxycarbonyl-2-(3-carboxy-4-fluorophenylcarbamoyl)pyrrolidin-4-ylthio)-6-(1-hydroxyethyl)-1-methylcarbapenem-3-carboxylate. Nmr (CDCl$_3$): δ 1.24 (d, 3H); 1.35 (d, 3H); 2.40–2.80 (br, 2H); 3.24–3.28 (m, 2H); 3.40–3.58 (br, 1H); 3.80 (dq, 1H); 3.99 (dd, 1H); 4.19–4.33 (m, 2H); 4.53 (t, 1H); 4.59–4.77 (m, 4H); 4.77–4.88 (m, 2H); 5.17–5.50 (m, 6H); 5.80–6.13 (m, 3H); 7.10 (dd, 1H); 7.82–7.95 (m, 1H); 8.00 (dd, 1H); 8.70–9.20 (br s, 1H).

Ms (+ve FAB): 658 (MH)$^+$

EXAMPLE 7

(1R,5S,6S,8R,2'S,4'S)-2-(2-(5-Carboxy-2-fluorophenylcarbamoyl)pyrrolidin-4-yl-thio)-6-(1-hydroxyethyl)-1-methylcarbapenem-3-carboxylic acid was prepared from the appropriate protected carbapenem as in Example 6. Nmr (DMSO-d$_6$+acetic acid-d$_4$): δ 1.30 (d, 6H); 1.84 (m, 1H); 2.80–2.93 (m, 2H); 3.36 (dd, 1H); 3.58 (m, 1H); 3.66 (dd, 1H); 3.81 (m, 1H); 4.09( dq, 1H); 4.21 (m, 1H); 4.31 (dd, 1H); 7.56 (dd, 1H); 8.07 (m, 1H); 8.90 (d, 1H).

Ms (+ve FAB): 494 (MH)$^+$, 516 (M+Na)$^+$

The starting materials were prepared as follows:
Allyl 3-amino-4-fluorobenzoate

4-Fluoro-3-nitrobenzoic acid was allylated as in Example 6 to give allyl 4-fluoro-3-nitro benzoate. Nmr (CDCl$_3$): δ 4.87 (dt, 2H); 5.48–5.32 (m, 2H); 5.95–6.14 (m, 1H); 7.40 (dd, 1H); 8.30–8.38 (m, 1H); 8.76 (dd, 1H).

Ms (EI): 225 M$^+$; (CI): 225 M$^+$, 243 (M+NH$_4$)$^+$

The above was reduced essentially as in Example 2, except that methanol was used as solvent to give allyl 3-amino-4-fluorobenzoate. Nmr (CDCl$_3$): δ 3.70 (br, 2H); 4.79 (dt, 2H); 5.25–5.44 (m, 2H); 5.96–6.09 (m, 1H); 7.02 (dd, 1H); 7.41–7.54 (m, 2H).

Ms (EI): 195 M$^+$; (CI): 196 (MH)$^+$

The above amine was condensed with the proline acid as in Example 1, purifying the product by chromatography on silica using ethyl acetate/hexane (50:50) as eluent, to give (2S,4S)-1-allyloxycarbonyl-2-(5-allyloxycarbonyl-2- fluorophenylcarbamoyl)pyrrolidin-4-ylthioacetate. Nmr (CDCl$_3$): δ 2.33 (s, 3H); 2.62 (br, 2H); 3.40 (dd, 1H); 3.98–4.20 (m, 2H); 4.60 (t, 1H); 4.67 (dt, 2H); 4.82 (dt, 2H); 5.2–5.5 (m, 4H); 5.8–6.15 (m, 2H); 7.16 (dd, 1H); 7.83 (ddd, 1H); 8.97 (dd, 1H); 9.27 (br, 1H).

Ms (EI): 451 (MH)$^+$; (CI): 451 (MH)$^+$

The above thioacetate was deacetylated to thiol, condensed with carbapenem phosphate as in Example 6, and the product purified by chromatography (eluting with ethyl acetate) to give allyl(1R,5S,6S,8R,2'S,4'S)-2-(1-allyloxycarbonyl-2-(5-allyloxycarbonyl-2-fluorophenylcarbamoyl)pyrrolidin-4-ylthio)-6-(1-hydroxyethyl)-1-methylcarbapenem-3-carboxylate. Nmr (DHSO-d$_6$+acetic acid-d$_4$): δ 1.90 (m, part obscured, 1H); 2.78 (m, 1H); 3.22 (dd, 1H); 3.26 (m, 1H); 3.52 (m, 1H); 3.83–4.03 (m, 2H); 4.09 (dd, 1H); 4.22 (m, 1H); 4.53 (m, 1H); 4.53–4.65 (m, 4H); 4.80 (dt, 2H); 5.05–5.43 (m, 6H); 5.73–5.98 (m, 2H); 5.98–6.09 (m, 1H); 7.38 (dd, 1H); 7.78 (br s, 1H); 8.49 (m, 1H); 8.62 (d, 1H).

Ms (+ve FAB): 658 (MH)$^+$, 680 (M+Na)$^+$

EXAMPLE 8

(1R,5S,6S,8R,2'S,4'S)-2-(2-(3-Carboxy-2,4-difluorophenyl carbamoylpyrrolidin-4-ylthio)-6-(1-hydroxyethyl)-1-methylcarbapenem-3-carboxylic acid, was prepared from the appropriate protected carbapenem as in Example 7. Nmr: (DMSO-d$_6$+acetic acid-d$_4$): δ 1.29 (d, 6H); 1.94–1.99 (m, part obscured 1H); 2.81–3.07 (m, 1H); 3.05 (dd, 1H); 3.37 (dd, 1H); 3.56 (m, 1H); 3.75 (dd, 1H); 3.92 (q, 1H); 4.10 (dq, 1H); 4.29–4.38 (m, 2H); 7.22 (t, 1H); 8.07 (m, 1H).

Ms (+ve FAB): 512 (MH)$^+$, 534 (M+Na)$^+$

The starting materials were prepared as follows:
Allyl 3-amino-2,6-difluorobenzoate 2,6-Difluoro-3-nitrobenzoic acid was allylated as in Example 6 to give allyl 2,6-difluoro-3-nitrobenzoate. Nmr (CDCl$_3$): 4.90 (dt, 2H); 5.33–5.50 (m, 2H); 5.95–6.03 (m, 1H); 7.09–7.27 (ddd, 1H); 8.22–8.27 (ddd, 1H).

Ms (EI): 244 (MH)$^+$; (CI): 261 (M+NH$_4$)$^+$

The above ester was reduced as in Example 2, except that methanol was used as the solvent, to give allyl 3-amino-2,6-difluorobenzoate. Nmr (CDCl$_3$): δ 4.86 (dt, 2H); 5.27–5.49 (m, 2H); 5.95–6.09 (m, 1H); 6.77–6.86 (m, 2H).

MS (EI): 213 M$^+$; (CI): 214 (MH)$^+$

The above amine was condensed with the proline acid as in Example 1, purifying by chromatography and eluting with ethyl acetate/hexane (40:60), to give (2S,4S)-1-allyloxycarbonyl-2-(3-allyloxycarbonyl-2,4-difluorophenylcarbamoyl)pyrrolidin-4-ylthioacetate. Nmr (CDCl$_3$): δ 2.32 (s, 3H); 2.60 (br, 2H); 3.40 (dd, 1H); 3.95–4.19 (m, 2H); 4.57 (t, 1H); 4.67 (dt, 2H); 4.86 (dt, 2H); 5.20–5.50 (m, 4H); 5.81–6.13 (m, 2H); 6.95 (ddd, 1H); 8.4 (ddd, 1H); 9.2 (br, 1H).

MS (+ve FAB): 469 (MH)$^+$

The above thioacetate was deacetylated to thiol, and condensed with carbapenem phosphate as in Example 6. The product was purified by chromatography on silica, eluting with ethyl acetate, to give allyl(1R,5S,6S,8R,2S',4S')-2-(1-allyloxycarbonyl-2-(3-carboxy-2,4-difluoro phenylcarbamoyl)pyrrolidin-4-ylthio)-6-(1-hydroxyethyl)-1-methylcarbapenem-3-carboxylate. Nmr (CDCl$_3$): δ 1.26 (d, 3H); 1.36 (d, 3H); 1.80 (d, 1H); 2.62 (br, 2H); 3.19–3.36 (m, 2H); 3.44 (dd, 1H); 3.08 (q, 1H); 4.05 (dd, 1H); 4.19–4.33 (m, 2H); 4.50–4.80 (m, 5H); 4.86 (dt, 2H); 5.17–5.50 (m, 6H); 5.82–6.10 (m, 3H); 6.95 (dt, 1H); 8.38 (dt, 1H); 9.00 (br, 1H).

Ms (+ve FAB): 676 (MH)$^+$, 698 (M+Na)$^+$

EXAMPLE 9

(1R,5S,6S,8R,2'S,4'S)-2-(2-(3,4-Dicarboxyphenylcarbamoyl)pyrrolidin-4-ylthio)-6-(1-hydroxyethyl)-1-methylcarbapenem-3-carboxylic acid, trisodium salt was prepared using the technique of Example 2 except that a mixture of DMSO and THF was used. Nmr (DMSO-d$_6$+acetic acid-d$_4$): δ 1.18 (d, 6H); 1.84 (m, part obscured, 1H); 2.78 (m, 1H); 3.02 (dd, 1H); 3.23 (dd, 1H); 3.40 (quintet, 1H); 3.58 (dd, 1H); 3.83 (quintet, 1H); 4.00 (quintet, 1H); 4.20 (dd overlapping m, 2H); 7.92 (dd, 1H); 8.17 (d, 1H); 8.33 (d, 1H).

Ms (+ve FAB): 542 (MH)$^+$, (Na salt)$^+$; 564 (Na$_2$ salt)$^+$

The starting material was prepared as follows:

2-Carboxy-4-nitrobenzoic acid was allylated according to the procedure of Example 1 to give allyl 2-allyloxycarbonyl-4-nitrobenzoate. Nmr (CDCl$_3$): δ 4.85 (dt, 4H); 5.29–5.47 (m, 4H); 5.91–6.12 (m, 2H); 7.88 (d, 1H); 8.38 (dd, 1H); 8.63 (d, 1H).

Reduction of the above nitro compound by the method of Example 2, and purifying by medium pressure chromatography on silica using a gradient of dichloromethane/diethyl ether (100:0 to 90:10), gave allyl 2-allyloxycarbonyl-4-amino-benzoate. Nmr (CDCl$_3$): δ 3.94 (br, 2H); 4.71–4.80 (m, 4H); 5.22–5.42 (m, 4H); 5.88–6.10 (m, 2H); 6.69 (dd, 1H); 6.75 (d, 1H); 7.74 (d, 1H).

The above amine was condensed with proline acid as Example 1, purifying by medium pressure chromatography on silica using a gradient from dichloromethane to 20% diethyl ether in dichloromethane, to give (2S,4S)-1-allyloxycarbonyl-2-(3,4-diallyloxycarbonylphenylcarbamoyl)pyrrolidin-4-ylthioacetate. Nmr (CDCl$_3$): δ 2.32 (s, 3H); 2.59 (br, 2H); 3.37 (dd, 1H); 4.03 (quintet, 1H); 4.12 (dd, 1H); 4.56 (t, 1H); 4.67 (d, 2H); 4.77 (t, 4H); 5.25–5.42 (m, 6H); 5.84–6.11 (m, 3H); 7.79 (m, 3H); 9.52 (br, 1H).

The above thioacetate was deacetylated to thiol, which was condensed without further purification with carbapenem phosphate as Example 1, finally purifying by medium pressure chromatography on silica, using dichloromethane/ethyl acetate 3:2 as eluant, to give allyl(1R,5S,6S,8R,2'S,4'S)-2-(1-allyloxycarbonyl-2-(3,4-diallyloxycarbonylphenylcarbamoyl)pyrrolidin-4-ylthio)-6-(1-hydroxyethyl)-1-methylcarbapenem-3-carboxylate. Nmr (CDCl$_3$): δ 1.24 (d, 3H); 1.35 (d, 3H); 2.62 (br, 2H); 3.26 (dd overlapping m, 2H); 3.47 (br, 1H); 3.81 (quintet, 1H); 3.97 (dd, 1H); 4.19–4.29 (overlapping m, 2H); 4.53 (t, 1H); 4.62–4.82 (m, 8H); 5.19–5.44 (m, 8H); 5.84–6.07 (m, 4H); 7.82 (s, 3H); 9.30 (br, 1H).

EXAMPLE 10

(1R,5S,6S,8R,2'S,4'S)-2-(2-(3-Carboxy-4-hydroxyphenylcarbamoyl)pyrrolidin-4-ylthio)-6-(1-hydroxyethyl)-1-methylcarbapenem-3-carboxylic acid was prepared using the technique of Example 1, except that the crude acid was of sufficient purity, and did not require chromatography. Nmr (DMSO-d$_6$+acetic acid-d$_4$): δ 1.17 (d, 6H); 1.95 (m, obscured, 1H); 2.87 (m, obscured, 1H); 3.17 (dd, 1H); 3.25 (dd, 1H); 3.42 (dt, 1H); 3.75 (dd, 1H); 3.99–4.05 (m, 2H); 4.22 (dd, 1H); 4.33 (t, 1H); 6.76 (d, 1H); 7.56 (dd, 1H); 7.97 (d, 1H).

Ms (+ve FAB): 492 (MH)$^+$, 514 (M+Na)$^+$

The starting materials were prepared as follows:

2-Hydroxy-5-nitrobenzoic acid was allylated essentially as in Example 1, except that the final extraction solvent was diethyl ether, to give allyl 2-allyloxy-5-nitrobenzoate. Nmr (CDCl₃): δ 4.82 (m, 4H); 5.26–5.55 (m, 4H); 5.97–6.13 (m, 2H); 7.49 (d, 1H); 8.41 (dd, 1H); 8.52 (d, 1H).

Reduction of the above nitro compound by the method of Example 2, except that the solvent was methanol, and NaHCO₃ solution was used to basify, gave allyl 2-allyloxy-5-aminobenzoate. Nmr (CDCl₃): δ 3.23 (br, 2H); 4.53 (dt, 2H); 4.79 (d, 2H); 5.21–5.49 (m, 4H); 5.93–6.14 (m, 2H); 6.80 (m, 2H); 7.16 (d, 1H).

The above amine was condensed with proline acid as Example 1, purifying by chromatography using a gradient of dichloromethane/diethyl ether (100:0 to 85:15) to give (2S,4S)-1-allyloxycarbonyl-2-(4-allyloxy-3-allyloxycarbonylphenylcarbamoyl)pyrrolidin-4-ylthioacetate. Nmr (CDCl₃): δ 2.33 (s, 3H); 2.56 (br, 2H); 3.39 (dd, 1H); 4.01 (quintet, 1H); 4.13 (dd, 1H); 4.52 (t, 1H); 4.60 (dt, 2H) 4.66 (m, 2H); 4.81 (dt, 2H); 5.23–5.51 (m, 6H); 5.85–6.13 (m, 3H); 6.91 (d, 1H); 7.76 (dd, 1H); 7.81 (d, 1H); 8.97 (br, 1H).

The above thioacetate was deacetylated to thiol, and condensed with carbapenem phosphate as Example 1, purifying by chromatography using gradient elution from dichloromethane to ethyl acetate to give allyl(1R,5S,6S,8R,2'S,4'S)-2-(1-allyloxycarbonyl-2-(4-allyloxy-3-allyloxycarbonylphenylcarbamoyl)pyrrolidin-4-ylthio)-6-(1-hydroxyethyl)-1-methylcarbapenem-3-carboxylate. Nmr (CDCl₃): δ 1.24 (d, 3H); 1.36 (d, 3H); 2.57 (br, 2H); 3.25, 3.28 (dd overlapping quintet, 2H); 3.47 (br, 1H); 3.78 (quintet, 1H); 4.01 (dd, 1H); 4.18–4.27 (dd overlapping m, 2H); 4.51 (t, 1H); 4.58–4.79 (m, 6H); 4.79 (dt, 2H); 5.19–5.51 (m, 8H); 5.83–6.12 (m, 4H); 6.93 (d, 1H); 7.79 (dd, 1H); 7.85 (d, 1H); 8.88 (br, 1H).

Ms (+ve FAB): 696 (MH)⁺, 718 (M+Na)⁺

EXAMPLE 11

(1R,5S,6S,8R,2'S,4'S)-2-(2-(3,5-Dicarboxyphenylcarbamoyl)pyrrolidin-4-ylthio)-6-(1-hydroxyethyl)-1-methylcarbapenem-3-carboxylic acid was prepared using the technique of Example 1, except that the crude acid was of sufficient purity, and did not need chromatography. Nmr (DMSO-d₆+acetic acid-d₄): δ 1.15 (d, 6H); 1.77 (m, part obscured, 1H); 2.69 (m, part obscured, 1H); 2.85 (m, part obscured, 1H); 3.19 (dd, 1H); 3.33–3.51 (m, 2H); 3.71 (quintet, 1H); 3.94 (quintet, 1H); 4.03 (t, 1H); 4.15 (dd, 1H); 8.18 (t, 1H); 8.45 (d, 2H).

Ms (+ve FAB): 520 (MH)⁺, 542 (M+Na)⁺

The starting materials were prepared as follows:

3-Carboxy-5-nitrobenzoic acid was allylated essentially as in Example 1 to give allyl 3-allyloxycarbonyl-5-nitrobenzoate. Nmr (CDCl₃): δ 4.89–4.93 (m, 4H); 5.33–5.50 (m, 4H); 5.97–6.17 (m, 2H); 9.00 (t, 1H); 9.04 (d, 2H).

Reduction of the above nitro compound by the method of Example 2 gave allyl 3-allyloxycarbonyl-5-aminobenzoate. Nmr (CDCl₃): δ 3.91 (br, 2H); 4.80–4.84 (m, 4H); 5.26–5.45 (m, 4H); 5.96–6.11 (m, 2H); 7.53 (d, 2H); 8.09 (t, 1H).

The above amine was condensed with proline acid as Example 1, to give (2S,4S)-1-allyloxycarbonyl-2-(3,5-diallyloxycarbonylphenylcarbamoyl)pyrrolidin-4-yl-thioacetate. Nmr (CDCl₃): δ 2.33 (s, 3H); 2.60 (br, 2H); 3.40 (dd, 1H); 4.03 (quintet, 1H); 4.14 (dd, 1H); 4.58 (t, 1H); 4.65–4.70 (m, 2H); 4.83–4.87 (m, 4H); 5.24–5.47 (m, 6H); 5.84–6.16 (m, 3H); 8.39 (d, 2H); 8.45 (t, 1H); 9.36 (br, 1H).

The above thioacetate was deacetylated to thiol, and condensed with carbapenem phosphate as Example 1, to give allyl(1R,5S,6S,8R,2'S,4'S)-2-(1-allyloxycarbonyl-2-(3,5-diallyloxycarbonylphenylcarbamoyl)pyrrolidin-4-ylthio)-6-(1-hydroxyethyl)-1-methylcarbapenem-3-carboxylate. Nmr (CDCl₃): δ 1.23 (d, 3H); 1.35 (d, 3H); 2.63 (br, 2H); 3.25, 3.29 (dd overlapping m, 2H); 3.49 (br, 1H); 3.84 (quintet, 1H); 3.98 (dd, 1H); 4.19–4.30 (m, 2H); 4.55 (t, 1H); 4.63–4.78 (m, 4H); 4.84 (d, 4H); 5.19–5.45 (m, 8H); 5.84–6.12 (m, 4H); 8.46 (s, 3H); 9.18 (br, 1H).

Ms (+ve FAB): 724 (MH)⁺, 746 (M+Na)⁺

EXAMPLE 12

(1R,5S,6S,8R,2'S,4'S)-2-(2-(3-Carboxyphenylcarbamoyl)pyrrolidin-4-ylthio)-6-(1-hydroxyethyl)-1-methylcarbapenem-3-carboxylic acid To a solution of 4-nitrobenzyl(1R,5S,6S,8R,2'S,4'S)-2-(2-(3-allyloxycarbonylphenylcarbamoyl)-1-(4-nitrobenzyloxycarbonyl)pyrrolidin-4-ylthio)-6-(1-hydroxyethyl)-1-methylcarbapenem-3-carboxylate (10 g, 12 mM) and Meldrum's acid (5.2 g, 36 mM) in THF (70 ml), under an atmosphere of argon and with the exclusion of light, was added tetrakis(triphenylphosphine)palladium (1.4 g, 1.2 mM). The mixture was stirred at ambient temperature for 30 minutes. The mixture was diluted with ethyl acetate (230 ml) and added to a solution of sodium bicarbonate (1.5 g) in distilled water (200 ml). 10% Pd-charcoal (4 g) was added and the mixture hydrogenated in an atmosphere of hydrogen for 3 hours. The catalyst was filtered, the filtrate extracted with ethyl acetate (2×100 ml) and ether (2×100 ml), and the aqueous layer concentrated under reduced pressure to about 250 ml. This solution was split into two and each sample purified by passage through a 1 liter HP20SS column using water as eluent. The pure fractions were collected and freeze-dried giving the title compound as a pale yellow solid (3.5 g). Nmr (DMSO-d₆+acetic acid-d₄, positions sensitive to exact solvent ratio): δ 1.19 (d, 6H); 1.94 (dt, 1H); 2.97 (dt, 1H); 3.13 (dd, 1H); 3.25 (dd, 1H); 3.42 (dt, 1H); 3.68 (dd, 1H); 3.94 (quintet, 1H); 4.02 (quintet, 1H); 4.22 (dd, 1H); 4.32 (t, 1H); 7.46 (t, 1H); 7.73 (dt,7 1H); 7.88 (dm, 1H); 8.27 (t, 1H).

Ms (+ve FAB): 498 (Na salt), 520 (di-Na salt).

The starting material was prepared as follows;

3-Nitrobenzoic acid (50 g, 0.3M) was allylated by a similar method to that described in Example 1. Solid K₂CO₃ (82.7 g, 0.6M) was added to the acid in dry DMF (700 ml) with stirring. There was a slight exotherm and the mixture became thick. Allyl bromide (38.8 ml, 0.45M) was added over 30 minutes and the mixture was left stirring overnight. After filtration through diatomaceous earth, the solution was evaporated to dryness under reduced pressure and the residue partitioned between ether and aqueous NaHCO₃. The ether layer was washed with dilute HCl, brine and water, dried and evaporated giving a yellow oil (62 g). Nmr (DMSO-d₆): δ 4.85–4.92 (m, 2H); 5.27–5.5 (m, 2H); 5.97–6.2 (m, 1H); 7.85 (t, 1H); 8.37–8.42 (dt, 1H); 8.48–8.54 (dq, 1H); 8.64 (t, 1H).

Without further purification this oil was reduced to allyl 3-aminobenzoate (53 g) using stannous chloride and the method described in example 6. Nmr (CDCl₃): δ 3.6 (broad, 2H); 4.77–4.82 (dt, 2H); 5.24–5.44 (m, 2H); 5.96–6.1 (m, 1H); 6.83–6.88 (m, 1H); 7.17–7.25 (m, 1H); 7.35–7.47 (m, 2H).

The above allyl 3-aminobenzoate (26.6 g, 0.15M) was condensed with 4-acetylthio-1-(4-nitrobenzyloxycarbonyl)-2-carboxypyrrolidine (55.2 g, 0.15M) by suspension in toluene (750 ml) and addition of EEDQ (44.5 g, 0.18M). The mixture was stirred overnight, diluted with EtOAc (2 l) and washed with dilute HCl, water and brine. The EtOAc phase was dried and evaporated, and the residue recrystallised from ethanol giving (2S,4S)-4-acetylthio-1-(4-nitrobenzyloxycarbonyl)-2-(3-allyloxycarbonylphenylcarbamoyl)pyrrolidine (67.7 g). Nmr (DHSO-$d_6$): δ 1.93 (quintet, 1H); 2.9 (m, 1H); 3.35 (m, 1H); 3.91–4.14 (m, 2H); 4.49 (quintet, 1H); 4.81 (dd, 2H); 5.22 (dd, 2H); 5.2–5.44 (m, 2H); 5.95–6.10 (m, 1H); 7.47 (d, 2H); 7.66 (t, 2H); 7.8–7.93 (m, 2H); 8.18–8.3 (m, 2H); 10.31 (s, 1H).

The above thioacetate (52.7 g, 0.1M) was converted to the thiol by dissolving it in degassed allyl alcohol (1 l) and adding aqueous NaOH (2M, 50 ml) at 0C. After 3 hours aqueous HCl (2M, 52.5 ml) was added, the solvent evaporated and the residue partitioned between EtOAc and brine. The EtOAc phase was dried over $MgSO_4$, filtered and evaporated. The thiol was used without further purification.

A solution of 4-nitrobenzyl(1R,5R,6S,8R)-6-(1-hydroxyethyl)-1-methyl-2-diphenylphosphoryloxycarbapenem-3-carboxylate (59.68 g, 0.1M) in acetonitrile (500 ml) and methylene chloride (120 ml) was cooled to –15° C. and ethyl diisopropylamine (52.5 ml) was added slowly. (2S,4S)-1-(4-Nitrobenzyloxycarbonyl)-2-(3-allyloxycarbonylphenylcarbamoyl)pyrrolidin-4-ylthiol (0.1M), in acetonitrile (400 ml) was added under argon and the mixture left overnight. The solvent was evaporated and the residue subjected to chromatography on silica, eluting with methylene chloride, EtOAc and acetonitrile, giving 4-nitrobenzyl(1R,5R,6S,8R,2'S,4'S)-2-(1-(4-nitrobenzyloxycarbonyl)-2-(3-allyloxycarbonylphenylcarbamoyl)pyrrolidin-4-ylthio)-6-(1-hydroxyethyl)-1-methylcarbapenem-3-carboxylate as a yellow solid (52.6 g). Nmr (DMSO-$d_6$+$CD_3OD$): δ 1.26 (d, 3H); 1.35 (d, 3H); 2.2–2.4 (m, 1H); 2.7–2.95 (m, 1H); 3.28–3.40 (m, 2H); 3.54–3.63 (m, 1H); 3.8 (t, 1H); 4.01–4.1 (q, 1H); 4.21–4.33 (m, 2H); 4.61 (dd, 1H); 4.73 (d, 2H); 5.17–5.45 (m, 6H); 5.93–6.11 (m, 1H); 7.37–8.22 (complex pattern of doublets and double doublets, 12H).

EXAMPLE 13

The deprotection and hydrogenation were carried out by a similar method to that described in example 12, except that 4-nitrobenzyl(1R,5S,6S,8R,2'S,4'S)-2-(2-(3-allyloxycarbonyl-5-carbamoylphenylcarbamoyl)-1-(4-nitrobenzyloxycarbonyl)pyrrolidin-4-ylthio)-6-(1-hydroxyethyl)-1-methylcarbapenem-3-carboxylate (0.44 g) was used. After the hydrogenation, the aqueous layer was was freeze-dried, without HP20SS chromatography, to give (1R,5S,6S,8R,2'S,4'S)-2-(2-(3-carboxy-5-carbamoylphenylcarbamoyl)pyrrolidin-4-ylthio)-6-(1-hydroxyethyl)-1-methylcarbapenem-3-carboxylic acid, as a pale yellow solid (125 mg). Nmr (DMSO-$d_6$+acetic acid-$d_4$): δ 1.9 (d, 6H); 1.98–2.06 (m, 1H); 2.85–2.98 (m, 1H); 3.16–3.21 (m, 1H); 3.26 (dd, 1H); 3.43 (quintet, 1H); 3.74 (dd, 1H); 3.91–3.97 (m, 1H); 4.0 (t, 1H); 4.23 (dd, 1H); 4.39 (t, 1H); 8.24 (t, 1H); 8.33 (t, 1H); 8.44 (t, 1H).

The starting material was prepared as follows:

5-Nitroisophthalic acid (5 g) was converted to the mono allyl ester using one equivalent of allyl bromide (2 ml) using a similar method to that described in example 1. The required acid (2.7 g) was extracted from the organic phase with aqueous $NaHCO_3$. The organic layer contained the di-allyl ester (2.7 g). The mono acid, 3-allyloxycarbonyl-5-nitrobenzoic acid, was obtained as a white solid. Nmr ($CDCl_3$): 4.87 (d, 2H); 5.3–5.5 (q, 2H); 5.97–6.15 (m, 1H); 9.01 (t, 3H).

Ms (CI): 252 (MH)$^+$

DCCI (1.3 g) was added to a solution of the above acid (1.5 g) and N-hydroxysuccinimide (0.76 g) in methylene chloride (50 ml) and the mixture stirred at ambient temperature for 2 hours. A white solid was filtered and the solution evaporated to dryness. The active ester was purified on silica gel eluting with methylene chloride then it was dissolved in methylene chloride and treated with ammonia gas at 5° C. The white solid which precipitated was 3-allyloxycarbonyl-5-nitrobenzamide (1.1 g). Nmr (DMSO-$d_6$): δ 4.9 (dt, 2H); 4.88–4.93 (m, 2H); 6.03–6.11 (m, 1H); 7.83 (broad s, 1H); 8.55 (broad s, 1H); 8.75 (t, 1H); 8.84 (t, 1H); 8.94 (t, 1H).

Ms (CI): 268 (M+$NH_4$)$^+$

3-Allyloxycarbonyl-5-nitrobenzamide (1 g) was reduced with $SnCl_2$ by a similar method to the reduction in example 12, giving 3-allyloxycarbonyl-5-aminobenzamide (0.5 g). Nmr (DMSO-$d_6$): 4.78 (dt, 2H); 5.2–5.8 (broad, 2H); 5.26–5.45 (m, 2H); 5.91–6.13 (m, 1H); 7.22 (broad s, 1H); 7.27 (t, 1H); 7.33 (t, 1H); 7.59 (s, 1H).

Ms (CI): 221 (MH)$^+$ (2S,4S)-4-Acetylthio-1-(4-nitrobenzyloxycarbonyl)-2-carboxy-pyrrolidine (0.75 g) was converted to the acid chloride and reacted with 3-allyloxycarbonyl-5-aminobenzamide (0.45 g) by a similar method to that described in example 12. The crude product was subjected to chromatography on silica gel, eluting with EtOAc and giving 4-acetylthio-1-(4-nitrobenzyloxycarbonyl)-2-(3-allyloxycarbonyl-5-carbamoylphenylcarbamoyl)pyrrolidine (0.58 g). Nmr (DMSO-$d_6$): δ 1.92–2.06 (m, 1H); 2.3 (s, 3H); 2.79–2.83 (m, 1H); 3.38 (dd, 1H); 3.97–4.12 (m, 2H); 4.49 (dd, 1H); 4.83 (dt, 2H); 5.19 (dd, 2H); 5.25–5.43 (m, 2H); 5.97–6.11 (m, 1H); 7.31 (broad s, 2H); 7.54 (d, 2H); 8.04 (d, 2H); 8.12 (t, 1H); 8.26 (t, 1H); 8.31 (t, 1H); 10.0 (s, 1H).

The thiol was generated from the above thioacetate by the method described in example 12.

A solution of 4-nitrobenzyl(1R,5R,6S,8R)-6-(1-hydroxyethyl)-1-methyl-2-diphenylphosphoryloxycarbapenem-3-carboxylate (0.6 g) and (2S,4S)-1-(4-nitrobenzyloxycarbonyl)-2-(3-allyloxycarbonyl-5-aminocarbamoylphenylcarbamoyl)pyrrolidin-4-ylthiol (0.48 g) in acetonitrile (20 ml) was reacted by a similar method to that as described in example 12. Purification was by flash chromatography, eluting with EtOAc then 5% MeOH/EtOAc, giving 4-nitrobenzyl (1R,5R,6S,8R,2'S,4'S)-2-(1-(4-nitrobenzyloxycarbonyl)-2-(3-allyloxycarbonyl-5-carbamoylphenylcarbamoyl)pyrrolidin-4-ylthio)-6-(1-hydroxyethyl)-1-methylcarbapenem-3-carboxylate as a yellow solid (0.44 g). Nmr (DMSO-$d_6$): δ 1.19–1.22 (d, 6H); 2.0–2.11 (m, 1H); 2.8–2.92 (m, 1H); 3.32 (dd, 1H); 3.42–3.62 (m, 2H); 3.92–4.2 (m, 2H); 4.31 (broad d, 1H); 4.53 (q, 1H); 4.84 (d, 2H); 4.98–5.46 (m, 6H); 5.98–6.14 (m, 1H); 7.42–8.52 (complex pattern of doublets and double doublets, 11H ).

EXAMPLE 14

The deprotection and hydrogenation was carried out by a similar method to that described in example 12, except that p-nitrobenzyl(1R,5S,6S,8R,2'S,4'S)-2-(2-(3-allyloxycarbonyl-6-carbamoylphenylcarbamoyl)-1-(4-nitrobenzyloxycarbonyl)pyrrolidin-4-ylthio)-6-(1-hydroxyethyl)-1-methylcarbapenem-3-carboxylate was used. After the hydrogenation, the aqueous layer was freeze-dried to give (1R,5S,6S,8R,2'S,4'S)-2-(2-(3-carboxy-6-carbamoylphenylcarbamoyl)pyrrolidin-4-ylthio)-6-(1-hydroxyethyl)-1-methylcarbapenem-3-carboxylic acid. Nmr (DMSO-$d_6$+acetic acid-$d_4$): δ 1.3–1.38 (2×d, 6H); 2.0–2.11

(m, 1H); 2.85–2.96 (m, 1H); 3.09 (dd, 1H); 3.37 (dd, 1H); 3.53 (quintet, 1H); 3.79 (dd, 1H); 3.94 (t, 1H); 4.16 (t, 1H); 4.33 (dd, 1H); 4.43 (t, 1H); 7.87 (dd, 1H); 7.97 (d, 1H); 9.12 (d, 1H).

Ms (+ve FAB): 541 (Na salt), 563 (di-Na salt).

The starting material was prepared as follows:

Nitroterephthalic acid (6.33 g) in methylene chloride (75 ml) and THF (15 ml) was converted to the mono acid chloride using oxalyl chloride (2.63 ml), DMF (2.55 ml) and N-methylmorpholine (7.95 ml) at −10° C. After 1 hour the solvents were removed and, without further purification, the product was dissolved in allyl alcohol (20 ml) and THF (10 ml) and stirred overnight at ambient temperature. The solvents were removed and the residue partitioned between EtOAc and aqueous $NaHCO_3$. Acidification of the $NaHCO_3$ solution and extraction with EtOAc gave the product, 4-allyloxycarbonyl-2-nitrobenzoic acid (6.8 g). Nmr ($CDCl_3$): δ 4.89 (d, 2H); 5.31–5.49 (m, 2H); 5.95–6.15 (m, 1H); 7.94 (d, 1H); 8.36 (dd, 1H); 8.54 (d, 1H). Without purification, this acid was converted by the method above to the acid chloride which was dissolved in THF (100 ml) at 0° C. Ammonia gas was bubbled into the solution until the reaction was completed. The solution was partitioned between EtOAc and water, and the product from the organic fraction purified on silica, eluting with methylene chloride followed by EtOAc. The product (4 g), containing a small impurity, was reduced with $SnCl_2$ by a similar method to that in example 12 giving 4-allyloxycarbonyl-2-aminobenzamide. Nmr (DMSO-$d_6$): δ 4.79 (d, 2H); 5.22–5.46 (m, 2H); 5.91–6.13 (m, 1H); 7.02 (dd. 1H); 7.37 (d, 1H); 7.61 (d, 1H).

(2S,4S)-4-Acetylthio-1-(4-nitrobenzyloxycarbonyl)-2-carboxy-pyrrolidine (1.58 g) was converted to the acid chloride by suspension in methylene chloride (25 ml) and addition of oxalyl chloride (1.52 ml). A few drops of DMF were added. After 2 hours the solvents were evaporated and the acid chloride, dissolved in methylene chloride (10 ml), was added under argon to a solution of 4-allyloxycarbonyl-2-amino-benzamide (0.52 g) in THF (10 ml) and methylene chloride (5 ml) containing N-methylmorpholine (0.38 ml) at 0° C. The reaction was left overnight and partitioned between methylene chloride and dilute aqueous HCl. The methylene chloride fraction was washed with water, brine and dried. Purification was by silica chromatography, eluting with increasing concentrations of EtOAc in methylene chloride, giving (2S,4S)-4-acetylthio-1-(4-nitrobenzyloxycarbonyl)-2-(3-allyloxycarbonyl-6-carbamoylphenylcarbamoyl)pyrrolidine (0.84 g). Nmr ($CDCl_3$): δ 2.25 (quintet, 1H); 2.29 (s, 3H); 2.83 (m, 1H); 3.53 (dd, 1H); 4.02 (quintet, 1H); 4.2 (dd, 1H); 4.49 (dd, 1H); 4.85 (d, 2H); 5.23–5.46 (m, 2H); 5.97–6.13 (m, 1H); 7.31–7.5 (broad, 2H); 7.57 (d, 1H); 7.75 (dd, 1H); 7.81–7.95 (broad, 2H); 9.27 (d, 1H).

The thiol was generated from the above thioacetate by a similar method to that described in example 12.

A solution of 4-nitrobenzyl(1R,5R,6S,8R)-6-(1-hydroxyethyl)-1-methyl-2-diphenylphosphoryloxycarbapenem-3-carboxylate and (2S,4S)-1-(4-nitrobenzyloxycarbonyl)-2-(2-carbamoyl-5-allyloxycarbonylphenylcarbamoyl)pyrrolidin-4-ylthiol in acetonitrile (20 ml) were reacted as described in example 12, giving 4-nitrobenzyl(1R,5R,6S,8R,2'S,4'S)-2-(1-(4-nitrobenzyloxycarbonyl)-2-(3-allyloxy-3-carbonyl-6-carbamoylphenylcarbamoyl)pyrrolidin-4-ylthio)-6-(1-hydroxyethyl)-1-methylcarbapenem-3-carboxylate as a yellow foam (1.24 g). Nmr 1.23–1.35 (m, 6H); 2.2–2.38 (m, 1H); 2.77–2.93 (m, 1H); 3.27 (dd, 1H); 3.28–3.42 (m 1H); 3.65–3.92 (m, 2H); 4.17–4.35 (m, 3H); 4.53 (t, 1H); 4.83 (d, 2H); 4.92–5.44 (m, 6H); 5.93–6.11 (m, 1H); 6.22–6.58 (broad, 2H); 7.35–8.23 (complex pattern of doublets and double doublets, 10H); 9.20 (d, 1H).

EXAMPLE 15

The deprotection and purification were carried out by a similar method to that described in example 2 (chromatography of the final product was on an HP20SS column) except that allyl (1R,5S,6S,8R,2'S,4'S)-2-(1-allyloxycarbonyl-2-(2-dimethylaminocarbonyl-3-allyloxycarbonylphenylcarbamoyl)pyrrolidin-4-ylthio)-6-(1-hydroxyethyl)-1-methylcarbapenem-3-carboxylate was used. The appropriate aqueous fractions from the column were freeze-dried to give (1R,5S,6S,8R,2'S,4'S)-2-(2-(2-dimethylaminocarbonyl-3-carboxyphenylcarbamoyl)pyrrolidin-4-ylthio)-6-(1-hydroxyethyl)-1-methylcarbapenem-3-carboxylic acid. Nmr (DMSO-$d_6$+ acetic acid-$d_4$, mixture of rotamers): δ 1.17 (d, 6H); 1.75 (m, 2H); 2.65,2.72 (2×s, overlapping m, 4H); 3.00,3.01 (2×s, overlapping m, 4H); 3.17 (dd, 1H); 3.41 (quintet, 1H); 3.55 (m, 2H); 3.96 (m, 2H); 4.15 (dd, 1H); 7.43 (t, 1H); 7.68 (m, 1H); 8.20–8.40 (2×d, 1H).

The starting material was prepared as follows:

2-Dimethylaminocarbonyl-3-nitrobenzoic acid (1 g) was to the allyl ester by a similar method to that described in example 1 for the formation of allyl 3-allyloxy-5-aminobenzoate giving allyl 2-dimethylaminocarbonyl-3-nitrobenzoate (0.88 g). Nmr (DMSO-$d_6$): δ 2.45 (s, 3H); 2.97 (s, 3H); 4.79 (dd, 2H); 5.28–5.47 (m, 2H); 5.9–6.1 (m, 1H); 7.81 (t, 1H); 8.28–8.4 (dq, 2H).

Ms (CI): 279 $(MH)^+$

The allyl ester (0.44 g) was reduced with $SnCl_2$ by a similar method to the reduction described in example 1, giving allyl 2-dimethylaminocarbonyl-3-aminobenzoate (0.41 g) as a clear red oil. Nmr ($CDCl_3$): δ 2.24 (s, 3H); 3.06 (s, 3H); 3.64 (broad, 2H); 4.68 (dd, 2H); 5.17–5.37 (m, 2H): 5.82–6.02 (m, 1H); 6.83 (dd, 1H); 7.09–6.85 (m, 1H); 7.37 (dd, 1H).

Ms (CI): 249 $(MH)^+$

Allyl 2-dimethylaminocarbonyl-3-aminobenzoate (0.39 g, 1.4 mM) was condensed with (2S,4S)-4-acetylthio-1-alloxycarbonyl-2-carboxypyrrolidine (0.42 g, 1.54 mM) using a similar method to the EEDQ method described in example 12, giving (2S,4S)-1-allyloxycarbonyl-2-(2-dimethylaminocarbonyl-3-allyloxycarbonylphenylcarbamoyl)pyrrolidin-4-yl thioacetate (0.84 g). Nmr ($CDCl_3$, mixture of rotamers): δ 2.32 (s, 3H); 2.38 (br m, part obscured, 1H); 2.38 (br m, part obscured, 1H); 2.74,2.76 (2×s overlapping br m, 4H); 3.11, 3.14 (2×s, 3H); 3.36–3.45 (m, 1H); 3.98–4.14 (m, 2H); 4.50 (dd, 1H); 4.56–4.79 (m, 4H); 5.16–5.44 (m, 4H); 5.93–6.06 (m, 2H); 7.45 (t, 1H); 7.81–7.86 (m, 1H); 8.33–8.41 (2×d, 1H); 8.60 (br, 1H).

Ms (CI): 504 $(MH)^+$

The thiol was generated from the above thioacetate by a similar method to that described in example 12.

A solution of allyl(1R,5R,6S,8R)-6-(1-hydroxyethyl)-1-methyl-2-diphenylphosphoryloxycarbapenem-3-carboxylate (0.73 g, 1.47 mM) and (2S,4S)-1-allyloxycarbonyl)-2-(2-dimethylaminocarbonyl-3-allyloxycarbonylphenylcarbamoyl)pyrrolidin-4-ylthiol in acetonitrile (12 ml) were reacted by a similar method to that described in the 'preparation of protected carbapenem' step in example 1, giving allyl (1R,5R,6S,8R,2'S,4'S)-2-(1-allyloxycarbonyl-2-(2-dimethylaminocarbonyl-3-allyloxycarbonylphenylcarbamoyl)pyrrolidin-4-ylthio)-6-(1-hydroxyethyl)-1-methylcarbapenem-3-carboxylate as a white solid (0.63 g). Nmr (CDCl$_3$, mixture of rotamers): δ 1.24 (d, 3H); 1.35 (2×d, 3H); 1.98 (br, 1H); 2.34 (br, 1H); 2.73 (s, 3H); 3.11,3.13 (2×s, 3H); 3.22–3.46 (m, 3H); 3.66–3.85 (m, 1H); 4.00–4.26 (m, 3H); 4.50 (t, 1H); 4.62–4.80 (m, 6H); 5.08–5.46 (m, 6H); 5.83–6.06 (m, 3H); 7.46 (td, 1H); 7.86 (d, 1H); 8.29 (m, 1H); 8.55 (br, 1H).

Ms (CI): 711 (MH)$^+$

EXAMPLE 16

(1R,5S,6S,8R,2'S,4'S)-2-(2-(3-Carboxy-5-acetamidophenylcarbamoyl)pyrrolidin-4-ylthiol-6-(1-hydroxyethyl)-1-methylcarbapenem-3-carboxylic acid, dipotassium salt To a solution of 4-allyl(1R,5S,6S,8R,2'S,4'S)-2-(1-(4-nitrobenzyloxycarbonyl)-2-(3-carboxy-5-acetamidophenylcarbamoyl)pyrrolidin-4-ylthio)-6-(1-hydroxyethyl)-1-methylcarbapenem-3-carboxylate (0.4 g, 0.53 mmol) in DMF (20 ml) were added Meldrum's acid (0.2 g, 1.39 mmol) and tetrakis triphenylphosphine palladium (40 mg, 0.035 mmol). The reaction mixture was stirred for one hour, at ambient temperature. A solution of 1M potassium phosphate buffer (20 ml) and zinc powder (0.5 g) were added to the solution and after one hour, at ambient temperature, the reaction mixture was filtered over diatomaceous earth and the pH of the filtrate adjusted to 7.5 with solid potassium carbonate. The solution was filtered, concentrated under reduced pressure and the resulting residue purified by reverse phase chromatography (Nucleosil C18), with water as eluant, to give, after freeze drying, the title compound (78 mg, 28%). Nmr (DMSO-d6+acetic acid-d$_4$): δ 1.15 (d, 3H); 1.17 (d, 3H); 1.74 (m, 1H); 2.06 (s, 3H); 2.66 (m, 1H); 2.84 (m, 1H); 3.20 (dd, 1H); 3.40 (m, 2H); 3.70 (m, 1H); 3.97 (m, 2H); 4.16 (dd, 1H); 7.92 (s, 1H); 7.94 (s, 1H); 8.19 (s, 1H).

The starting material was prepared as follows:

A solution of (2S,4S)-4-acetylthio-2-carboxy-1-(4-nitrobenzyloxycarbonyl)pyrrolidine (1 g, 1.8 mmol) and EEDQ (0.53 g, 3 mmol) in chloroform (70 ml) was stirred at ambient temperature for 1 hour. 3-Acetamido-5-aminobenzoic acid (0.53 g, 2.7 mmol) and diisopropylethylamine (0.7 ml, 4 mmol) were then added to the reaction mixture, which was stirred for 2 hours, at ambient temperature. After evaporation of the solvent, the crude compound was purified by chromatography on HP20SS using methanol/water (80:20) as the eluant. Partial evaporation of the solvents and lyophilisation gave (2S,4S)-1-(4-nitrobenzyloxycarbonyl)-2-(3-carboxy-5-carbamoyl)pyrrolidin-4-ylthioacetate (1 g, 67%). (2S,4S)-1-(4-Nitrobenzyloxycarbonyl)-2-(3-carboxy-5-acetamidophenylcarbamoyl)pyrrolidin-4-ylthioacetate was dissolved in a mixture of methanol (60 ml) and water (20 ml) and the pH of the solution was adjusted to 11 with a 1M aqueous solution of NaOH. After 30 minutes at ambient temperature, the reaction mixture was neutralised with methanol, evaporated and purified by chromatography on HP20SS, using methanol/water (80:20) as the eluant. Evaporation and lyophilisation gave (2S,4S)-1-(4-nitrobenzyloxycarbonyl)-2-(3-carboxy-5-acetamidophenylcarbamoyl)pyrrolidin-4-ylthiol (0.68 g. 74%). Nmr (DMSOd$_6$+acetic acid-d$_4$): δ 2.05 (s, 3H); 2.05 (m, 1H); 2.75 (m, 1H); 3.20–3.80 (m, 2H); 4.00 (m, 1H); 4.42 (m, 1H); 5.40 (br s, 2H); 7.45–8.30 (m, 7H).

To a solution of 4-nitrobenzyl(1R,5S,6S,8R)-6-(1-hydroxyethyl)-1-methyl-2-diphenylphosphoryloxycarbapenem-3-carboxylate (0.6 g, 1.2 mmol) in DMF (12 ml) were added sequentially diisopropylethylamine (0.6 ml, 3.4 mmol), (2S,4S)-1-(4-nitrobenzyloxycarbonyl)-2-(3-carboxy-5-acetamidophenylcarbamoyl)pyrrolidin-4-ylthiol (0.6 g, 1.2 mmol), tri-n-butylphosphine (0.6 ml, 2.4 mmol) and water (0.1 ml, 5.5 mmol). The reaction mixture was stirred overnight, at 4° C., evaporated to dryness and the residue was purified by chromatography on HP20SS resin, using acetonitrile/water (40:60) as the eluant. Evaporation and lyophilisation gave allyl(1R,5R,6S,8R,2S',4'S)-2-(1-(4-nitrobenzyl-oxycarbonyl)-2-(3-carboxy-5-acetamidophenylcarbamoyl)pyrrolidin-4-ylthio)-6-(1-hydroxyethyl)-1-methylcarbapenem-3-carboxylate (0.8 g, 88%). Nmr (DMSO-d$_6$+acetic acid-d$_4$): δ 1.15 (d, 3H); 1.17 (d, 3H), 2.05 (s, 3H); 2.17 (m, 1H); 2.81 (m, 1H); 3.26 (dd, 1H); 3.36 (td, 1H); 4.56–4.74 (m, 2H); 5.02–5.73 (m, 4H); 5.91 (m, 1H); 7.47 (d, 1H); 7.68 (d, 1H); 7.85–7.99 (m, 3H); 8.20–8.29 (m, 2H).

EXAMPLE 17

(1R,5S,6S,8R,2'S,4'S)-2-(2-(4-Acetamido-3-carboxyphenylcarbamoyl)pyrrolidin-4-ylthio)-6-(1-hydroxyethyl)-1-methylcarbapenem-3-carboxylic acid, dipotassium salt The title compound was prepared from 4-allyl(1R,5S,6S, 8R, 2'S,4'S)-2-(1-(4-nitrobenzyloxycarbonyl)-2-(4-acetamido-3-carboxy-phenylcarbamoyl)pyrrolidin-4-ylthio)-6-(1-hydroxyethyl)-1-methylcarbapenem-3-carboxylate (diisopropylethylamine salt) using a similar method to that of example 16. Nmr (DMSO-d$_6$+acetic acid-d$_4$): δ 1.14 (d, 3H); 1.16 (d, 3H); 1.75 (m, 1H); 2.07 (s, 3H); 2.73 (m, 1H); 2.96 (dd, 1H); 3.21 (dd, 1H); 3.39 (m, 1H); 3.54 (dd, 1H); 3.78 (m, 1H); 3.96 (m, 1H); 4.08 (t, 1H); 4.18 (dd, 1H); 7.69 (dd, 1H); 8.18 (d, 1H); 8.42 (d, 1H).

MS (+ve FAB): 571 (MH)$^+$, (K salt)

The starting material was prepared as follows:

(2S,4S)-1-(4-Nitrobenzyloxycarbonyl)-2-(4-acetamido-3-carboxyphenylcarbamoyl)pyrrolidin-4-ylthioacetate was prepared from 2-acetamido-5-aminobenzoic acid using a similar method to that of example 16. Nmr (DMSO-d$_6$+ acetic acid-d$_4$): δ 1.95 (m, 1H); 2.12 (s, 3H); 2.34 (s, 3H); 2.77 (m, 1H); 3.32 (m, 1H); 3.93–4.50 (m, 3H); 5.04–5.32 (m, 2H); 7.47–8.42 (m, 7H).

(2S,4S)-1-(4-Nitrobenzyloxycarbonyl)-2-(4-acetamido-3-carboxyphenylcarbamoyl)pyrrolidin-4-ylthiol was prepared from (2S,4S)-1-(4-nitrobenzyloxycarbonyl)-2-(4-acetamido-3-carboxyphenylcarbamoyl)pyrrolidin-4-ylthioacetate using a similar method to that of example 16.

Allyl(1R,5R,6S,8R,2'S,4'S)-2-(1-(4-nitrobenzyloxycarbonyl)-2-(4-acetamido-3-carboxyphenylcarbamoyl)pyrrolidin-4-ylthio)-6-(1-hydroxyethyl)-1-methylcarbapenem-3-carboxylate (diisopropylethylamine salt) was prepared from (2S,4S)-1-(4-nitrobenzyloxycarbonyl)-2-(4-acetamido-3-carboxyphenylcarbamoyl)pyrrolidin-4-ylthiol and allyl (1R, 5R,6S,8R)-6-(1-hydroxyethyl)-1-methyl-2-diphenylphosphoryloxycarbapenem-3-carboxylate using a similar method to that of example 16. Nmr (CDCl$_3$) δ: 1.14–1.80 (m, 23H); 2.17 (s, 3H); 2.67 (m, 1H); 3.00–3.30 (m, 3H); 3.35–3.90 (m, 4H); 3.90–4.40 (m, 3H); 4.40–4.75 (m, 3H); 5.00–5.75 (m, 4H); 5.70–6.10 (m, 3H); 7.38–8.65 (m, 7H).

EXAMPLE 18

(1R,5S,6S,8R,2'S,4'S)-2-(2-(3-Carboxy-5-methylsulphonamidophenylcarbamoyl)pyrrolidin-4-ylthio)-6-(1-hydroxyethyl)-1-methylcarbapenem-3-carboxylic acid dipotassium salt The title compound was prepared from allyl (1R,5S,6S, 8R,2'S,4'S)-2-(1-(4-nitrobenzyloxycarbonyl)-2-(3-carboxy-5-methylsulphonamidophenylcarbamoyl)pyrrolidin-4-ylthio)-6-(1-hydroxyethyl)-1-methylcarbapenem 3-carboxylate using a similar method to that of example 16. Nmr (DMSOd$_6$+acetic acid-d$_4$): δ 1.16 (d, 3H); 1.17 (d, 3H); 1.74 (m, 1H); 2.64 (m, 1H); 2.81 (dd, 1H); 3.01 (s, 3H); 3.20 (m, 1H); 3.40 (m, 2H); 3.68 (m, 1H); 3.96 (m, 2H); 4.17 (dd, 1H); 7.54 (s, 1H); 7.82 (s, 1H); 8.00 (s, 1H).

MS (+ve FAB): 607 (M+H)$^+$ for monopotassium salt; 645 (M+H)$^+$ for dipotassium salt.

The starting material was prepared as follows:

(2S,4S)-1-(4-(Nitrobenzyloxycarbonyl)-2-(3-carboxy-5-methylsulphonamidophenylcarbamoyl)pyrrolidin-4-ylthioacetate was prepared from 3-amino-5-methylsulphonamidobenzoic acid using a similar method to that of example 16. Nmr (DMSO-d$_6$+acetic acid-d$_4$): δ 2.00 (m, 1H); 2.30 (s, 3H); 2.84 (m, 1H); 2.95 (s, 3H); 3.20–3.51 (m, 1H); 3.83–4.20 (m, 2H); 4.30–4.58 (m, 1H); 5.20 (m, 2H); 7.48–8.22 (m, 7H). (2S,4S)-1-(4-Nitrobenzyloxycarbonyl)-2-(3-carboxy-5-methylsulphonamidophenylcarbamoyl)pyrrolidin-4-ylthiol was prepared from (2S,4S)-1-(4-nitrobenzyloxycarbophenylcarbonyl)-2-(3-carboxy-5-methylsulphonamidophenylcarbamoyl)pyrrolidin-4-ylthioacetate using a similar method to that of example 16. Nmr (DMSO-d$_6$+acetic acid-d$_4$): δ 2.10 (m, 1H); 2.78 (m, 1H); 2.99 (s, 3H); 3.43 (m, 1H); 3.68 (m, 1H); 4.05 (m, 1H); 4.42 (m, 1H); 5.13–5.32 (m, 3H); 7.50–8.82 (m, 7H).

Allyl(1R,5R,6S,8R,2'S,4'S)-2-(1-(4-nitrobenzyloxycarbonyl)-2-(3-carboxy-5-methylsulphonamidophenylcarbamoyl)pyrrolidin-4-ylthio)-6-(1-hydroxyethyl)-1-methylcarbapenem-3-carboxylate was prepared from (2S,4S)-1-(4-nitrobenzyloxycarbonyl)-2-(3-carboxy-5-methylsulphonamidophenylcarbamoyl)pyrrolidin-4-ylthio and allyl(1R,5R,6S,8R)-6-(1-hydroxethyl)-1-methyl-2-diphenylphosphoryloxycarbapenem-3-carboxylate using a similar method to that of example 16. Nmr (DMSO-d$_6$+ acetic acid-d$_4$): δ 1.20 (d, 3H); 1.22 (d, 3H); 1.96 (m, 1H); 2.83 (m, 1H); 3.00 (s, 3H); 2.26–3.57 (m, 3H); 3.87–4.28 (m, 4H); 4.42–4.76 (m, 3H); 5.08–5.42 (m, 4H); 5.92 (m, 1H); 7.22–8.22 (m, 7H).

EXAMPLE 19

(1R,5S,6S,8R,2'S,4'S)-2-(2-(3-Carboxy-5-sulphophenylcarbamoyl)pyrrolidin-4-ylthio)-6-(1-hydroxyethyl)-1-methylcarbapenem-3-carboxylic acid, disodium salt To a stirred solution of 4-nitrobenzyl(1R,5S,6S,8R,2'S,4'S)-2-(1-(4-nitrobenzyloxycarbonyl)-2-(3-carboxy-5-sulphophenylcarbamoyl)pyrrolidin-4-ylthio)-6-(1-hydroxyethyl)-1-methylcarbapenem-3-carboxylate (0.5 g, 0.56 mmol) in DMF (5 ml) and water (5 ml) was added a solution of 1M sodium phosphate buffer (5 ml) followed by zinc powder (1 g). The reaction mixture was stirred for 1 hour and the pH of the solution was adjusted to 8 by adding a saturated aqueous solution of sodium hydrogen carbonate. After filtration over diatomaceous earth, the filtrate was concentrated and purified by subjecting to preparative chromatography (Nucleosil C-18), using water as the eluant. Concentration and lyophilisation of the required fractions gave the title compound (44 mg, 12%). Nmr (DMSO-d$_6$+ acetic acid-d$_4$): δ 1.15 (d, 3H); 1.16 (d, 3H); 1.78 (m, 1H); 2.73 (m, 1H); 2.92 (m, 1H); 3.21 (dd, 1H); 3.40 (m, 1H); 3.48 (m, 1H); 3.75 (m, 1H); 3.97 (m, 1H); 4.03 (m, 1H); 4.18 (m, 1H); 7.93 (s, 1H); 8.11 (s, 1H); 8.29 (s, 1H).

MS (–ve FAB): 576 (M–H)$^-$ for monosodium salt; 598 (M–H)$^-$ for disodium salt.

The starting material was prepared as follows:

(2S,4S)-1-(4-Nitrobenzyloxycarbonyl)-2-(3-carboxy-5-sulphophenylcarbamoyl)pyrrolidin-4-ylthioacetate was prepared from 3-amino-5-sulphobenzoic acid using a similar method to that of example 16. Nmr (DMSO-d$_6$+acetic acid-d$_4$): δ 1.97 (m, 1H); 2.30 (s, 3H); 2.80 (m, 1H); 3.37 (m, 1H); 3.86–4.15 (m, 2H); 4.46 (m, 1H); 5.05–5.28 (m, 2H); 7.46–9.25 (m, 7H).

(2S,4S)-1-(4-Nitrobenzyloxycarbonyl)-2-(3-carboxy-5-sulphophenylcarbamoyl)pyrrolidin-4-ylthiol was prepared from (2S,4S)-1-(4-nitrobenzyloxycarbonyl)-2-(3-carboxy-5-sulphophenylcarbamoyl)pyrrolidin-4-ylthioacetate using a similar method to that of example 16. Nmr (DMSO-d$_6$+ acetic acid-d$_4$): δ 1.25 (d, 3H); 1.27 (d, 3H); 2.07 (m, 1H); 2.70 (m, 1H); 3.4 (m, 1H); 3.67 (m, 1H); 3.99 (m, 1H); 4.49 (m, 1H); 5.07–5.30 (m, 2H); 7.47–8.40 (m, 7H).

4-Nitrobenzyl(1R,5S,6S,8R,2'S,4'S)-2-(1-(4-nitrobenzyloxycarbonyl)-2-(3-carboxy-5-sulphophenylcarbamoyl)pyrrolidin-4-ylthio)-6-(1-hydroxyethyl)-1-methylcarbapenem-3-carboxylate was prepared from (2S,4S)-1-(4-nitrobenzyloxycarbonyl)-2-(3-carboxy-5-sulphophenylcarbamoyl)pyrrolidin-4-ylthiol and 4-nitrobenzyl(1R,5R,6S,8R)-6-(1-hydroxyethyl)-1-methyl-2-diphenylphosphoryloxycarbapenem-3-carboxylate using a similar method to that of example 1. Nmr (DMSO-d$_6$+acetic acid-d$_4$): δ 1.20 (d, 3H); 1.21 (d, 3H); 1.96 (m, 1H): 2.77 (m, 1H); 3.18–3.47 (m, 2H); 3.66–4.90 (m, 6H); 5.04–5.50 (m, 4H); 7.30–8.35 (m, 11H).

EXAMPLE 20

(5R,6S,8R,2'S,4'S)-2-(2-(3-Carboxyphenylcarbamoyl)pyrrolidin-4-ylthio)-6-(1-hydroxyethyl)carbapenem-3-carboxylic acid, disodium salt.

To a stirred solution of allyl(5R,6S,8R,4'S)-2-(1-allyloxycarbonyl)-2-(3-allyloxycarbonylphenylcarbamoyl)-pyrrolidin-4-ylthio)-6-(1-hydroxyethyl)carbapenem-3-carboxylate (0.185 g, 0.296 mmol) in CH$_2$Cl$_2$ (4 ml), at ambient temperature, were added sequentially N-methylaniline (0.190 g, 1.776 mmol), water (4 ml), sodium bicarbonate (100 mg) and tetrakis (triphenylphosphine)palladium (34 mg, 0.029 mmol). After 10 minutes the aqueous phase was separated and injected onto a C18 preparative HLPC column giving the title compound (43 mg, 27%). Nmr (DMSO-d$_6$+acetic acid-d$_4$): 1.16 (d, 3H); 1.81 (m, 1H); 2.64 (m, 1H); 2.84 (m, 1H); 3.26 (m, 3H); 3.4 (m, 1H); 3.67 (m, 1H); 3.94 (m, 2H); 4.12 (m, 1H); 7.42 (t, 1H); 7.65 (d, 1H); 7.83 (d, 1H); 8.27 (s, 1H).

The starting allyl(5R,6S,8R,2'S,4'S)-2-(1-allyloxycarbonyl-2-(3-allyloxycarbonylphenylcarbamoyl)pyrrolidin-4-yl-thio)-6-(1-hydroxyethyl)carbapenem-3-carboxylate was prepared in 67% yield using a similar procedure to that described in example 1, by reacting (2S,4S) 1-allyloxycarbonyl-2-(3-allyloxycarbonylphenyl-carbamoyl)pyrrolidine-4-thiol, described in example 4, with allyl (5R,6S,8R)-6-(1-hydroxyethyl)-2-diphenylphosphoryloxycarbapenem-3-carboxylate (EP-A-126780 and EP-A-208889).

EXAMPLE 21

(1R,5S,6S,8R,2'S,4'S)-2-(2-(3-Carboxy-5-cyanophenylcarbamoylpyrrolidin-4-ylthio)-6-(1-hydroxyethyl)-1-methylcarbapenem-3-carboxylic acid, disodium salt To a solution of allyl(1R,5S,6S,8R,2'S,4'S)-2-(1-allyloxycarbonyl-2-(3-allyloxycarbonyl-5-cyanophenylcarbamoyl)pyrrolidin-4-yl-thio)-6-(1-hydroxyethyl)-1-methylcarbapenem-3-carboxylate (358 mg, 0.54 mM) and 2,2-dimethyl-1,3-dioxane-4,6-dione (388 mg, 2.7 mm) in a mixture of DMF (8 ml) and THF (4 ml), under an argon atmosphere, was added tetrakis (triphenylphosphine)palladium (62 mg, 0.054 mM). The solution was stirred, under argon with protection from light, for 1.75 hours, and solvent removed by evaporation. The residue was dissolved in a mixture of THF (6 ml) and DHF (2 ml), and a solution of sodium 2-ethylhexanoate (295 mg, 1.77 mM) in THF (4 ml) was added, followed by diethyl ether (20 ml). The resultant precipitate was centrifuged, and supernatant removed. The product was washed twice by resuspension in a mixture of THF (4 ml) and diethyl ether (10 ml), then diethyl ether (20 ml) followed by centrifugation. Crude product was dissolved in water (20 ml) and the pH adjusted to 7.4 with $NaHCO_3$. After filtration, the solution was chromatographed on HP20SS resin, and fractions combined as appropriate to give the title product (206 mg, 70%). Nmr (DMSO-$d_6$+acetic acid-$d_4$): δ 1.17 (d, 6H); 1.95 (m, part obscured, 1H); 2.83 (m, 1H); 3.09 (dd, 1H); 3.25 (dd, 1H); 3.41 (quintet, 1H); 3.64 (dd, 1H); 3.88 (quintet, 1H); 4.02 (quintet, 1H); 4.22 (dd, 1H); 4.31 (t, 1H); 8.00 (s, 1H); 8.28 (t, 1H); 8.46 (t, 1H).

Ms (+ve FAB): 523 (MH)$^+$, (Na salt)

The starting materials were prepared as follows:
3-Cyano-5-nitrobenzoic acid

3-Amino-5-nitrobenzoic acid (3.64 g, 20 mM) was dissolved in concentrated hydrochloric acid (20 ml), diluted with water (75 ml), cooled to 0°, and added over 30 minutes to a solution of $NaNO_2$ (1.38 g, 20 mM) in water (10 ml). The pH was adjusted to 6.2 with saturated $Na_2CO_3$ solution. A mixture of $CuSO_4.5H_2O$ (10 g, 42 mM) in water (40 ml) and KCN (10 g, 154 mM) in water (20 ml) was heated to 65°, the solution of diazonium salt added over 15 minutes, and the mixture refluxed for 40 minutes. After cooling, and acidifying with 2M hydrochloric acid, the organics were extracted into ethyl acetate (2×200 ml). The combined extracts were washed with aqueous $NaH_2PO_4$, water, brine, and dried over $Na_2SO_4$. Evaporation gave 3-cyano-5-nitrobenzoic acid (3.6 g, 94%).

Nmr (DMSO-$d_6$): δ 8.69 (t, 1H); 8.80 (t, 1H); 8.97 (t, 1H).
Ms (−ve FAB): 191 (M−H)$^−$
Ir (nujol): ν 2220 cm$^{-1}$ 3-Cyano-5-nitrobenzoic acid was allylated essentially as in Example 1, except that the chromatographic purification used a mixture of petrol/ethyl acetate (5:1), to give allyl 3-cyano-5-nitrobenzoate. Nmr (DMSO-$d_6$): δ 4.91 (dt, 2H); 5.39–5.53 (m, 2H); 5.99–6.19 (m, 1H); 8.78 (t, 1H); 8.81 (t, 1H); 9.04 (t, 1H).

Ms (+ve FAB): 202 M$^+$; 232 (M+NH$_4$)$^+$; (both for amino compound by ammonia reduction)

Reduction of the above nitro compound by the method of Example 1 gave allyl 3-amino-5-cyanobenzoate, mp 112°–113°. Nmr (DHSO-$d_6$): δ 4.79 (dt, 2H); 5.25–5.45 (m, 2H); 5.94–6.13 (m overlapping br, 1H); 7.10 (t, 1H); 7.37 (t, 1H); 7.48 (t, 1H).

Ms (+ve FAB): 202 M$^+$; 232 (M+NH$_4$)$^+$

The above amine was condensed with proline acid as Example 1, purifying by chromatography using a gradient of dichloromethane/ethyl acetate (19:1 to 9:1) to give (2S,4S)-1-allyloxycarbonyl-2-(3-allyloxycarbonyl-5-cyanophenylcarbamoyl)pyrrolidin-4-ylthioacetate. Nmr (CDCl$_3$): δ 2.33 (s, 3H); 2.59 (br, 2H); 3.38 (dd, 1H); 3.97–4.17 (m, 2H); 4.56 (t, 1H); 4.69 (d, 2H); 4.84 (d, 2H); 5.26–5.48 (m, 4H); 5.85–6.14 (m, 2H); 8.03 (br s, 1H); 8.18 (t, 1H); 8.29 (br s, 1H); 9.69 (br, 1H).

Ms (+ve FAB): 458 (MH)$^+$; 480 (M+Na)$^+$

The above thioacetate was deacetylated as Example 1, to give (2S,4S)-1-allyloxycarbonyl-2-(3-allyloxycarbonyl-5-cyanophenylcarbamoyl)pyrrolidin-4-ylthiol. Nmr (CDCl$_3$): δ 1.90 (d, 1H); 2.52 (br, 1H); 2.65 (br, 1H); 3.34–3.52 (m, 2H); 4.07 (dd, 1H); 4.54 (t, 1H); 4.69 (d, 2H); 4.84 (d, 2H); 5.27–5.47 (m, 4H); 5.87–6.11 (m, 2H); 8.01 (s, 1H); 8.21 (t, 1H); 8.28 (s, 1H); 9.56 (br, 1H).

The above thiol was condensed with carbapenem phosphate as Example 1, purifying by chromatography using a gradient of dichloromethane/ethyl acetate (3:2 to 2:3) to give allyl(1R,5S,6S,8R,2'S,4'S)-2-(1-allyloxycarbonyl-2-(3-allyloxycarbonyl-5-cyanophenylcarbamoyl)pyrrolidin-4-ylthio)-6-(1-hydroxyethyl)-1-methylcarbapenem-3-carboxylate. Nmr (CDCl$_3$): δ 1.27 (d, 3H); 1.35 (d, 3H); 2.67 (v br, 2H); 3.21–3.33 (overlapping m, 2H); 3.53 (br, 1H); 3.83 (quintet, 1H); 3.93 (dd, 1H); 4.20–4.31 (overlapping m, 2H); 4.54 (t, 1H); 4.63–4.86 (m, 6H); 5.21–5.47 (m, 6H); 5.82–6.11 (m overlapping br, 3H); 8.05 (t, 1H); 8.33 (br s, 1H); 8.37 (br s, 1H); 9.35 (br, 1H).

Ms (+ve FAB): 665 (MH)$^+$; 687 (M+Na)$^+$

EXAMPLE 22

(1R,5S,6S,8R,2'S,4'S)-2-(2-(3-Carboxy-5-methoxyphenylcarbamoyl)pyrrolidin-4-ylthio)-6-(1-hydroxyethyl)-1-methylcarbapenem-3-carboxylic acid, disodium salt was prepared using the technique of Example 21. Nmr (DMSO-$d_6$+acetic acid-$d_4$): δ 1.17 (d, 3H); 1.18 (d, 3H); 1.83 (m, part obscured, 1H); 2.76 (quintet, 1H); 2.98 (dd, 1H); 3.22 (dd, 1H); 3.39 (quintet, 1H); 3.56 (dd, 1H); 3.81 (s overlapping m, 4H); 4.00 (quintet, 1H); 4.15,4.18 (t overlapping dd, 2H); 7.22 (t, 1H); 7.58 (t, 1H); 7.84 (t, 1H).

Ms (−ve FAB): 505 (M−H)$^+$, (Na salt)

The starting materials were prepared as follows:

3-Hydroxy-5-nitrobenzoic acid was methylated essentially as the allylation step of Example 1, except that the allyl bromide was replaced by dimethyl sulfate, and purification by chromatography was unnecessary, to give methyl 3-methoxy-5-nitrobenzoate. Nmr (CDCl$_3$): δ 3.94 (s, 3H); 3.97 (s, 3H); 7.87 (t, 1H); 7.90 (t, 1H); 8.44 (t, 1H).

The above ester (3.45 g, 16 mM) was dissolved in THF (100 ml), treated with 1M NaOH (25 ml), and stirred at ambient temperature for 5 hours. After removal of the solvent, the residue was treated with water (50 ml), acidified with 2M sulfuric acid, and extracted with ethyl acetate (3×60 ml). The combined organic extracts were washed with aqueous $NaH_2PO_4$, brine, and dried over $NgSO_4$. Evaporation gave 3-methoxy-5-nitrobenzoic acid, which was allylated essentially as in Example 1, except that the chromatographic purification used a mixture of petrol/ethyl acetate (6:1), to give allyl 3-methoxy-5-nitrobenzoate. Nmr (CDCl$_3$): δ 3.95 (s, 3H); 4.87 (dt, 2H); 5.31–5.48 (m, 2H); 5.95–6.15 (m, 1H); 7.89 (t, 1H); 7.92 (t, 1H); 8.46 (t, 1H).

Ms (CI): 237 M$^+$; 255 (M+NH$_4$)$^+$

Reduction of the above nitro compound by the method of Example 1 gave allyl 3-amino-5-methoxybenzoate. Nmr (DMSO-$d_6$): δ 3.72 (s, 3H); 4.50 (v br, 2H); 4.75 (dt, 2H); 5.25–5.43 (m, 2H); 5.95–6.11 (m, 1H); 6.47 (t, 1H); 6.75 (t, 1H); 6.93 (t, 1H).

Ms (CI): 208 (MH)$^+$

The above amine was condensed with proline acid as Example 1, purifying by chromatography using a gradient of petrol/ethyl acetate (5:2 to 2:1) to give (2S,4S)-1-allyloxycarbonyl-2-(3-allyloxycarbonyl-5-methoxyphenylcarbamoyl)pyrrolidin-4-ylthioacetate. Nmr (CDCl$_3$): δ 2.32 (s, 3H); 2.59 (br, 2H); 3.38 (dd, 1H); 3.85 (s, 3H); 4.02 (quintet, 1H); 4.15 (dd, 1H); 4.55 (t, 1H); 4.68 (d, 2H); 4.81 (d, 2H); 5.22–5.46 (m, 4H); 5.83–6.13 (m, 2H); 7.35 (t, 1H); 7.58 (br s, 1H); 7.64 (t, 1H); 9.12 (br, 1H).

Ms (+ve FAB): 463 (MH)$^+$; 485 (M+Na)$^+$

The above thioacetate was deacetylated and condensed with carbapenem phosphate as Example 1, purifying by chromatography using a gradient of dichloromethane/ethyl acetate (60:40 to 45:55) to give allyl(1R,5S,6S,8R,2'S,4'S)-2-(1-allyloxycarbonyl-2-(3-allyloxycarbonyl-5-methoxyphenylcarbamoyl)pyrrolidin-4-ylthio)-6-(1-hydroxyethyl)-1-methylcarbapenem-3-carboxylate. Nmr (CDCl$_3$): δ 1.25 (d, 3H); 1.37 (d, 3H); 2.64 (v br, 2H); 3.21–3.33 (overlapping m, 2H); 3.48 (br, 1H); 3.80 (quintet, 1H); 3.85 (s, 3H); 4.01 (dd, 1H); 4.19–4.29 (overlapping m, 2H); 4.53 (t, 1H); 4.62–4.83 (m, 6H); 5.20–5.45 (m, 6H); 5.84–6.11 (m overlapping br, 3H); 7.25 (t, 1H); 7.63 (m, 2H); 8.90 (br, 1H).

Ms (+ve FAB): 670 (MH)$^+$; 692 (M+Na)$^+$

EXAMPLE 23

(1R,5S,6S,8R,2'S,4'S)-2-(2-(5-Carboxy-2-methanesulphinylphenylcarbamoyl)pyrrolidin-4-yl-thio)-6-(1-hydroxyethyl)-1-methylcarbapenem-3-carboxylic acid, disodium salt was prepared as a mixture of diastereoisomers at the sulfoxide centre, using the technique of Example 21. Nmr (DHSO-$d_6$+acetic acid-$d_4$): δ 1.18 (d, 6H); 1.87 (m, part obscured, 1H); 2.64–2.91, 2.82, 2.84 (m overlapping 2×s, 5H); 3.21 (dd, 1H); 3.40 (quintet, 1H); 3.52 (dd, 1H); 3.71 (quintet, 1H); 4.01 (quintet, 1H); 4.01 (m, 1H); 4.18 (dd, 1H); 7.83 (t, 1H); 7.94 (td, 1H); 8.45 (d, 1H).

Ms (+ve FAB): 560 (MH)$^+$, (Na salt); 582 (MH)$^+$, (Na$_2$ salt)

The starting materials were prepared as follows:
4-Methanesulphinyl-3-nitrobenzoic acid 4-Methylthio-3-nitrobenzoic acid (4.36 g, 20 mM) was dissolved in acetic acid (200 ml), and treated at ambient temperature with H$_2$O$_2$ (2.5 ml, 30%, 22 mM). After stirring at ambient temperature for 4 days, excess peroxide was decomposed with sodium metabisulfite, and solvent evaporated. The residue was purified by chromatography on silica, eluting with methanol, to give 4-methanesulphinyl-3-nitrobenzoic acid (4.1 g, 89%), mp 238°–239°. Nmr (DMSO-$d_6$): δ 2.90 (s, 3H); 8.29 (d, 1H); 8.56 (dd, 1H); 8.68 (d, 1H).

Ms (-ve FAB): 229 (M-H)$^-$

The above acid was allylated essentially as in Example 1, except that the chromatographic purification was unnecessary, to give allyl 4-methanesulphinyl-3-nitrobenzoate, mp 119–121°. Nmr (DMSO-$d_6$): δ 2.91 (s, 3H); 4.91 (dt, 2H); 5.29–5.50 (m, 2H); 5.99–6.18 (m, 1H); 8.34 (d, 1H); 8.61 (dd, 1H); 8.69 (d, 1H).

Reduction of the above nitro compound by the method of Example 1 gave allyl 3-amino-4-methanesulphinylbenzoate. Nmr (CDCl$_3$): δ 2.92 (s, 3H); 4.82 (dt, 2H); 5.17 (br, 2H); 5.28–5.46 (m, 2H); 5.96–6.11 (m, 1H); 7.30 (dd, 1H); 7.41 (m, 2H).

Ms (EI): 223 (M-O)$^+$; 239 M$^+$

The above amine was condensed with proline acid as Example 1, purifying by chromatography using a gradient of hexane/ethyl acetate (3:2 to 1:1) to give (2S,4S)-1-allyloxycarbonyl-2-(5-allyloxycarbonyl-2-methanesulphinylphenylcarbamoyl)pyrrolidin-4-ylthioacetate. Nmr (DMSO-$d_6$ at 100°): δ 1.98 (m, 1H); 2.32 (s, 3H); 2.73 (s, 3H); 2.86 (m, part obscured, 1H); 3.36 (m, 1H); 3.91–4.10 (overlapping m, 2H); 4.48 (dd, 1H); 4.53 (m, 2H); 4.86 (d, 2H); 5.11–5.49 (m, 4H); 5.80–5.97 (m, 1H); 6.01–6.15 (m, 1H); 8.09 (s, 2H); 8.35 (s, 1H).

Ms (+ve FAB): 495 (MH)$^+$

The above thioacetate was deacetylated and condensed with carbapenem phosphate as Example 1, purifying by chromatography using a gradient from ethyl acetate to ethyl acetate/isopropanol (98:2) to give allyl(1R,5S,6S,8R,2'S,4'S)-2-(1-allyloxycarbonyl-2-(5-allyloxycarbonyl-2-methanesulphinylphenylcarbamoyl)pyrrolidin-4-ylthio)-6-(1-hydroxyethyl)-1-methylcarbapenem-3-carboxylate. Nmr (DMSO-$d_6$, mixture of rotamers): δ 1.18 (d, 6H); 1.99 (br, 1H); 2.80 (s overlapping m, 5H); 3.25 (solvent overlapping m, 2H); 3.54 (m, 1H); 3.90–4.18 (m, 3H); 4.15 (dd, 1H); 4.55 (m, 4H); 4.85 (d, 2H); 5.06 (d, 1H); 5.14–5.46 (m, 6H); 5.79–6.13 (m, 3H); 7.80–8.05 (m, 2H); 8.12 (m, 1H); 10.10 (m, 1H).

Ms (+ve FAB): 702 (MH)$^+$

EXAMPLE 24

(1R,5S,6S,8R,2'S,4'S)-2-(2-(3-Carboxy-5-methanesulphonylphenylcarbamoyl)pyrrolidin-4-ylthio)-6-(1-hydroxyethyl)-1-methylcarbapenem-3-carboxylic acid, disodium salt was prepared using the technique of Example 21. Nmr (DMSO-$d_6$+acetic acid-$d_4$): δ 1.16 (d, 3H); 1.18 (d, 3H); 1.75 (quintet, 1H); 2.63 (m, 1H); 2.79 (dd, 1H); 3.20 (s overlapping m, 4H); 3.38 (m, 2H); 3.64 (quintet, 1H); 3.95 (m, 2H); 4.14 (dd, 1H); 8.09 (t, 1H); 8.44 (m, 2H).

Ms (-ve FAB): 574 (M-H)$^-$, (Na salt)

The starting materials were prepared as follows:
3-Methylthio-5-nitrobenzoic acid 3-Amino-5-nitrobenzoic acid (1.82 g, 10 mM) was dissolved in concentrated sulphuric acid (1.9 ml), diluted with water (10ml), and cooled to 5°. A solution of NaNO$_2$ (0.7 g, 10 mM) in water (3 ml) was added and the mixture stirred for 30 minutes. The cold solution of diazonium salt was added to a slurry of thiomethylcopper(I) at 3°, and the mixture stirred for 45 minutes. Organics were extracted into ethyl acetate (5×60 ml), and the combined organic layers washed with aqueous NaH$_2$PO$_4$, water, brine, and dried over Na$_2$SO$_4$. Evaporation gave 3-methylthio-5-nitrobenzoic acid (1.77 g, 83%). Nmr (DMSO-$d_6$): δ 2.63 (s, 3H); 8.10 (t, 1H); 8.21 (t, 1H); 8.32 (t, 1H); 13.68 (br, 1H).

Ms (-ve FAB): 213 (M-H)$^-$

The above acid was allylated essentially as in Example 1, except that the chromatography eluant was a mixture of petrol/ethyl acetate (6:1), to give allyl 3-methylthio-5-nitrobenzoate. Nmr (CDCl$_3$): δ 2.60 (s, 3H); 4.87 (dt, 2H); 5.32–5.49 (m, 2H); 5.93–6.07 (m, 1H); 8.20 (m, 2H); 8.57 (t, 1H).

Ms (EI): 253 M$^+$

Allyl 3-methylsulphonyl-5-nitrobenzoate

Allyl 3-methylthio-5-nitrobenzoate (1.12 g, 4.4 mM) was dissolved in methanol (30 ml), and cooled to 2°. A solution of "potassium peroxymonopersulfate" (2KHSO$_5$.KHSO$_4$.K$_2$SO$_4$, 8.13 g, 13.2 mM) in water (25 ml) was added slowly, and stirring continued for 4 hours. The mixture was diluted with water (60 ml) and extracted with ethyl acetate (3×100 ml). The combined organic extracts were washed with water, brine, and dried over Na$_2$SO$_4$. Crude product was purified by chromatography on silica using a gradient of petrol/ethyl acetate (3:1 to 2:1) to give allyl 3-methylsulphonyl-5-nitrobenzoate (0.74 g, 59%). Nmr (DMSO-d$_6$): δ 3.44 (s, 3H); 4.94 (dt, 2H); 5.32–5.53 (m, 2H); 6.01–6.25 (m, 1H); 8.78 (t, 1H); 8.89 (t, 1H); 8.91 (t, 1H).

Reduction of the above nitro compound by the method of Example 1 gave allyl 3-amino-5-methanesulphonylbenzoate. Nmr (DMSO-d$_6$): δ 3.15 (s, 3H); 4.80 (dt, 2H); 5.26–5.47 (m, 2H); 5.95–6.15 (m overlapping br, 3H); 7.29 (t, 1H); 7.47 (t, 1H); 7.51 (t, 1H).

The above amine was condensed with proline acid as Example 1, purifying by chromatography using a gradient of hexane/ethyl acetate (2:1 to 1:1) to give (2S,4S)-1-allyloxycarbonyl-2-(3-allyloxycarbonyl-5-methanesulphonylphenylcarbamoyl)pyrrolidin-4-ylthioacetate. Nmr (CDCl$_3$): δ 2.34 (s, 3H); 2.48 (m, 1H); 2.62 (m, 1H); 3.17 (s, 3H); 3.41 (dd, 1H); 4.03 (quintet, 1H); 4.15 (dd, 1H); 4.58 (dd, 1H); 4.71 (d, 2H); 4.84 (dt, 2H); 5.27–5.47 (m, 4H); 5.88–6.14 (m, 2H); 8.23 (br s, 2H); 8.37 (t, 1H); 9.69 (br, 1H).

Ms (+ve FAB): 511 (MH)$^+$; 533 (M+Na)$^+$

The above thioacetate was deacetylated and condensed with carbapenem phosphate as Example 1, purifying by chromatography using a gradient of dichloromethane/ethyl acetate (55:45 to 20:80) to give allyl(1R,5S,6S,8R,2'S,4'S)-2-(1-allyloxycarbonyl-2-(3-allyloxycarbonyl-5-methanesulphonylphenylcarbamoyl)pyrrolidin-4-ylthio)-6-(1-hydroxyethyl)-1-methylcarbapenem-3-carboxylate. Nmr (CDCl$_3$): δ 1.24 (d, 3H); 1.36 (d, 3H); 2.54 (br, 1H); 2.66 (br, 1H); 3.12 (s, 3H); 3.19–3.22 (overlapping m, 2H); 3.54 (br, 1H); 3.87 (quintet, 1H); 3.94 (dd, 1H); 4.25,4.29 (quintet overlapping dd, 2H); 4.55 (t, 1H); 4.65–4.80 (m, 4H); 4.85 (d, 2H); 5.20–5.46 (m, 6H); 5.86–6.12 (m, overlapping br, 3H); 8.31 (br, 1H); 8.43 (br, 1H); 8.52 (br, 1H); 9.40 (br, 1H).

Ms (+ve FAB): 718 (MH)$^+$; 740 (M+Na)$^+$

EXAMPLE 25

(1R,5S,6S,8R,2'S,4'S)-2-(2-(3-Carboxy-5-trifluoromethylphenylcarbamoyl)pyrrolidin-4-ylthio)-6-(1-hydroxyethyl)-1-methylcarbapenem-3-carboxylic acid, disodium salt was prepared using the technique of Example 2. Nmr (DMSO-d$_6$+acetic acid-d$_4$): δ 1.16 (d, 6H); 1.92 (m, part obscured, 1H); 2.77 (m, part obscured, 1H); 3.00 (dd, 1H); 3.21 (dd, 1H); 3.37 (quintet, 1H); 3.59 (quintet, 1H); 3.80 (quintet, 1H); 3.97 (quintet, 1H); 4.20 (m, 2H); 7.91 (br s, 1H); 8.27 (br s, 1H); 8.44 (br s, 1H).

Ms (−ve FAB): 542 (M−H)$^+$, (acid); 564 (M−H)$^−$, (Na salt)

The starting materials were prepared as follows:

3-Nitro-5-trifluoromethylbenzoic acid was allylated essentially as in Example 1, except that the product was sufficiently pure for use without chromatography, to give allyl 3-nitro-5-trifluoromethylbenzoate. Nmr (DMSO-d$_6$): δ 4.91 (dt, 2H); 5.30–5.51 (m, 2H); 5.99–6.20 (m, 1H); 8.58 (br s, 1H); 8.77 (br s, 1H); 8.84 (t, 1H).

Ms (CI): 275 M$^+$; 293 (M+NH$_4$)$^+$

Reduction of the above nitro compound by the method of Example 2 gave allyl 3-amino-5-trifluoromethylbenzoate, sufficiently pure for use without chromatography. Nmr (DMSO-d$_6$): δ 4.78 (dt, 2H); 5.24–5.43 (m, 2H); 5.93–6.13 (m, 1H); 7.08 (t, 1H); 7.27 (br s, 1H); 7.44 (t, 1H).

Ms (CI): 245 M$^+$; 263 (M+NH$_4$)$^+$

The above amine was condensed with proline acid as Example 1, purifying by chromatography using a gradient from dichloromethane to dichloromethane/diethyl ether (9:1) to give (2S,4S)-1-allyloxycarbonyl-2-(3-allyloxycarbonyl-5-trifluoromethylphenylcarbamoyl)pyrrolidin-4-ylthioacetate. Nmr (CDCl$_3$): δ 2.33 (s, 3H); 2.59 (m, 2H); 3.39 (dd, 1H); 4.04 (quintet, 1H); 4.14 (dd, 1H); 4.58 (t, 1H); 4.62 (dt, 2H); 4.85 (dt, 2H); 5.23–5.48 (m, 4H); 5.84–6.15 (m, 2H); 8.03 (br s, 1H); 8.23 (br s, 2H); 9.60 (br, 1H).

Ms (+ve FAB): 501 (MH)$^+$; 523 (M+Na)$^+$

The above thioacetate was deacetylated and condensed with carbapenem phosphate as Example 1, purifying by chromatography using a gradient from dichloromethane to ethyl acetate/dichloromethane (9:1) to give allyl(1R,5S,6S,8R,2'S,4'S)-2-(1-allyloxycarbonyl-2-(3-allyloxycarbonyl-5-trifluoromethylphenylcarbamoyl)pyrrolidin-4-ylthio)-6-(1-hydroxyethyl)-1-methylcarbapenem-3-carboxylate. Nmr (DHSO-d$_6$+acetic acid-d$_4$): δ 1.21 (d, 6H); 2.05 (br, 1H); 2.85 (br, 1H); 3.29 (dd, 1H); 3.44 (dd, 1H); 3.51 (quintet, 1H); 3.93 (br, 1H); 4.05–4.18 (m, 2H); 4.27 (dd, 1H); 4.43–4.71 (overlapping m, 5H); 4.85 (d, 2H); 5.16–5.46 (m, 6H); 5.70–6.16 (m, 3H); 7.94 (br s, 1H); 8.37 (br s, 1H); 8.53 (br s, 1H).

Ms (+ve FAB): 708 (MH)$^+$; 730 (M+Na)$^+$

EXAMPLE 26

(1R,5S,6S,8R,2'S,4'S)-2-(2-(5-Carboxy-2-methoxyphenylcarbamoyl)pyrrolidin-4-ylthio)-6-(1-hydroxyethyl)-1-methylcarbapenem-3-carboxylic acid, disodium salt was prepared using the technique of Example 1. Nmr (DMSO-d$_6$+acetic acid-d$_4$): δ 1.20 (d, 6H); 1.93 (m, part obscured, 1H); 2.86 (quintet, 1H); 3.02 (dd, 1H); 3.26 (dd, 1H); 3.44 (quintet, 1H); 3.68 (dd, 1H); 3.84 (quintet, 1H); 3.95 (s, 3H); 4.03 (quintet, 1H); 4.22 (dd, 1H); 4.34 (t, 1H); 7.13 (d, 1H); 7.78 (dd, 1H); 8.25 (d, 1H).

Ms (+ve FAB): 528 (MH)$^+$, (Na salt); 550 (MH)$^+$, (Na$_2$ salt)

The starting materials were prepared as follows:

4-Methoxy-3-nitrobenzoic acid was allylated essentially as in Example 1, except that the product was sufficiently pure for use without chromatography, to give allyl 3-nitro-4-methoxybenzoate. Nmr (CDCl$_3$): δ 4.03 (s, 3H); 4.83 (dt, 2H); 5.29–5.46 (m, 2H); 5.93–6.14 (m, 1H); 7.14 (d, 1H); 8.24 (dd, 1H); 8.52 (d, 1H).

Ms (CI): 237 M$^+$; 255 (M+NH$_4$)$^+$

Reduction of the above nitro compound by the method of Example 2 gave allyl 3-amino-4-methoxybenzoate sufficiently pure for use without chromatography. Nmr (CDCl$_3$): δ 3.72 (br, 2H); 3.90 (s, 3H); 4.77 (dt, 2H); 5.24–5.43 (m, 2H); 5.95–6.10 (m, 1H); 6.79 (d, 1H); 7.41 (d, 1H); 7.50 (dd, 1H).

Ms (CI): 208 (MH)$^+$

The above amine was condensed with proline acid as Example 4, except that the material was purified by chromatography on silica, using a gradient from dichloromethane to dichloromethane/diethyl ether (4:1), giving (2S,4S)-1-allyloxycarbonyl-2-(5-allyloxycarbonyl-2-methoxyphenylcarbamoyl)pyrrolidin-4-ylthioacetate. Nmr (CDCl$_3$): δ 2.33 (s, 3H); 2.51 (br, 1H); 2.66 (br, 1H); 3.41 (dd, 1H); 3.93 (s, 3H); 4.01 (quintet, 1H); 4.17 (dd, 1H); 4.55 (t, 1H); 4.64 (d, 2H); 4.80 (dt, 2H); 5.18–5.44 (m, 4H); 5.81–6.14 (m overlapping br, 2H); 6.91 (d, 1H); 7.84 (dd, 1H); 8.90 (br, 1H); 9.01 (d, 1H).

Ms (+ve FAB): 463 (MH)$^+$; 485 (M+Na)$^+$

The above thioacetate was deacetylated and condensed with carbapenem phosphate as Example 1, purifying by chromatography using a gradient from dichloromethane to ethyl acetate to give allyl (1R,5S,6S,8R,2'S,4'S)-2-(1-allyloxycarbonyl-2-(5-allyloxycarbonyl-2-methoxyphenylcarbamoyl)pyrrolidin-4-ylthio)-6-(1-hydroxyethyl)-1-methylcarbapenem-3-carboxylate. Nmr (CDCl$_3$): δ 1.23 (d, 3H); 1.36 (d, 3H); 2.52 (br, 1H); 2.66 (br, 1H); 3.22 (dd, 1H); 3.28 (quintet, 1H); 3.44 (dd, 1H); 3.83 (quintet, 1H); 3.93 (s, 3H); 4.09 (m, 1H); 4.19–4.31 (overlapping m, 2H); 4.53 (t, 1H); 4.65 (m, 4H); 4.81 (d, 2H); 5.19–5.45 (m, 6H); 5.83–6.11 (m, 3H); 6.91 (d, 1H); 7.83 (dd, 1H); 8.79 (br, 1H); 9.04 (d, 1H).

Ms (+ve FAB): 670 (MH)$^+$; 692 (M+Na)$^+$

EXAMPLE 27

(1R,5S,6S,8R,2'S,4'S)-2-(2-(3-Carboxy-4-methoxyphenylcarbamoyl)pyrrolidin-4-ylthio)-6-(1-hydroxyethyl)-1-methylcarbapenem-3-carboxylic acid, disodium salt was prepared using the technique of Example 2, except that the DMF was replaced by DMSO. Nmr (DMSO-d$_6$+acetic acid-d$_4$): δ 1.17 (d, 6H); 1.83 (m, part obscured, 1H); 2.75 (quintet, 1H); 2.97 (dd, 1H); 3.23 (dd, 1H); 3.40 (quintet, 1H); 3.56 (dd, 1H); 3.82 (s+m, 4H); 3.99 (quintet, 1H); 4.12 (t, 1H); 4.19 (dd, 1H); 7.09 (d, 1H); 7.75 (dd, 1H); 7.95 (d, 1H).

Ms (+ve FAB): 528 (MH)$^+$, (Na salt); 550 (MH)$^+$, (Na$_2$ salt)

The starting materials were prepared as follows:

2-Methoxy-5-nitrobenzoic acid was allylated essentially as in Example 1, except that the product was sufficiently pure for use without chromatography, to give allyl 2-methoxy-5-nitrobenzoate. Nmr (CDCl$_3$): δ 4.03 (s, 3H); 4.85 (dt, 2H); 5.30–5.49 (m, 2H); 5.95–6.14 (m, 1H); 7.08 (d, 1H); 8.48 (dd, 1H); 8.72 (d, 1H).

Ms (CI): 238 (MH)$^+$; 255 (M+NH$_4$)$^+$

Reduction of the above nitro compound by the method of Example 2 gave allyl 5-amino-2-methoxybenzoate sufficiently pure for use without chromatography. Nmr (CDCl$_3$): δ 3.39 (br, 2H); 3.83 (s, 3H); 4.80 (dt, 2H); 5.23–5.47 (m, 2H); 5.94–6.13 (m, 1H); 6.83 (d, 2H); 7.18 (t, 1H).

Ms (CI): 208 (MH)$^+$

The above amine was condensed with proline acid as Example 4, except that the material was purified by chromatography on silica, using a gradient from dichloromethane to dichloromethane/diethyl ether (4:1), giving (2S,4S)-1-allyloxycarbonyl-2-(3-allyloxycarbonyl-4-methoxyphenylcarbamoyl)pyrrolidin-4-ylthioacetate. Nmr (CDCl$_3$): δ 2.32 (s, 3H); 2.58 (br, 2H); 3.39 (dd, 1H); 3.89 (s, 3H); 4.02 (quintet, 1H); 4.13 (dd, 1H); 4.53 (t, 1H); 4.66 (dt, 2H); 4.80 (dt, 2H); 5.23–5.48 (m, 4H); 5.84–6.13 (m, 2H); 6.94 (d, 1H); 7.80 (m, 2H); 8.94 (br, 1H).

Ms (CI): 463 (MH)$^+$

The above thioacetate was deacetylated and condensed with carbapenem phosphate as Example 1, purifying by chromatography using a gradient from dichloromethane to ethyl acetate to give allyl (1R,5S,6S,8R,2'S,4'S)-2-(1-allyloxycarbonyl-2-(3-allyloxycarbonyl-4-methoxyphenylcarbamoyl)pyrrolidin-4-ylthio)-6-(1-hydroxyethyl)-1-methylcarbapenem-3-carboxylate. Nmr (CDCl$_3$): δ 1.25 (d, 3H); 1.36 (d, 3H); 2.65 (br, 2H); 3.25 (dd, 1H); 3.28 (quintet, 1H); 3.47 (br, 1H); 3.79 (quintet, 1H); 3.89 (s, 3H1); 4.01 (dd, 1H1); 4.18–4.29 (overlapping m, 2H); 4.51 (t, 3H); 4.66 (m, 4H); 4.79 (dt, 2H); 5.19–5.46 (m, 6H); 5.84–6.11 (m, 3H); 6.95 (d, 1H); 7.79–7.87 (m, 2H); 8.70 (br, 1H).

Ms (+ve FAB): 670 (MH)$^+$; 692 (M+Na)$^+$

EXAMPLE 28

(1R,5S,6S,8R,2'S,4'S)-2-(2-(3-Carboxy-2-methoxyphenylcarbamoyl)pyrrolidin-4-ylthio)-6-(1-hydroxyethyl)-1-methylcarbapenem-3-carboxylic acid, disodium salt was prepared using the technique of Example 2, except that the DHF was replaced by DMSO. Nmr (DMSO-d$_6$+acetic acid-d$_4$): δ 1.18 (d, 6H); 1.85 (m, part obscured, 1H); 2.66–2.86 (overlapping m, 2H); 3.21 (dd, 1H); 3.41 (quintet, 1H); 3.52–3.72 (overlapping m, 2H); 3.82 (s, 3H); 3.99 (quintet, 1H); 4.08 (dd, 1H); 4.17 (dd, 1H); 7.17 (t, 1H); 7.45 (dd, 1H); 8.41 (dd, 1H).

Ms (+ve FAB): 528 (MH)$^+$, (Na salt); 550 (MH)$^+$, (Na$_2$ salt)

The starting materials were prepared as follows:

2-Hydroxy-3-nitrobenzoic acid was methylated essentially as the allylation step of Example 1, except that the allyl bromide was replaced by methyl iodide, and purification by chromatography was unnecessary, to give methyl 2-methoxy-3-nitrobenzoate. Nmr (DMSO-d$_6$): δ 3.88 (s, 3H); 3.90 (s, 3H); 7.44 (t, 1H); 8.04 (dd, 1H); 8.12 (dd, 1H).

Ms (CI): 212 (MH)$^+$; 229 (M+NH$_4$)$^+$

The above ester (3.45 g, 16 mM) was hydrolysed by essentially the method of Example 22, except that the solvent was DMSO in place of THF, to give 2-methoxy-3-nitrobenzoic acid. Nmr (DMSO-d$_6$): δ 3.89 (s, 3H); 7.40 (t, 1H); 8.01 (dd, 1H); 8.06 (dd, 2H)).

Ms (CI): 215 (M+NH$_4$)$^+$

The above nitro acid was allylated essentially as in Example 1, except that the product was sufficiently pure for use without chromatography, to give allyl 2-methoxy-3-nitrobenzoate. Nmr (CDCl$_3$): δ 4.00 (s, 3H); 4.86 (dt, 2H); 5.31–5.50 (m, 2H); 5.96–6.16 (m, 1H); 7.27 (d, 1H); 7.92 (dd, 1H); 8.06 (dd, 1H).

Ms (CI): 238 (MH)$^+$; 255 (M+NH$_4$)$^+$

Reduction of the above nitro compound by the method of Example 1 gave allyl 3-amino-2-methoxybenzoate sufficiently pure for use without chromatography. Nmr (CDCl$_3$): δ 3.86 (s, 3H); 3.92 (br, 2H); 4.82 (dt, 2H); 5.26–5.49 (m, 2H); 5.96–6.16 (m, 1H); 6.91 (dd, 1H); 7.00 (t, 1H); 7.23 (dd, 1H).

Ms (CI): 208 (MH)$^+$; 225 (M+NH$_4$)$^+$

The above amine was condensed with proline acid as Example 4, to give (2S,4S)-1-allyloxycarbonyl-2-(3-allyloxycarbonyl-2-methoxyphenylcarbamoyl)pyrrolidin-4-ylthioacetate. Nmr (CDCl$_3$): δ 2.30 (s, 3H); 2.53 (br, 1H); 2.65 (br, 1H); 3.41 (dd, 1H); 3.86 (s, 3H); 4.04 (quintet, 1H); 4.16 (dd, 1H); 4.58 (t, 1H); 4.66 (d, 2H); 4.83 (dt, 2H); 5.20–5.47 (m, 4H); 5.83–6.13 (m overlapping br, 2H); 7.16 (t, 1H); 7.60 (dd, 1H); 8.57 (dd, 1H); 9.15 (br, 1H).

Ms (+ve FAB): 463 (MH)$^+$; 485 (M+Na)$^+$

The above thioacetate was deacetylated and condensed with carbapenem phosphate as Example 1, purifying by chromatography using a gradient from dichloromethane to ethyl acetate to give allyl (1R,5S,6S,8R,2'S,4'S)-2-(1-allyloxycarbonyl-2-(3-allyloxycarbonyl-2-methoxyphenylcarbamoyl)pyrrolidin-4-ylthio)-6-(1-hydroxyethyl)-1-methylcarbapenem-3-carboxylate. Nmr (CDCl$_3$): δ 1.24 (d, 3H); 1.35 (d, 3H); 2.53 (br, 1H); 2.68 (br, 1H); 3.24 (dd, 1H); 3.28 (quintet, 1H); 3.43 (br, 1H); 3.80 (quintet, 1H); 3.83 (s, 3H); 4.12 (m, 1H); 4.19–4.29 (overlapping m, 2H); 4.57 (t, 1H); 4.64 (m, 4H); 4.83 (d, 2H); 5.18–5.48 (m, 6H); 5.81–6.14 (m, 3H); 7.17 (t, 1H); 7.61 (dd, 1H); 8.56 (dd, 1H); 9.02 (br, 1H).

Ms (+ve FAB): 670 (MH)$^+$; 692 (M+Na)$^+$

EXAMPLE 29

(1R,5S,6S,8R,2'S,4'S)-2-(2-(5-Carboxy-2-methylphenylcarbamoyl)pyrrolidin-4-ylthio)-6-(1-hydroxyethyl)-1-methylcarbapenem-3-carboxylic acid, disodium salt was prepared using the technique of Example 2, except that the DNF was replaced by DMSO. Nmr (DMSO-$d_6$+acetic acid-$d_4$): δ 1.19 (d, 6H); 1.88 (m, part obscured, 1H); 2.31 (s, 3H); 2.77 (dt, 1H); 2.93 (dd, 1H); 3.22 (dd, 1H); 3.42 (quintet, 1H); 3.57 (dd, 1H); 3.77 (quintet, 1H); 4.01 (quintet, 1H); 4.16 (t, 1H); 4.19 (dd, 1H); 7.35 (d, 1H); 7.69 (dd, 1H); 8.39 (d, 1H).

Ms (+ve FAB): 512 (MH)$^+$, (Na salt); 534 (MH)$^+$, (Na$_2$ salt); 556 (M+Na)$^+$, (Na$_2$ salt);

The starting materials were prepared as follows:

4-Methyl-3-nitrobenzoic acid was allylated as in Example 1, except that purification by chromatography was unnecessary, to give allyl 4-methyl-3-nitrobenzoate. Nmr (DMSO-$d_6$: δ 2.59 (s, 3H); 4.84 (dt, 2H); 5.27–5.47 (m, 2H); 5.96–6.16 (m, 1H); 7.67 (d, 1H); 8.16 (dd, 1H); 8.44 (d, 1H).

Ms (EI): 222 (MH)$^+$

Reduction of the above nitro compound by the method of Example 2, except that the solvent was methanol, gave allyl 3-amino-4-methylbenzoate sufficiently pure for use without chromatography. Nmr (DMSO-$d_6$): δ 2.10 (s, 3H); 4.74 (dt, 2H); 5.15 (br, 2H); 5.22–5.43 (m, 2H); 5.93–6.12 (m, 1H); 7.04 (d, 1H); 7.11 (dd, 1H); 7.28 (d, 1H).

Ms (CI): 192 (MH)$^+$; 209 (M+NH$^4$)$^+$

The above amine was condensed with proline acid as Example 4, purifying by chromatography using a gradient from dichloromethane to dichloromethane/diethyl ether (9:1), to give (2S,4S)-1-allyloxycarbonyl-2-(5-allyloxycarbonyl-2-methylphenylcarbamoyl)pyrrolidin-4-ylthioacetate. Nmr (DHSO-$d_6$, mix of rotamers): δ 1.97 (quintet, 1H); 2.26 (s, 3H); 2.34 (s, 3H); 2.80 (br, 1H); 3.30 (br, 1H); 3.93–4.08 (br m, 2H); 4.53 (br, 3H); 4.80 (dt, 2H); 5.10–5.44 (m overlapping br, 4H); 5.78–6.13 (m overlapping br, 2H); 7.38 (d, 1H); 7.72 (dd, 1H); 7.94 (br, 0.5H); 8.01 (br, 0.5H); 9.61 (br, 0.5H); 9.67 (br, 0.5H).

Ms (CI): 447 (MH)$^+$; 464 (M+NH$^4$)$^+$

The above thioacetate was deacetylated and condensed with carbapenem phosphate as Example 1, purifying by chromatography using a gradient from dichloromethane to dichloromethane/ethyl acetate (1:1), to give allyl(1R,5S,6S,8R,2'S,4'S)-2-(1-allyloxycarbonyl-2-(5-allyloxycarbonyl-2-methylphenylcarbamoyl)pyrrolidin-4-ylthio)-6-(1-hydroxyethyl)-1-methylcarbapenem-3-carboxylate. Nmr (DMSO-$d_6$+acetic acid-$d_4$, mix of rotamers): δ 1.16 (d, 3H); 1.18 (d, 3H); 1.98 (quintet, 1H); 2.27 (s, 3H); 2.86 (br, 1H); 3.27 (dd, 1H); 3.33 (t, 1H); 3.56 (quintet, 1H); 3.95 (quintet, 1H); 4.02 (dd, 1H); 4.15 (quintet, 1H); 4.27 (dd, 1H); 4.48–4.70 (overlapping m, 5H); 4.80 (d, 2H); 5.10–5.45 (m overlapping br, 6H); 5.81–6.14 (m overlapping br, 3H); 7.38 (d, 1H); 7.75 (dd, 1H); 8.01 (br, 0.5H); 8.07 (br, 0.5H); 9.60 (br, 1H).

Ms (+ve FAB): 654 (MH)$^+$; 676 (M+Na)$^+$

EXAMPLE 30

(1R,5S,6S,8R,2'S,4'S)-2-(2-(3-Carboxy-4-methylphenylcarbamoyl)pyrrolidin-4-ylthio)-6-(1-hydroxyethyl)-1-methylcarbapenem-3-carboxylic acid, disodium salt was prepared using the technique of Example 2, except that the DMF was replaced by DMSO. Nmr (DMSO-$d_6$+acetic acid-$d_4$): δ 1.15 (d, 3H); 1.16 (d, 3H); 1.78 (dt, 1H); 2.48 (s, 3H); 2.60 (dt, 1H); 2.90 (dd, 1H); 3.21 (dd, 1H); 3.39 (quintet, 1H); 3.49 (dd, 1H); 3.73 (quintet, 1H); 3.99 (quintet, 1H); 4.03 (t, 1H); 4.17 (dd, 1H); 7.23 (d, 1H); 7.70 (dd, 1H); 8.12 (d, 1H).

Ms (+ve FAB): 512 (MH)$^+$, (Na salt); 534 (MH)$^+$, (Na$_2$ salt); 556 (M+Na)$^+$, (Na$_2$ salt)

The starting materials were prepared as follows:

2-Methyl-5-nitrobenzoic acid was allylated as in Example 1, except that purification by chromatography was unnecessary, to give allyl 2-methyl-5-nitrobenzoate. Nmr (DMSO-$d_6$): δ 2.65 (s, 3H); 4.84 (dt, 2H); 5.28–5.47 (m, 2H); 5.99–6.18 (m, 1H); 7.65 (d, 1H); 8.31 (dd, 1H); 8.57 (d, 1H).

Ms (CI): 222 (MH)$^+$; 099 (M+NH$^4$)$^+$

Reduction of the above nitro compound by the method of Example 2, except that the solvent was methanol, gave allyl 5-amino-2-methylbenzoate sufficiently pure for use without chromatography. Nmr (DMSO-$d_6$): δ 2.33 (s, 3H); 4.73 (dt, 2H); 5.18 (br, 2H); 5.23–5.44 (m, 2H); 5.93–6.12 (m, 1H); 6.68 (dd, 1H); 6.95 (d, 1H); 7.12 (d, 1H).

Ms (CI): 192 (MH)$^+$; 209 (M+NH$^4$)$^+$

The above amine was condensed with proline acid as Example 4, purifying by chromatography using a gradient from dichloromethane to dichloromethane/diethyl ether (9:1), to give (2S,4S)-1-allyloxycarbonyl-2-(3-allyloxycarbonyl-4-methylphenylcarbamoyl)pyrrolidin-4-ylthioacetate. Nmr (DMSO-$d_6$, mix of rotamers): δ 1.91 (br m, 1H); 2.33 (s, 3H); 2.76 (br m, 1H); 3.28 (s overlapping m, 4H); 4.00 (br m, 2H); 4.38 (t, 1H); 4.51 (br, 2H); 4.78 (dt, 2H); 5.01–5.46 (m overlapping br, 4H); 5.68–6.16 (m overlapping br, 2H); 7.27 (d, 1H); 7.72 (dd, 1H); 8.11 (br, 0.5H); 8.05 (br, 0.5H); 10.17 (br, 1H).

Ms (+FAB): 447 (MH)$^+$; 469 (M+Na)$^+$

The above thioacetate was deacetylated and condensed with carbapenem phosphate as Example 1, purifying by chromatography using a gradient from dichloromethane to dichloromethane/ethyl acetate (1:1), to give allyl(1R,5S,6S,8R,2'S,4'S)-2-(1-allyloxycarbonyl-2-(3-allyloxycarbonyl-4-methylphenylcarbamoyl)pyrrolidin-4-ylthio)-6-(1-hydroxyethyl)-1-methylcarbapenem-3-carboxylate. Nmr (DMSO-$d_6$+acetic acid-$d_4$): δ 1.19 (d, 6H); 1.92 (br, part obscured, 1H); 2.48 (s, 3H); 2.79 (br, 1H); 3.25 (dd, 1H); 3.32 (t, 1H); 3.54 (quintet, 1H); 3.91 (br m, 1H); 4.01 (quintet, 1H); 4.12 (dd, 1H); 4.25 (dd, 1H); 4.45 (m, 1H); 4.50–4.68 (m, 4H); 4.78 (dt, 2H); 5.18–5.45 (m, 6H); 5.70–6.13 (m overlapping br, 3H); 7.25 (d, 1H); 7.76 (dd, 1H); 8.12 (br m, 1H).

Ms (+ve FAB): 654 (MH)$^+$; 676 (M+Na)$^+$

EXAMPLE 31

(1R,5S,6S,8R,2'S,4'S)-2-(2-(3-Carboxy-5-methylphenylcarbamoyl)pyrrolidin-4-ylthio)-6-(1-hydroxyethyl)-1-methylcarbapenem-3-carboxylic acid, disodium salt Allyl(1R,5S,6S,8R,2'S,4'S)-2-(1-allyloxycarbonyl-2-(3-allyloxycarbonyl-5-methylphenylcarbamoyl)pyrrolidin-4-ylthio)-6-(1-hydroxyethyl)-1-methylcarbapenem-3-carboxylate (3 g, 4.59 mM) and 2,2-dimethyl-1,3-dioxane-4,6-dione (3.97 g, 27.6 mM) were dissolved in a mixture of DMSO (15 ml) and THF (5 ml), under an argon atmosphere, and tetrakis(triphenylphosphine)palladium (531 mg, 0.46 mM) was added. The solution was stirred, under argon with protection from light, for 1 hour. A solution of sodium 2-ethylhexanoate (1.53 g, 9.22 mM) in THF (5 ml) was added, followed by THF (250 ml). The resultant precipitate was filtered, under an argon blanket to exclude moisture, and washed successively with small portions of THF (twice), and diethyl ether. Crude product and $NaHCO_3$ (1.5 g) were dissolved in water (100 ml), and the solution chromatographed on HP20SS resin using a gradient elution from water to water/acetonitrile (9:1). Appropriate fractions were combined and freeze-dried to give (1R,5S,6S,8R,2'S,4'S)-2-(2-(3-carboxy-5-methylphenylcarbamoyl)pyrrolidin-4-ylthio)-6-(1-hydroxyethyl)-1-methylcarbapenem-3-carboxylic acid, disodium salt. Nmr (DMSO-d6+acetic acid-$d_4$): δ 1.13 (d, 3H); 1.15 (d, 3H); 1.76 (dt, 1H); 2.32 (s, 3H); 2.68 (dt, 1H); 2.87 (dd, 1H); 3.18 (dd, 1H); 3.36 (quintet, 1H); 3.45 (dd, 1H); 3.71 (quintet, 1H); 3.95 (quintet, 1H); 4.02 (t, 1H); 4.14 (dd, 1H); 7.49 (s, 1H); 7.65 (s, 1H); 8.05 (s, 1H).

Ms (+ve FAB): 512 (MH)$^+$, (Na salt); 534 (MH)$^+$, ($Na_2$ salt); 556 (M+Na)$^+$, ($Na_2$ salt)

The starting materials were prepared as follows:
3-Methyl-5-nitrobenzoic acid 3,5-Dimethylnitrobenzene (30 g, 0.198M) was heated with stirring to 80° in a mixture of pyridine (400 ml) and water (250 ml). $KMnO_4$ (62.7 g, 0.396M) was added in portions over 0.75 hours, and heating continued at 85°–90° for 1.75 hours. The hot solution was filtered through celite, washing with hot water (150 ml). The pink filtrates were decolourised with a few drops of sodium metabisulfite, and evaporated to dryness. The residue was dissolved in water (250 ml), and extracted with diethyl ether (2×90 ml). The aqueous layer was acidified (concentrated hydrochloric acid), and extracted with ethyl acetate (3×120 ml). Combined organic extracts were washed with $NaH_2PO_4$ solution, brine, and dried over $MgSO_4$. Crude product was eluted through a pad of silica, using a mixture of ethyl acetate/dichloromethane/acetic acid (25:25:1), to give 3-methyl-5-nitrobenzoic acid (14.5 g, 40%), mp 171°–172°. Nmr (DMSO-$d_6$): δ 2.51 (s, 3H); 8.17 (s, 1H); 8.30 (t, 1H); 8.42 (t, 1H); 13.58 (br, 1H).

Ms (CI): 181 (MH)$^+$

3-Methyl-5-nitrobenzoic acid was allylated as in Example 1, except that purification by chromatography was unnecessary, to give allyl 3-methyl-5-nitrobenzoate. Nmr ($CDCl_3$): δ 2.53 (s, 3H); 4.87 (dt, 2H); 5.31–5.48 (m, 2H); 5.99–6.13 (m, 1H); 8.20 (s, 1H); 8.23 (s, 1H); 8.68 (s, 1H).

Ms (CI): 222 (MH)$^+$

Reduction of the above nitro compound by the method of Example 1, gave allyl 5-amino-3-methylbenzoate sufficiently pure for use without chromatography. Nmr ($CDCl_3$): δ 2.30 (s, 3H); 3.46 (br, 2H); 4.78 (dt, 2H); 5.23–5.45 (m, 2H); 5.93–6.12 (m, 1H); 6.68 (t, 1H); 7.17 (t, 1H); 7.27 (t, 1H).

Ms (CI): 192 (MH)$^+$; 220 (M+$C_2H_5$)$^+$

The above amine was condensed with proline acid as Example 4, purifying by chromatography using hexane/ethyl acetate (3:1) as eluant, to give (2S,4S)-1-allyloxycarbonyl-2-(3-allyloxycarbonyl-5-methylphenylcarbamoyl)pyrrolidin-4-ylthioacetate. Nmr ($CDCl_3$): δ 2.33 (s, 3H); 2.39 (s, 3H); 2.58 (br, 2H); 3.29 (dd, 1H); 4.02 (quintet, 1H); 4.13 (dd, 1H); 4.56 (t, 1H); 4.68 (dm, 2H); 4.82 (dt, 2H); 5.23–5.44 (m, 4H); 5.86–6.12 (m, 2H); 7.63 (s, 1H); 7.85 (s, 1H); 7.85 (s, 1H); 9.09 (br, 1H).

Ms (+FAB): 447 (MH)$^+$

The above thioacetate was deacetylated and condensed with carbapenem phosphate as Example 1, purifying by chromatography using a gradient of dichloromethane/ethyl acetate (3:2 to 2:3), to give allyl (1R,5S,6S,8R,2'S,4'S)-2-(1-allyloxycarbonyl-2-(3-allyloxycarbonyl-5-methylphenylcarbamoyl)pyrrolidin-4-ylthio)-6-(1-hydroxyethyl)-1-methylcarbapenem-3-carboxylate. Nmr ($CDCl_3$): δ 1.23 (d, 3H); 1.35 (d, 3H); 2.38 (s, 3H); 2.63 (br, 2H); 3.23 (dd, 1H); 3.27 (quintet, 1H); 3.46 (br, 1H); 3.78 (quintet, 1H); 4.00 (dd, 1H); 4.24 (overlapping m, 2H); 4.51 (t, 1H); 4.59–4.63 (m, 4H); 4.79 (d, 2H); 5.17–5.42 (m, 6H); 5.82–6.09 (m, 3H); 7.61 (s, 1H); 7.73 (s, 1H); 7.99 (s, 1H); 8.87 (br, 1H).

Ms (+ve FAB): 654 (MH)$^+$

EXAMPLE 32

(1R,5S,6S,8R,2'S,4'S)-2-(2-(3-Carboxy-5-methoxycarbonylphenylcarbamoyl)pyrrolidin-4-ylthio)-6-(1-hydroxyethyl)-1-methylcarbapenem-3-carboxylic acid, disodium salt was prepared using the technique of Example 2, except that the DMF was replaced by DMSO. Nmr (DMSO-$d_6$+acetic acid-$d_4$): δ 1.18 (d, 6H); 1.92 (br, part obscured, 1H); 2.81 (m, 1H); 3.03 (dd, 1H); 3.23 (dd, 1H); 3.41 (quintet, 1H); 3.61 (m, 1H); 3.90 (s overlapping m, 4H); 4.00 (quintet, 1H); 4.21 (overlapping m, 2H); 8.25 (t, 1H); 8.50 (m, 2H).

Ms (+ve FAB): 556 (MH)$^+$, (Na salt); 578 (MH)$^+$, ($Na_2$ salt)

The starting materials were prepared as follows:

3-Methoxycarbonyl-5-nitrobenzoic acid was allylated as in Example 1, except that purification by chromatography was unnecessary, to give allyl 3-methoxycarbonyl-5-nitrobenzoate. Nmr (DMSO-$d_6$): δ 3:97 (s, 3H); 4.91 (dt, 2H); 5.31–5.51 (m, 2H); 6.00–6.19 (m, 1H); 8.75 (t, 1H); 8.81 (d, 2H).

Ms (EI): 265 M$^+$

Reduction of the above nitro compound by the method of Example 2, except that the solvent was methanol, gave allyl 3-amino-5-methoxycarbonylbenzoate sufficiently pure for use without chromatography. Nmr (DMSO-$d_6$): δ 3.79 (br, 2H); 3.92 (s, 3H); 4.82 (dt, 2H); 5.26–5.46 (m, 2H); 5.94–6.14 (m, 1H); 7.53 (m, 2H); 8.07 (t, 1H).

Ms (CI): 236 (MH)$^+$; 253 (M+$NH_4$)$^+$

The above amine was condensed with proline acid as Example 1, purifying by chromatography using a gradient from dichloromethane to dichloromethane/diethyl ether (9:1), to give (2S,4S)-1-allyloxycarbonyl-2-(3-allyloxycarbonyl-5-methoxycarbonylphenylcarbamoyl)pyrrolidin-4-ylthioacetate. Nmr ($CDCl_3$): δ 2.33 (s, 3H); 2.60 (br, 2H); 3.40 (dd, 1H); 3.94 (s, 3H); 4.04 (quintet, 1H); 4.14 (dd, 1H); 4.58 (t, 1H); 4.68 (dm, 2H); 4.85 (dt, 2H); 5.25–5.47 (m, 4H); 5.85–6.16 (m, 2H); 8.36 (t, 1H); 8.43 (m, 2H); 9.40 (br, 1H).

Ms (+FAB): 491 (MH)$^+$; 513 (M+Na)$^+$ (2S,4S)-1-Allyloxycarbonyl-2-(3-allyloxycarbonyl-5-methoxycarbonylphenylcarbamoyl)pyrrolidin-4-ylthioacetate (1.2 g, 2.4 mM) was dissolved in THF (50 ml) under an argon atmosphere, and aqueous methylamine (33% w/v, 0.51 g, 5.4 mM) was added. Stirring was continued for 3 hours, and solvent removed. The residue was treated with 2M hydrochloric acid and extracted with ethyl acetate. The organic solution was washed with water, brine, aqueous $NaHCO_3$ and dried over $MgSO_4$. Removal of solvents gave (2S,4S)-1-allyloxycarbonyl-2-(3-allyloxycarbonyl-5-methoxycarbonylphenylcarbamoyl)pyrrolidin-4-ylthiol (1.02 g, 93%). The thiol was condensed without further purification with carbapenem phosphate as Example 1, purifying by chromatography using a gradient from dichloromethane to dichloromethane/ethyl acetate (1:1), to give allyl(1R,5S,6S,8R,2'S,4'S)-2-(1-allyloxycarbonyl-2-(3-allyloxycarbonyl-5-methoxycarbonylphenylcarbamoyl)

pyrrolidin-4-ylthio)-6-(1-hydroxyethyl)-1-methylcarbapenem-3-carboxylate. Nmr (CDCl$_3$): δ 1.24 (d, 3H); 1.37 (d, 3H); 2.64 (br, 2H); 3.26 (dd overlapping quintet, 2H); 3.48 (br, 1H); 3.86 (quintet, 1H); 3.94 (s overlapping m, 4H); 4.25 (quintet, 1H); 4.29 (dd, 1H); 4.56 (t, 1H); 4.69 (m, 4H); 4.86 (dm, 2H); 5.19–5.46 (m, 6H); 5.85–6.13 (m, 3H); 8.46 (m, 3H); 9.18 (br, 1H).

Ms (+ve FAB): 698 (MH)$^+$; 720 (M+Na)$^+$

EXAMPLE 33

(1R,5S,6S,8R,2'S,4'S)-2-(2-(5-Carboxy-2,4-difluorophenylcarbamoyl)pyrrolidin-4-ylthio)-6-(1-hydroxyethyl)-1-methylcarbapenem-3-carboxylic acid, disodium salt was prepared using the technique of Example 2. Nmr (DMSO-d$_6$+acetic acid-d$_4$): δ 1.20 (d, 6H); 1.96 (m, part obscured, 1H); 2.81 (m, 1H); 3.14 (dd, 1H); 3.27 (dd, 1H); 3.43 (quintet, 1H); 3.73 (m, 1H); 3.91 (quintet, 1H); 4.04 (quintet, 1H); 4.23 (dd, 1H); 4.43 (t, 2H); 7.29 (t, 1H); 8.54 (t, 1H).

Ms (+ve FAB): 534 (MH)$^+$, (Na salt); 556 (MH)$^+$, (Na$_2$ salt)

The starting materials were prepared as follows:
2,4-Difluoro-5-nitrobenzoic acid 2,4-Difluorobenzoic acid (5 g, 0.031M) was dissolved in concentrated sulfuric acid (30 ml), and cooled to 0°. The mixture was stirred, and fuming nitric acid (d 1.567 g/ml, 1.91 ml, 0.047M) added dropwise, keeping the temperature below 5°. After stirring for 3 hours, the mix was poured onto ice, and organics extracted into dichloromethane (2×75 ml). The combined organic layers were washed with water, dried (MgSO$_4$), and evaporated to give 2,4-difluoro-5-nitrobenzoic acid (3.9 g, 61%). Nmr (DMSO-d$_6$): δ 7.18 (t, 1H); 8.88 (t, 1H); 9.93 (br, 1H).

Ms (-FAB): 202 (M-H)$^-$ 2,4-Difluoro-5-nitrobenzoic acid was allylated as in Example 1, except that the reaction time was only 1.5 hours, the DMF was stirred over IR-120-H ion exchange resin before use, and purification by chromatography was unnecessary, to give allyl 2,4-difluoro-5-nitrobenzoate. Nmr (CDCl$_3$): δ 4.88 (dt, 2H); 5.31–5.50 (m, 2H); 5.93–6.13 (m, 1H); 7.13 (t, 1H); 8.80 (dd, 1H).

Ms (EI): 265 M$^+$

Reduction of the above nitro compound by the method of Example 2, except that the solvent was methanol, gave allyl 5-amino-2,4-difluorobenzoate, sufficiently pure for use without chromatography.

Nmr (CDCl$_3$): δ 3.61 (br, 2H); 4.81. (dt, 2H); 5.26–5.48 (m, 2H); 5.92–6.12 (m, 1H); 6.83 (t, 1H); 7.38 (dd, 1H).

Ms (CI): 214 (MH)$^+$; 231 (M+NH$^4$)$^+$

The above amine was condensed with proline acid as Example 1, purifying by chromatography using a gradient from dichloromethane to dichloromethane/diethyl ether (9:1), to give (2S,4S)-1-allyloxycarbonyl-2-(5-allyloxycarbonyl-2,4-difluorophenylcarbamoyl)pyrrolidin-4-ylthioacetate. Nmr (CDCl$_3$): δ 2.33 (s, 3H); 2.63 (br, 2H); 3.39 (dd, 1H); 4.04 (quintet, 1H); 4.14 (dd, 1H); 4.59 (t, 1H); 4.66 (dt, 2H); 4.83 (dt, 2H); 5.22–5.49 (m, 4H); 5.84–6.13 (m, 2H); 6.94 (t, 1H); 8.82 (t, 1H); 9.22 (br, 1H).

Ms (+FAB): 469 (MH)$^+$; 491 (M+Na)$^+$

The above thioacetate was deacetylated and condensed with carbapenem phosphate as Example 1, purifying by chromatography using a gradient from dichloromethane to dichloromethane/ethyl acetate (1:1), to give allyl(1R,5S,6S, 8R,2'S,4'S)-2-(1-allyloxycarbonyl-2-(5-allyloxycarbonyl-2,4-difluorophenylcarbamoyl)pyrrolidin-4-ylthio)-6-(1-hydroxyethyl)-1-methylcarbapenem-3-carboxylate. Nmr (CDCl$_3$): δ 1.25 (d, 3H); 1.38 (d, 3H); 2.62 (br, 2H); 3.24 (dd overlapping quintet, 2H); 3.45 (dd, 1H); 3.88 (quintet, 1H); 4.03 (dd, 1H); 4.25 (quintet, 1H); 4.29 (dd, 1H); 4.57 (t, 1H); 4.68 (m, 4H); 4.82 (dm, 2H); 5.21–5.48 (m, 6H); 5.85–6.10 (m, 3H); 6.94 (t, 1H); 8.85 (t, 1H); 9.12 (br, 1H).

Ms (+ve FAB): 676 (MH)$^+$; 698 (M+Na)$^+$

EXAMPLE 34

(1R,5S,6S,8R,2'S,4'S)-2-(2-(5-Carboxy-2,4-dimethoxyphenylcarbamoyl)pyrrolidin-4-ylthio)-6-(1-hydroxyethyl)-1-methylcarbapenem-3-carboxylic acid, disodium salt was prepared using the technique of Example 2. Nmr (DMSO-d$_6$+acetic acid-d$_4$): δ 1.20 (d, 6H); 1.95 (m, part obscured, 1H); 2.87 (dt, 1H); 3.08 (dd, 1H); 3.26 (dd, 1H); 3.41 (quintet, 1H); 3.71 (dd, 1H); 3.87 (quintet, part obscured, 1H); 3.91 (s, 3H); 3.96 (s, 3H); 4.03 (quintet, 1H); 4.21 (dd, 1H); 4.39 (t, 2H); 6.76 (s, 1H); 8.44 (s, 1H).

Ms (+ve FAB): 558 (MH)$^+$, (Na salt); 580 (MH)$^+$, (Na$_2$ salt)

The starting materials were prepared as follows:
2,4-Dimethoxy-5-nitrobenzoic acid A solution of sodium methoxide was prepared by dissolving sodium metal (1.42 g, 0.062M) in methanol (40 ml) with cooling. Allyl 2,4-difluoro-5-nitrobenzoate (5 g, 0.021M) was added and the mixture was stirred for 2 hours. A solution of NaOH (2 g, 0.05M) in water (10 ml) was added, and the mixture stirred at ambient temperature for 16 hours. Solvent was evaporated, the residue dissolved in water (50 ml), and extracted with diethyl ether (40 ml). The aqueous layer was acidified with sulfuric acid, and the precipitate filtered and dried to give 2,4-dimethoxy-5-nitrobenzoic acid (4.23 g, 91%). Nmr (CDCl$_3$): δ 4.07 (s, 3H); 4.16 (s, 3H); 6.62 (s, 1H); 8.81 (s, 1H).

Ms (CI): 228 (MH)$^+$; 245 (M+NH$^4$)$^+$ 2,4-Dimethoxy-5-nitrobenzoic acid was allylated as in Example 1, except that purification by chromatography was unnecessary, to give allyl 2,4-dimethoxy-5-nitrobenzoate. Nmr (CDCl$_3$): δ 4.02 (s, 3H); 4.04 (s, 3H); 4.79 (dt, 2H); 5.26–5.46 (m, 2H); 5.93–6.13 (m, 1H); 6.54 (s, 1H); 8.63 (s, 1H).

Ms (+FAB): 268 (MH)$^+$; 290 (M+Na)$^+$

Reduction of the above nitro compound by the method of Example 1, gave allyl 5-amino-2,4-dimethoxybenzoate. Nmr (CDCl$_3$): δ 3.25 (br, 2H); 3.87 (s, 3H); 3.90 (s, 3H); 4.76 (dt, 2H); 5.22–5.46 (m, 2H); 5.93–6.12 (m, 1H); 6.47 (s, 1H); 7.29 (s, 1H).

Ms (CI): 238 (MH)$^+$

The above amine was condensed with proline acid as Example 4, purifying by chromatography using a gradient from dichloromethane to dichloromethane/diethyl ether (4:1), to give (2S,4S)-1-allyloxycarbonyl-2-(5-allyloxycarbonyl-2,4-dimethoxyphenylcarbamoyl)pyrrolidin-4-ylthioacetate. Nmr (CDCl$_3$): δ 2.32 (s, 3H); 2.49 (br, 1H); 2.64 (br, 1H); 3.40 (dd, 1H); 3.91 (s, 3H); 3.93 (s, 3H); 4.00 (quintet, 1H); 4.17 (dd, 1H); 4.53 (t, 1H); 4.64 (d, 2H); 4.77 (dt, 2H); 5.19–5.46 (m, 4H); 5.80–6.14 (m overlapping br, 2H); 6.49 (s, 1H); 8.69 (br, 1H); 8.81 (s, 1H).

Ms (+FAB): 493 (MH)$^+$

The above thioacetate was deacetylated and condensed with carbapenem phosphate as Example 1, purifying by chromatography using a gradient from dichloromethane to ethyl acetate, to give allyl (1R,5S,6S,8R,2'S,4'S)-2-(1-allyloxycarbonyl-2-(5-allyloxycarbonyl-2,4-dimethoxyphenylcarbamoyl)pyrrolidin-4-ylthio)-6-(1-hydroxyethyl)-1-methylcarbapenem-3-carboxylate. Nmr (CDCl$_3$): δ 1.22 (d, 3H); 1.36 (d, 3H); 2.48 (br, 1H); 2.65 (br, 1H); 3.23 (dd, 1H); 3.28 (quintet, 1H); 3.43 (dd, 1H); 3.80

(quintet, 1H); 3.91 (s, 3H); 3.92 (s, 3H); 4.09 (dd, 1H); 4.24 (quintet, 1H); 4.27 (dd, 1H); 4.51 (t, 1H); 4.66 (m, 4H); 4.77 (dt, 2H); 5.20–5.45 (m, 6H); 5.83–6.11 (m overlapping br, 3H); 6.49 (s, 1H); 8.45 (br, 1H); 8.82 (s, 1H).

Ms (+ve FAB): 700 (MH)$^+$

EXAMPLE 35

(1R,5S,6S,8R,2'S,4'S)-2-(2-(5-carboxy-2-cyanophenylcarbamoyl)pyrrolidin-4-ylthio)-6-(1-hydroxyethyl)-1-methylcarbapenem-3-carboxylic acid, disodium salt was prepared using the technique of Example 2, except that the DMF was replaced by DMSO. Nmr (DMSO-d$_6$+acetic acid-d$_4$): δ 1.17 (d, 6H); 1.83 (m, part obscured, 1H); 2.62–2.79 (overlapping m, 2H); 3.18 (dd, 1H); 3.41 (quintet, 1H); 3.66 (quintet, 1H); 3.98 (quintet, 1H); 4.07 (dd, 1H); 4.17 (dd, 1H); 7.79 (m, 2H); 8.67 (s, 1H).

Ms (+ve FAB): 523 (MH)$^+$, (Na salt); 545 (MH)$^+$, (Na$_2$ salt)

The starting materials were prepared as follows:
4-Cyano-3-nitrobenzoic acid

4-Chloro-3-nitrobenzoic acid (5.84 g, 29 mM), cuprous cyanide (5.2 g, 58 mM), cuprous chloride (0.96 g, 9.7 mM), and quinoline (6.9 ml, 58 mM) were heated under an argon atmosphere at 180° for 3.5 hours. After cooling, the mixture was dissolved in concentrated hydrochloric acid (60 ml), diluted with water (80 ml), and extracted with ethyl acetate (3×100 ml). The combined organic layers were washed with aqueous NaH$_{22}$PO$_4$, brine, and dried over MgSO$_4$. Crude product was purified by chromatography on silica, eluting with a mixture of dichloromethane/acetic acid (98:2), to give 4-cyano-3-nitrobenzoic acid (2.65 g, 48%). Nmr (DMSO-d$_6$: δ 8.31 (d, 1H); 8.41 (dd, 1H); 8.68 (d, 1H).

Ms (EI): 192 M$^+$

The above nitro acid was allylated essentially as in Example 1, purifying the crude product by chromatography on silica, using an eluant of hexane:ethyl acetate (6:1), to give allyl 4-cyano-3-nitrobenzoate. Nmr (CDCl$_3$): δ 4.93 (dt, 2H); 5.37–5.50 (m, 2H); 5.97–6.13 (m, 1H); 8.03 (d, 1H); 8.46 (dd, 1H); 8.94 (d, 1H).

Ms (CI): 221 (MH)$^+$; 250 (M+NH$^{4+}$)$^+$

Reduction of the above nitro compound by the method of Example 1 gave allyl 3-amino-4-carbamoylbenzoate, recrystallised from ethyl acetate/petrol, mp 149°–150°. Nmr (DMSO-d$_6$): δ 4.77 (dt, 2H); 5.25–5.43 (m, 2H); 5.96–6.11 (m, 1H); 6.72 (br, 2H); 7.04 (dd, 1H); 7.25 (br, 1H); 7.35 (d, 1H); 7.63 (d, 1H); 7.87 (br, 1H).

Ms (EI): 220 M$^+$

The above amine was condensed with proline acid as Example 1, purifying by chromatography using hexane/ethyl acetate (1:1) to give (2S,4S)-1-allyloxycarbonyl-2-(5-allyloxycarbonyl-2-carbamoylphenylcarbamoyl)pyrrolidin-4-ylthioacetate. Nmr (CDCl$_3$, mix of rotamers): δ 2.25 (quintet, 1H); 2.28 (s, 3H); 2.82 (br, 1H); 3.52 (dd, 1H); 4.13 (t, 1H); 4.20 (br m, 1H); 4.52 (dd, 1H); 4.61 (br, 2H); 4.85 (d, 2H); 5.01–5.48 (m overlapping br, 4H); 5.66–6.12 (m overlapping br, 2H); 6.55 (br, 1H); 6.89 (br, 1H); 7.64 (br m, 1H); 7.79 (br m, 1H); 9.30 (br m, 1H); 11.68 (br, 0.5H); 12.06 (br, 0.5H).

Ms (+ve FAB): 476 (MH)$^+$ (2S,4S)-1-Allyloxycarbonyl-2-(5-allyloxycarbonyl-2-cyanophenylcarbamoyl)pyrrolidin-4-ylthioacetate DMF (0.2 ml, 2.5 mM) was dissolved in acetonitrile (10 ml), cooled to −5°, and treated with oxalyl chloride (0.2 ml, 2.3 mm). After stirring for 30 minutes, a solution of (2S, 4S)-1-allyloxycarbonyl-2-(5-allyloxycarbonyl-2-carbamoylphenylcarbamoyl)pyrrolidin-4-ylthioacetate (1 g, 2.1 mM) in acetonitrile (15 ml) was added, followed by pyridine (0.38 ml, 4.6 mM). After 15 minutes, the mixture was diluted with ethyl acetate (200 ml), washed with hydrochloric acid (2M, 20 ml), water, aqueous NaHCO$_3$, and brine, and dried over Na$_2$SO$_4$. Crude product was purified by chromatography using a gradient from dichloromethane to ethyl acetate to give (2S,4S)-1-allyloxycarbonyl-2-(5-allyloxycarbonyl-2-cyanophenylcarbamoyl)pyrrolidin-4-ylthioacetate (0.9 g, 93%). Nmr (CDCl$_3$): δ 2.32 (s, 3H); 2.63 (br, 2H); 3.46 (dd, 1H); 4.06 (quintet, 1H); 4.16 (dd, 1H); 4.64 (t, 1H); 4.71 (dt, 2H); 4.85 (dt, 2H); 5.22–5.47 (m, 4H); 5.87–6.14 (m, 2H); 7.67 (d, 1H); 7.87 (dd, 1H); 8.96 (d, 1H); 9.42 (br, 1H).

Ms (+ve FAB): 458 (MH)$^+$; 480 (M+Na)$^+$

The above thioacetate was deacetylated and condensed with carbapenem phosphate as Example 1, purifying by chromatography using a gradient from dichloromethane to ethyl acetate to give allyl (1R,5S,6S,8R,2'S,4'S)-2-(1-allyloxycarbonyl-2-(3-allyloxycarbonyl-2-methoxyphenylcarbamoyl)pyrrolidin-4-ylthio)-6-(1-hydroxyethyl)-1-methylcarbapenem-3-carboxylate. Nmr (CDCl$_3$): δ 1.24 (d, 3H); 1.35 (d, 3H); 2.60 (br, 2H); 3.25 (dd overlapping quintet, 2H); 3.52 (br, 1H); 3.88 (quintet, 1H); 4.02 (dd, 1H); 4.25 (quintet, 1H); 4.28 (dd, 1H); 4.55–4.74 (m, 5H); 4.85 (dt, 2H); 5.18–5.468 (m, 6H); 5.83–6.11 (m, 3H); 7.65 (dt, 1H); 7.87 (dd, 1H); 9.00 (br s, 1H); 9.25 (br, 1H).

Ms (+ve FAB): 665 (MH)$^+$; 687 (M+Na)$^+$

EXAMPLE 36

(1R,5S,6S,8R,2'S,4'S)-2-(2-(3-carboxy-5-fluorophenylcarbamoyl)pyrrolidin-4-ylthio)-6-(1-hydroxyethyl)-1-methylcarbapenem-3-carboxylic acid, disodium salt was prepared using the technique of Example 2, except that the DMF was replaced by DMSO. Nmr (DMSO-d$_6$+acetic acid-d$_4$): δ 1.20 (d, 6H); 1.99 (dt, 1H); 2.91 (dt, 1H); 3.26 (dd overlapping m, 3H); 3.42 (quintet, 1H); 3.74 (dd, 1H); 3.96 (quintet, 1H); 4.04 (quintet, 1H); 4.22 (dd, 1H); 4.41 (t, 1H); 7.43 (dm, 1H); 7.81 (dd, 1H); 8.00 (t, 1H).

Ms (+ve FAB): 516 (MH)$^+$, (Na salt); 538 (MH)$^+$, (Na$_2$ salt)

The starting materials were prepared as follows:
3-Fluoro-5-nitrobenzoic acid

A vigorously stirred slurry of nitrosonium tetrafluoroborate (3.53 g, 30.2 mM) in acetonitrile (50 ml) under an atmosphere of argon was cooled in an ice bath, and 3-amino-5-nitrobenzoic acid (5.0 g, 27.5 mM) was added in three portions. The temperature was then allowed to rise to ambient, and the mixture was stirred for 48 hours. 1,2-Dichlorobenzene (50 ml) was added, and acetonitrile distilled from the mixture at reduced pressure. The mixture was then heated to 170° for 30 minutes, when gas evolution had ended. After cooling, the mix was poured into dichloromethane (200 ml), and extracted with NaHCO$_3$ solution. After back washing the aqueous phase with dichloromethane, it was acidified (2M hydrochloric acid), and organics extracted with ethyl acetate (2×100 ml). The combined organic layers were washed with brine, and dried over MGgSO$_4$. Crude product was purified by chromatography on silica, eluting with a gradient from dichloromethane/acetic acid (99:1) to dichloromethane/isopropanol/acetic acid (80:20:1), to give 3-fluoro-5-nitrobenzoic acid (3.26 g, 64%). Nmr (DMSO-d$_6$): δ 8.14 (dm, 1H); 8.37 (dt, 1H); 8.46 (m, 1H).

Ms (EI): 185H

Allyl 3-fluoro-5-nitrobenzoate

3-Fluoro-5-nitrobenzoic acid (3 g, 16.2 mM), p-toluenesulfonic acid (1.54 g, 8.1 mM), and allyl alcohol (50 ml) were heated to reflux, passing the distillate through 3a molecular sieves, for 16 hours. After cooling, the mixture was neutralised with triethylamine, and solvent removed. The residue was dissolved in ethyl acetate, washed with 2M hydrochloric acid, aqueous NaHCO$_3$, and brine, and dried over MgSO$_4$. Crude product was purified by chromatography on silica, using a gradient elution from dichloromethane to ethyl acetate/dichloromethane (3:1), to give allyl 3-fluoro-5-nitrobenzoate. Nmr (CDCl$_3$: δ 4.89 (dt, 2H); 5.33–5.49 (m, 2H); 5.95–6.15 (m, 1H); 8.11 (m, 2H); 8.70 (t, 1H).

Ms (CI): 226 (MH)$^+$; 253 (M+C$_2$H$_5$)$^+$

Reduction of the above nitro compound by the method of Example 1 gave allyl 3-amino-5-fluorobenzoate. Nmr (CDCl$_3$): δ 3.89 (br, 2H); 4.79 (dt, 2H); 5.25–5.45 (m, 2H); 5.92–6.12 (m, 1H); 6.54 (dt, 1H); 7.07–7.15 (m, 2H).

Ms (CI): 196 (MH)$^+$

The above amine was condensed with proline acid as Example 1, purifying by chromatography using a gradient from dichloromethane to dichloromethane/diethyl ether (85:13) to give (2S,4S)-1-allyloxycarbonyl-2-(3-allyloxycarbonyl-5-fluorophenylcarbamoyl)pyrrolidin-4-ylthioacetate. Nmr (CDCl$_3$): δ 2.33 (s, 3H); 2.59 (br, 2H); 3.48 (dd, 1H); 4.03 (quintet, 1H); 4.13 (dd, 1H); 4.56 (t, 1H); 4.68 (dt, 2H); 4.82 (dt, 2H); 5.25–5.46 (m, 4H); 5.86–6.11 (m, 2H); 6.47 (dm, 1H); 7.72 (t, 1H); 7.87 (dt m, 1H); 9.38 (br, 1H).

Ms (+ve FAB): 451 (MH)$^+$; 473 (M+Na)$^+$

The above thioacetate was deacetylated and condensed with carbapenem phosphate as Example 1, purifying by chromatography using a gradient from dichloromethane to ethyl acetate to give allyl (1R,5S,6S,8R,2'S,4'S)-2-(1-allyloxycarbonyl-2-(3-allyloxycarbonyl-5-fluorophenylcarbamoyl)pyrrolidin-4-ylthio)-6-(1-hydroxyethyl)-1-methylcarbapenem-3-carboxylate. Nmr (CDCl$_3$): δ 1.24 (d, 3H); 1.36 (d, 3H); 2.63 (br, 2H); 3.26 (dd, 1H); 3.29 (quintet, 1H); 3.48 (br, 1H); 3.81 (quintet, 1H); 3.97 (dd, 1H); 4.27 (dd overlapping m, 2H); 4.54 (t, 1H); 4.62–4.76 (m, 4H); 4.81 (dt, 2H); 5.20–5.46 (m, 6H); 5.85–6.10 (m overlapping br, 3H); 7.48 (dt, 1H); 7.83 (br s, 1H); 7.88 (dt, 1H); 9.18 (br, 1H).

Ms (+ve FAB): 658 (MH)$^+$; 680 (M+Na)$^+$

EXAMPLE 37

(1R,5S,6S,8R,2'S,4'S)-2-(2-(3-carboxy-N'-methylphenylcarbamoyl)pyrrolidin-4-ylthio)-6-(1-hydroxyethyl)-1-methylcarbapenem-3-carboxylic acid, disodium salt was prepared using the technique of Example 2, except that the DMF was replaced by DMSO, and product was purified by chromatography on a CHP20P column, eluting with water. Nmr (DMSO-d$_6$+acetic acid-d$_4$, run at 50°): δ 1.12 (d, 3H); 1.18 (d, 3H); 1.67 (br, 1H); 2.13 (br, 1H); 3.02 (dd, 1H); 3.17 (dd, 1H); 3.28 (s overlapping m, 5H); 3.65 (br, 1H); 3.98 (quintet overlapping m, 2H); 4.12 (dd, 1H); 7.58 (d, 1H); 7.91 (d, 1H); 7.98 (m, 1H).

Ms (+ve FAB): 512 (MH)$^+$, (Na salt); 534 (MH)$^+$, (Na$_2$ salt)

The starting materials were prepared as follows:

Allyl 3-methylaminobenzoate

Allyl 3-aminobenzoate (5 g, 28.2 mM) was dissolved in triethyl orthoformate (50 ml) and trifluoroacetic acid (5 drops) was added. The solution was stirred and refluxed up through 3 Å molecular sieves for 5 hours. Solvent was removed, and the residue dissolved in ethanol (50 ml), followed by the addition of acetic acid (8.08 ml) and sodium cyanoborohydride (6.85 g, 0.108M) in several portions. The mixture was stirred at ambient temperature for 16 hours, and solvent removed. The residue was dissolved in diethyl ether, washed with water, brine, and dried over MgSO$_4$. Crude product was purified by chromatography on silica, eluting with a gradient from dichloromethane to dichloromethane/ ethyl acetate (95:5), to give allyl 3-methylaminobenzoate (0.93 g, 17%). Nmr (CDCl$_3$): δ 2.88 (s, 3H); 4.81 (dt, 2H); 5.23–5.45 (m, 2H); 5.94–6.13 (m, 1H); 6.83 (dd, 1H); 7.25 (dd, 1H); 7.33 (t, 1H); 7.43 (dm, 1H).

Ms (CI): 192 (MH)$^+$

The above amine was condensed with proline acid as Example 1, purifying by chromatography using a gradient from dichloromethane to dichloromethane/diethyl ether (4:1) to give (2S,4S)-1-allyloxycarbonyl-2-(3-allyloxycarbonyl-N'-methylphenylcarbamoyl)pyrrolidin-4-ylthioacetate. Nmr (CDCl$_3$, mixture of rotamers): δ 1.93 (m, 1H); 2.32 (s, 3H); 2.48 (m, part obscured, 1H); 3.28, 3.31 (2xs, 3H); 3.40 (quintet, 1H); 3.76 (m, 1H); 4.01 (m, 1H); 4.24 (m, 1H); 4.50–4.74 (m, 2H); 4.86 (d, 2H); 5.18–5.48 (m, 4H); 5.84–6.13 (m, 2H); 7.38–7.68 (m, 2H); 7.90–8.11 (m, 2H).

Ms (+ve FAB): 447 (MH)$^+$; 469 (M+Na)$^+$

The above thioacetate was deacetylated and condensed with carbapenem phosphate as Example 1, purifying by chromatography using a gradient from dichloromethane to ethyl acetate to give allyl 1R,5S,6S,8R,2'S,4'S)-2-(1-allyloxycarbonyl-2-(3-allyloxycarbonyl-N'-methylphenylcarbamoyl)pyrrolidin-4-ylthio)-6-(1-hydroxyethyl)-1-methylcarbapenem-3-carboxylate. Nmr (CDCl$_3$, mixture of rotamers): δ 1.20 (2xd, 3H); 1.34 (2xd, 3H); 1.87 (br, 1H); 2.30 (br, 1H); 3.29, 3.31 (2xs, overlapping m, 6H); 4.05–4.30 (m, 4H); 4.50–4.81 (m, 5H); 4.96 (d, 2H); 5.20–5.48 (m, 6H); 5.85–6.13 (m, 3H); 7.39–7.68 (m, 2H); 7.91–8.11 (m, 2H).

Ms (+ve FAB): 654 (MH)$^+$; 676 (M+Na)$^+$

We claim:

1. A process for preparing a compound of the formula (I)

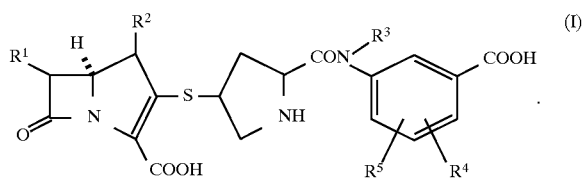

or a pharmaceutically acceptable salt or in vivo hydrolysable ester thereof wherein:

$R^1$ is 1-hydroxyethyl, 1-fluoroethyl or hydroxymethyl;

$R^2$ is hydrogen or $C_{1-4}$alkyl;

$R^3$ is hydrogen or $C_{1-4}$alkyl;

$R^4$ and $R^5$ are the same or different and are selected from hydrogen, halo, cyano, $C_{1-4}$alkyl, nitro, hydroxy, carboxy, $C_{1-4}$alkoxy, $C_{1-4}$alkoxycarbonyl, aminosulphonyl, $C_{1-4}$alkylaminosulphonyl, di-$C_{1-4}$-alkylaminosulphonyl, carbamoyl, $C_{1-4}$alkylcarbamoyl, di-$C_{1-4}$alkylcarbamoyl, trifluoromethyl, sulphonic acid, amino, $C_{1-4}$alkylamino, di-$C_{1-4}$alkylamino, $C_{1-4}$alkanoylamino, $C_{1-4}$alkanoyl(N—$C_{1-4}$alkyl) amino, $C_{1-4}$alkanesulphonamido and —S(O)$_n$C$_{1-4}$alkyl and wherein n is zero, one or two;

with the proviso that there is no hydroxy or carboxy substituent in a position ortho to the link to —NR$^3$— which process comprises:

reacting a compound of formula (VI) with a compound of formula (VII):

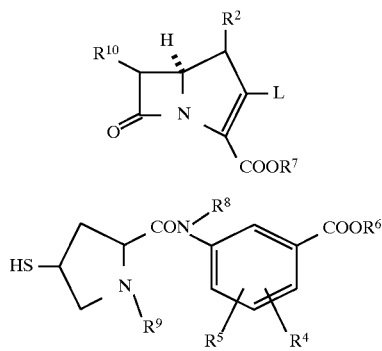

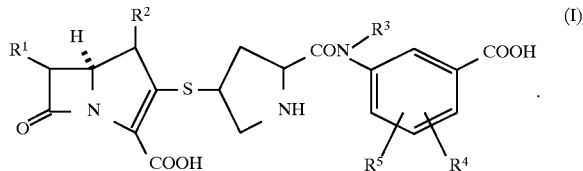

wherein $R^2$, $R^4$, and $R^5$ are as defined above, $R^4$ and $R^5$ optionally being protected —$COOR^6$ and —$COOR^7$ are carboxy or protected carboxy; $R^8$ is a group $R^3$ as defined above, or an amino protecting group; $R^9$ is hydrogen or an amino protecting group; and $R^{10}$ is a group $R^1$, as defined above, protected 1-hydroxyethyl or protected hydroxymethyl; and L is a leaving group;

and wherein any functional group is optionally protected and thereinafter optionally:
(i) removing any protecting groups;
(ii) forming a pharmaceutically acceptable salt; and
(iii) esterifying hydroxy and carboxy groups to form an in vivo hydrolysable ester.

2. A process for preparing a compound of the formula (I)

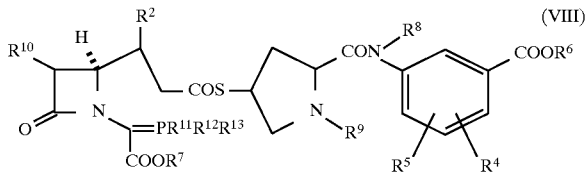

or a pharmaceutically acceptable salt or in vivo hydrolysable ester thereof wherein:

$R^1$ is 1-hydroxyethyl, 1-fluoroethyl or hydroxymethyl;
$R^2$ is hydrogen or $C_{1-4}$alkyl;
$R^3$ is hydrogen or $C_{1-4}$alkyl;
$R^4$ and $R^5$ are the same or different and are selected from hydrogen, halo, cyano, $C_{1-4}$alkyl, nitro, hydroxy, carboxy, $C_{1-4}$alkoxy, $C_{1-4}$alkoxycarbonyl, aminosulphonyl, $C_{1-4}$alkylaminosulphonyl, di-$C_{1-4}$-alkylaminosulphonyl, carbamoyl, $C_{1-4}$alkylcarbamoyl, di-$C_{1-4}$alkylcarbamoyl, trifluoromethyl, sulphonic acid, amino, $C_{1-4}$alkylamino, di-$C_{1-4}$alkylamino, $C_{1-4}$alkanoylamino, $C_{1-4}$alkanoyl(N—$C_{1-4}$alkyl) amino, $C_{1-4}$alkanesulphonamido and —$S(O)_nC_{1-4}$alkyl and wherein n is zero, one or two;

with the proviso that there is no hydroxy or carboxy substituent in a position ortho to the link to —$NR^3$—, which process comprises:

cyclising a compound of the formula (VIII):

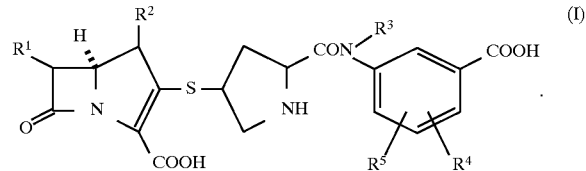

wherein $R^2$, $R^4$, and $R^5$ are as defined above, $R^4$ and $R^5$ optionally being protected; —$COOR^6$ and —$COOR^7$ are carboxy or protected carboxy; $R^8$ is a group $R^3$ as defined above, or an amino protecting group; $R^9$ is hydrogen or an amino protecting group; and $R^{10}$ is a group $R^1$, as defined above, protected 1-hydroxyethyl or protected hydroxymethyl; $R^{11}$–$R^{13}$ are independently selected from $C_{1-6}$alkoxy, aryloxy, di-$C_{1-6}$alkylamino and diarylamino or any two of $R^{11}$–$R^{13}$ represents o-phenylenedioxy; or one of $R^{11}$–$R^{13}$ is $C_{1-4}$alkyl, allyl, benzyl or phenyl and the other two values are independently selected from $C_{1-4}$alkyl, trifluoromethyl or phenyl, wherein any phenyl group is optionally substituted with $C_{1-3}$alkyl or $C_{1-3}$alkoxy;

and wherein any functional group is optionally protected and thereinafter optionally:
(i) removing any protecting groups;
(ii) forming a pharmaceutically acceptable salt; and
(iii) esterifying hydroxy and carboxy groups to form an in vivo hydrolysable ester.

3. A process for preparing a compound of the formula (I)

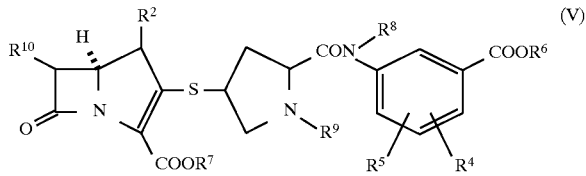

a pharmaceutically acceptable salt or in vivo hydrolysable ester thereof wherein:

$R^1$ is 1-hydroxyethyl, 1-fluoroethyl or hydroxymethyl;
$R^2$ is hydrogen or $C_{1-4}$alkyl;
$R^3$ is hydrogen or $C_{1-4}$alkyl;
$R^4$ and $R^5$ are the same or different and are selected from hydrogen, halo, cyano, $C_{1-4}$alkyl, nitro, hydroxy, carboxy, $C_{1-4}$alkoxy, $C_{1-4}$alkoxycarbonyl, aminosulphonyl, $C_{1-4}$alkylaminosulphonyl, di-$C_{1-4}$-alkylaminosulphonyl, carbamoyl, $C_{1-4}$alkylcarbamoyl, di-$C_{1-4}$alkylcarbamoyl, trifluoromethyl, sulphonic acid, amino, $C_{1-4}$alkylamino, di-$C_{1-4}$alkylamino, $C_{1-4}$alkanoylamino, $C_{1-4}$alkanoyl(N—$C_{1-4}$alkyl) amino, $C_{1-4}$alkanesulphonamido and —$S(O)_nC_{1-4}$alkyl and wherein n is zero, one or two;

with the proviso that there is no hydroxy or carboxy substituent in a position ortho to the link to —$NR^3$—, which process comprises:

deprotecting a compound of the formula (V):

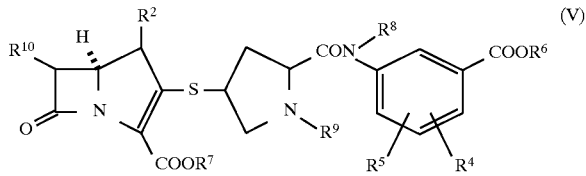

wherein $R^2$, $R^4$, and $R^5$ are as defined above, $R^4$ and $R^5$ optionally being protected; —$COOR^6$ and —$COOR^7$ are carboxy or protected carboxy; $R^8$ is a group $R^3$ as defined above, or an amino protecting group; $R^9$ is hydrogen or an amino protecting group; and $R^{10}$ is a group $R^1$, as defined above, protected 1-hydroxyethyl or protected hydroxymethyl; and wherein at least one protecting group is present; and thereafter optionally;
(i) forming a pharmaceutically acceptable salt,
(ii) esterifying hydroxy and carboxy groups to form an in vivo hydrolysable ester.

4. The process according to any one of claims 1, 2 and 3, wherein $R^1$ is 1-hydroxyethyl.

5. The process according to any one of claims 1, 2 and 3, wherein $R^2$ is hydrogen or methyl.

6. The process according to any one of claims 1, 2 and 3, wherein $R^2$ is methyl.

7. The process according to any one of claims 1, 2 and 3, wherein $R^3$ is hydrogen.

8. The process according to any one of claims 1, 2 and 3, wherein the compound prepared has the structure of formula formula (IV):

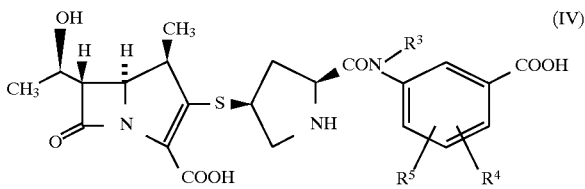

9. The process according to claim 8 wherein $R^4$ and $R^5$ are the same or different and selected from hydrogen, fluoro, chloro, hydroxy, carboxy, cyano, nitro, methyl, ethyl, methoxy, ethoxy, methoxycarbonyl, carbamoyl, methylcarbamoyl, dimethylcarbamoyl, trifluoromethyl, sulphonic acid, methylsulphinyl, methylsulphonyl, methanesulphonamido or acetamido.

10. The process according to claim 8 wherein at least one of $R^4$ and $R^5$ is hydrogen.

11. The process according to claim 8 wherein $R^4$ is hydrogen, carboxy, fluoro, chloro, methyl, methoxy, cyano, sulphonic acid or methoxycarbonyl and $R^5$ is hydrogen.

12. The process according to any one of claims 1, 2 and 3 wherein the compound prepared is (1R,5S,6S,8R,2'S,4'S)-2-(2-(3-carboxyphenylcarbamoyl)pyrrolidin-4-ylthio)-6-(1-hydroxyethyl)-1-methylcarbapenem-3-carboxylic acid or a pharmaceutically acceptable salt or in vivo hydrolysable ester thereof.

13. The process according to any one of claims 1, 2 and 3 wherein the compound prepared is (1R,5S,6S,8R,2'S,4'S)-2-(2-(3-carboxyphenylcarbamoyl)pyrrolidin-4-ylthio)-6-(1-hydroxyethyl)-1-methylcarbapenem-3-carboxylic acid.

14. The process according to any one of claims 1, 2 and 3 wherein the compound prepared is (1R,5S,6S,8R,2'S,4'S)-2-(2-(3-carboxyphenylcarbamoyl)pyrrolidin-4-ylthio)-6-(1-hydroxyethyl)-1-methylcarbapenem-3-carboxylic acid in the form of a monosodium salt.

15. The process according to any one of claims 1, 2 and 3 wherein the compound prepared is (1R,5S,6S,8R,2'S,4'S)-2-(2-(3-carboxyphenylcarbamoyl)pyrrolidin-4-ylthio)-6-(1-hydroxyethyl)-1-methylcarbapenem-3-carboxylic acid in the form of a disodium salt.

16. The process according to claim 1 wherein the compound prepared is (1R,5S,6S,8R,2'S,4'S)-2-(2-(3-carboxyphenylcarbamoyl)pyrrolidin-4-ylthio)-6-(1-hydroxyethyl)-1-methylcarbapenem-3-carboxylic acid in the form of a disodium salt which process comprises reacting (2S,4S)-1-allyloxycarbonyl-2-(3-allyloxycarbonylphenylcarbamoyl)pyrrolidin-4-yl-thiol with allyl(1R,5R,6S,8R)-6-(1-hydroxyethyl)-1-methyl-2-diphenylphosphoryloxycarbapenem-3-carboxylate, and thereafter removing any protecting groups.

17. The process according to claim 1 in which the leaving group L is diphenylphosphoric ester (—OP(O)(OPh)$_2$).

18. The process according to claim 1 in which the reaction of compounds of formulae VI and VII is performed in the presence of the base diisopropylethylamine.

19. The process according to claim 1 in which the reaction of compounds of formulae VI and VII is performed at a temperature of between −25° C. and ambient.

20. The process according to claim 1 in which the reaction of compounds of formulae VI and VII is performed at a temperature of −20° C.

21. The process according to claim 1 in which the reaction of compounds of formulae VI and VII is performed at a temperature of −15° C.

22. The process according to claim 1 in which the reaction of compounds of formulae VI and VII is performed in the organic solvent acetonitrile.

23. The process according to claim 1 in which the reaction of compounds of formulae VI and VII is performed in acetonitrile at −20° C. in the presence of diisopropylethylamine.

24. The process according to claim 1 in which the reaction of compounds of formulae VI and VII is performed in acetonitrile at −15° C. in the presence of diisopropylethylamine.

25. The process according to claim 1 wherein the compound prepared is (1R,5S,6S,8R,2'S,4'S)-2-(2-(3-carboxyphenylcarbamoyl)pyrrolidin-4-ylthio)-6-(1-hydroxyethyl)-1-methylcarbapenem-3-carboxylic acid in the form of a disodium salt which process comprises reacting (2S,4S)-1-(4-nitrobenzyloxycarbonyl)-2-(3-allyloxycarbonylphenylcarbamoyl)pyrrolidin-4-yl-thiol with 4-nitrobenzyl(1R,5R,6S,8R)-6-(1-hydroxyethyl)-1-methyl-2-diphenylphosphoryloxycarbapenem-3-carboxylate, and thereafter removing any protecting groups.

26. The process according to claim 2 wherein $R^{11}$–$R^{13}$ are independently selected from methoxy, ethoxy, isopropoxy, n-propoxy, n-butoxy, phenoxy, dimethylamino, diethylamino and diphenylamino or any two of $R^{11}$–$R^{13}$ represent o-phenylenedioxy.

27. The process according to claim 2 wherein $R^{11}$–$R^{15}$ each have the same value and are selected from methoxy, ethoxy, isopropoxy, n-butoxy and phenoxy.

28. The process according to claim 2 in which the cyclisation of the compound of formula VIII is performed at a temperature in the region of 60°–15° C.

29. The process according to claim 2 in which the cyclisation of the compound of formula VIII is performed in toluene, xylene or ethyl acetate.

30. The process according to claim 2 in which the cyclisation of the compound of formula VIII is performed in an atmosphere of nitrogen.

31. The process according to claim 2 in which the cyclisation of the compound of formula VIII is performed in the presence of a radical scavenger.

32. The process according to claim 2 in which the cyclisation of the compound of formula VIII is performed in the presence of hydroquinone.

33. The process according to claim 3 wherein the compound prepared is (1R,5S,6S,8R,2'S,4'S)-2-(2-(3-carboxyphenylcarbamoyl)pyrrolidin-4-ylthio)-6-(1-hydroxyethyl)-1-methylcarbapenem-3-carboxylic acid in the form of a disodium salt which process comprises deprotecting allyl (1R,5S,6S,8R,2'S,4'S)-2-(1-allyloxycarbonyl-2-(3-allyloxycarbonylphenylcarbamoyl)pyrrolidin-4-ylthio)-6-(1-hydroxyethyl)-1-methylcarbapenem-3-carboxylate.

34. The process according to claim 3 wherein the compound prepared is (1R,5S,6S,8R,2'S,4'S)-2-(2-(3-carboxyphenylcarbamoyl)pyrrolidin-4-ylthio)-6-(1-hydroxyethyl)-1-methylcarbapenem-3-carboxylic acid in the form of a disodium salt which process comprises adding to a solution of allyl(1R,5S,6S,8R,2'S,4'S)-2-(1-allyloxycarbonyl-2-(3-allyloxycarbonylphenylcarbamoyl)pyrrolidin-4-ylthio)-6-(1-hydroxyethyl)-1-methylcarbapenem-3-carboxylate and 2,2-dimethyl-1,3-dioxane-4,6-dione in a mixture of a dimethylformamide and tetrahydrofuran, under an argon atmosphere, tetrakis (triphenylphosphine)palladium, then gently warming the solution with protection from light and then adding sodium 2-ethylhexanoate in tetrahydrofuran and dimethyl sulfoxide.

35. The process according to claim 3 wherein the compound prepared is (1R,5S,6S,8R,2'S,4'S)-2-(2-(3-carboxyphenylcarbamoyl)pyrrolidin-4-ylthio)-6-(1-hydroxyethyl)-1-methylcarbapenem-3-carboxylic acid in the form of a disodium salt which process comprises deprotecting 4-nitrobenzyl(1R,5S,6S,8R,2'S,4'S)-2-(2-(3-allyloxycarbonylphenylcarbamoyl)-1-(4-nitrobenzyloxycarbonyl)pyrrolidin-4-ylthio)-6-(1-hydroxyethyl)-1-methylcarbapenem-3-carboxylate.

36. The process according to claim 3 wherein the compound prepared is (1R,5S,6S,8R,2'S,4'S)-2-(2-(3-carboxyphenylcarbamoyl)pyrrolidin-4-ylthio)-6-(1-hydroxyethyl)-1-methylcarbapenem-3-carboxylic acid in the form of a disodium salt which process comprises adding to a solution of 4-nitrobenzyl(1R,5S,6S,8R,2'S,4'S)-2-(2-(3-allyloxycarbonylphenylcarbamoyl)-1-(4-nitrobenzyloxycarbonyl)pyrrolidin-4-ylthio)-6-(1-hydroxyethyl)-1-methylcarbapenem-3-carboxylate and Meldrum's acid in tetrahydrofuran, under an atmosphere of argon and with the exclusion of light, tetrakis (triphenylphosphine)palladium, then after stirring at ambient temperature, diluting with ethyl acetate, adding the mixture to a solution of sodium bicarbonate in distilled water, adding 10% Pd-charcoal and leaving in an atmosphere of hydrogen.

37. A process for preparing the compound (1R,5S,6S,8R,2'S,4'S)-2-(2-(3-carboxyphenylcarbamoyl)pyrrolidin-4-ylthio)-6-(1-hydroxyethyl)-1-methylcarbapenem-3-carboxylic acid in the form of a disodium salt which process comprises reacting (1R,5S,6S,8R,2'S,4'S)-2-(2-(3-carboxyphenylcarbamoyl)pyrrolidin-4-ylthio)-6-(1-hydroxyethyl)-1-methylcarbapenem-3-carboxylic acid with sodium 2-ethylhexanoate in tetrahydrofuran and dimethyl sulfoxide.

* * * * *